United States Patent
Boulas et al.

(10) Patent No.: US 11,291,642 B2
(45) Date of Patent: Apr. 5, 2022

(54) DIMETHYL FUMARATE PARTICLES AND PHARMACEUTICAL COMPOSITIONS THEREOF

(71) Applicant: BIOGEN MA INC., Cambridge, MA (US)

(72) Inventors: Pierre Boulas, Andover, MA (US); Erwin Irdam, Melrose, MA (US); Shyam B. Karki, Hillsborough, NJ (US); William F. Kiesman, Wayland, MA (US); Cheuk-Yui Leung, Acton, MA (US); Yiqing Lin, Lexington, MA (US); Andrea Trementozzi, Sherborn, MA (US); Peter Zawaneh, Brookline, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 15/737,011

(22) PCT Filed: Jun. 15, 2016

(86) PCT No.: PCT/US2016/037486
§ 371 (c)(1),
(2) Date: Dec. 15, 2017

(87) PCT Pub. No.: WO2016/205270
PCT Pub. Date: Dec. 22, 2016

(65) Prior Publication Data
US 2019/0070143 A1 Mar. 7, 2019

Related U.S. Application Data

(60) Provisional application No. 62/181,061, filed on Jun. 17, 2015.

(51) Int. Cl.
| | |
|---|---|
| *A61K 31/225* | (2006.01) |
| *A61K 9/00* | (2006.01) |
| *A61K 9/50* | (2006.01) |
| *A61K 9/14* | (2006.01) |
| *A61K 9/48* | (2006.01) |
| *A61K 9/16* | (2006.01) |
| *A61K 47/10* | (2017.01) |
| *A61K 47/14* | (2017.01) |
| *A61K 47/42* | (2017.01) |
| *A61P 25/00* | (2006.01) |

(52) U.S. Cl.
CPC .......... *A61K 31/225* (2013.01); *A61K 9/0002* (2013.01); *A61K 9/0065* (2013.01); *A61K 9/14* (2013.01); *A61K 9/1635* (2013.01); *A61K 9/4808* (2013.01); *A61K 9/5026* (2013.01); *A61K 9/5084* (2013.01); *A61K 47/10* (2013.01); *A61K 47/14* (2013.01); *A61K 47/42* (2013.01); *A61K 9/1682* (2013.01); *A61P 25/00* (2018.01)

(58) Field of Classification Search
CPC combination set(s) only.
See application file for complete search history.

(56) References Cited

U.S. PATENT DOCUMENTS

| | | | |
|---|---|---|---|
| 8,609,136 B2 | 12/2013 | Tsabari et al. | |
| 2008/0233185 A1 | 9/2008 | Joshi et al. | |
| 2012/0034274 A1* | 2/2012 | Nilsson | A61K 9/2846 424/400 |

FOREIGN PATENT DOCUMENTS

| | | |
|---|---|---|
| WO | 2006/037342 A2 | 4/2006 |
| WO | 2009/144558 A1 | 12/2009 |
| WO | 2010079222 A1 | 7/2010 |
| WO | 2012/170923 A1 | 12/2012 |
| WO | 2013/076216 A1 | 5/2013 |
| WO | 2013/119677 A1 | 8/2013 |
| WO | 2015/042294 A1 | 3/2015 |
| WO | 2015/044853 A2 | 4/2015 |
| WO | 2015/089420 A1 | 6/2015 |
| WO | 2015/130998 A1 | 9/2015 |

OTHER PUBLICATIONS

AIHC Pharma Forum: Occupational Toxicology, IH and Containment Challenges associated with an API (Jun. 3, 2015) pp. 1-17.
Lin et al., Effects of baffle configuration and tank size on spherical agglomerates of dimethyl fumarate in a common stirred tank, International Journal of Pharmaceutics 495 (Sep. 15, 2015) 886-894.
Loh et al., Overview of milling techniques for improving the solubility of poorly water-soluble drugs, Asian Journal of Pharmaceutical Sciences 10 (2015) 255-274.
Chinese Office Action for Application No. 201680047251.2, dated Apr. 8, 2020, 61 pages.
Chinese Office Action for Application No. 201680047251.2, dated Mar. 15, 2021, 32 pages.

* cited by examiner

*Primary Examiner* — Kathrien A Cruz
(74) *Attorney, Agent, or Firm* — McCarter & English, LLP; Steven G. Davis; Xin Zhang

(57) ABSTRACT

The present invention provides dimethyl fumarate (DMF) particles and methods of preparing the DMF particles. Also provided is DMF coated particles comprising DMF particles coated with an enteric coating. The invention also provides various dosage forms and methods of treating a disease or disorder (e.g., multiple sclerosis).

14 Claims, 20 Drawing Sheets

FIG. 8A
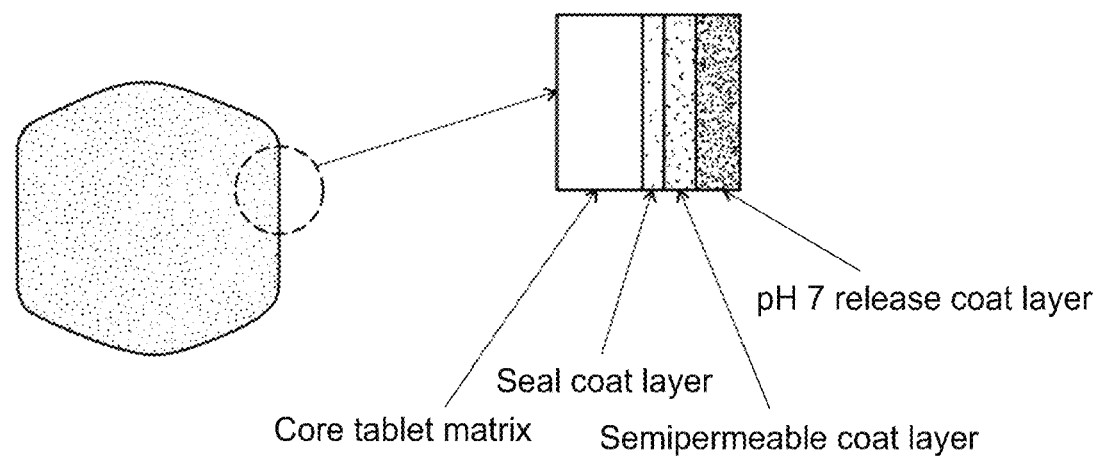
FIG. 8B
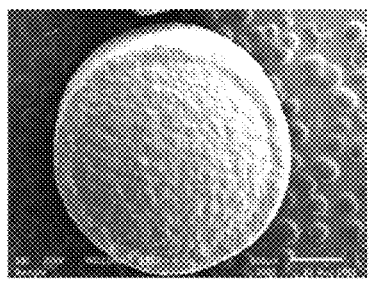
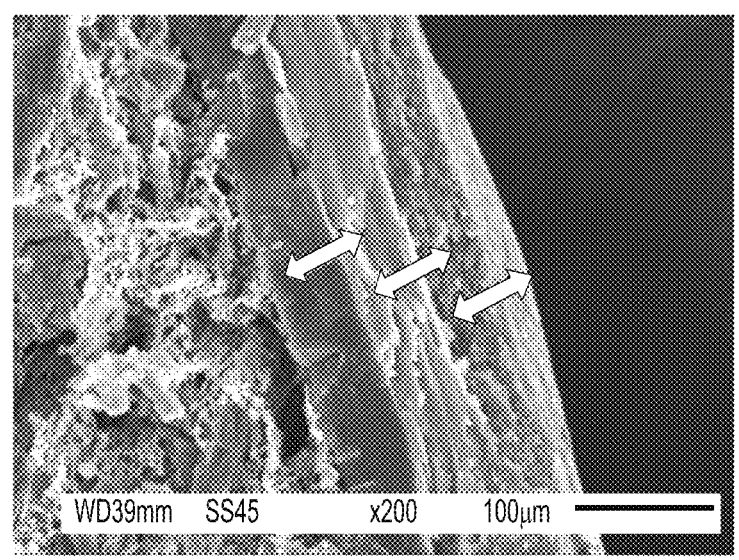

Swelling polymer
+ enteric & seal coated API

Unswelled tablet             Swelled tablet

- Swelling polymer
- Seal coated API
- Enteric coated tablet

- Swelling polymer
- Enteric & seal coated API

A DRAWING SHOWING THE PLACEMENT OF A SINGLE IMMEDIATE RELEASE
LAYER ON TOP OF THE OUTER IN A CROSS SECTION VIEW(A). AS SHOWN IN B, THE
IMMEDIATE RELEASE LAYER COVERS THE ENTIRE SURFACE OF THE GRDF

A DRAWING OF THE ULTRASOUND WELDING ON THE GRDF(A).
THE PERIMETER LINE OF THE INNER IS SHOWN WITH AN ARROW AND THE
EXTENT OF WELDING IN A CROSS SECTION OF THE GRDF IS PROVIDED (B).

AN ENLARGED PHOTOGRAPH OF A PART GRDF SHOWING THE ULTRASOUND WELDING OF THE PERIMETER (OUTER TO OUTER) SEALING THE ENVELOPE AND THE MORE CENTRAL WELDING OF THE OUTER TO THE INNER FILM.

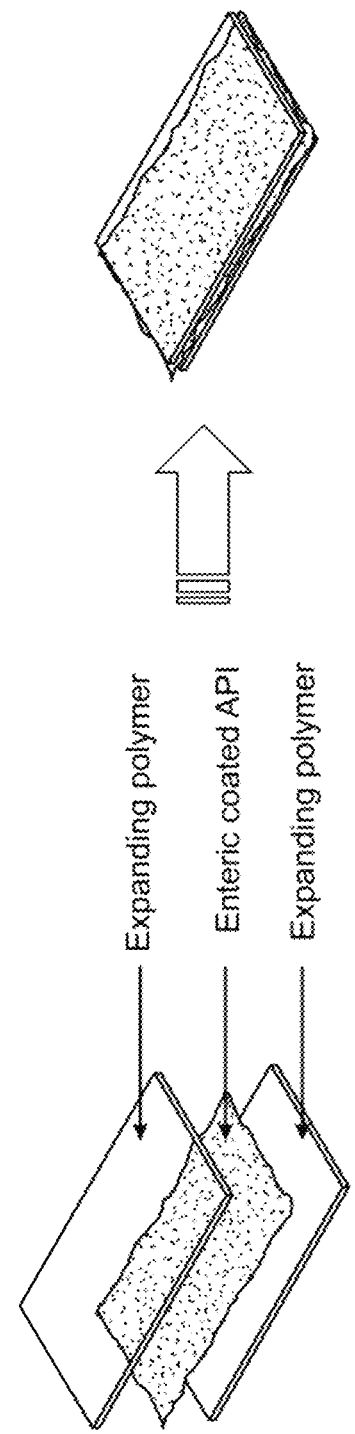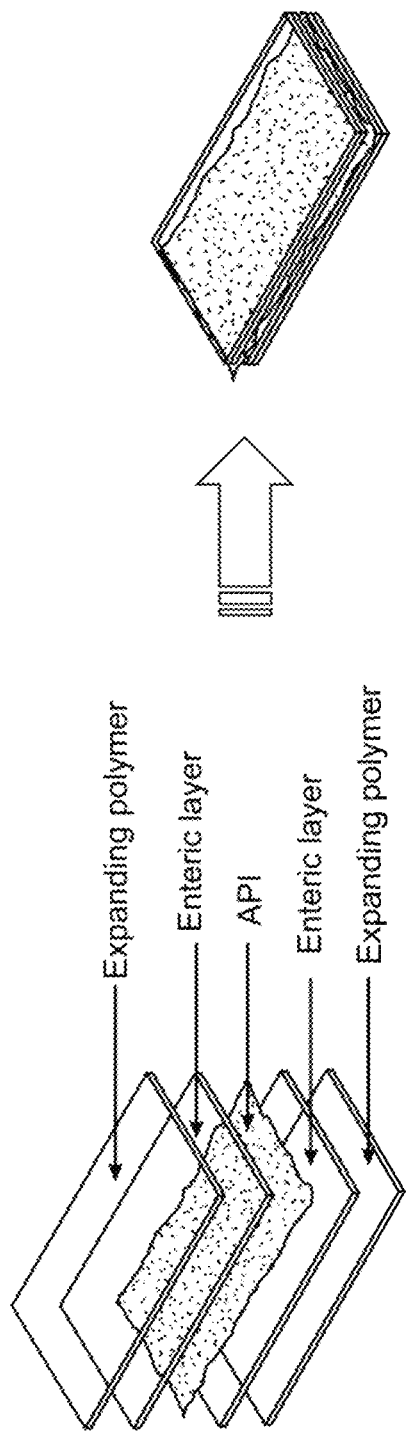

DIMETHYL FUMARATE PARTICLES AND PHARMACEUTICAL COMPOSITIONS THEREOF

REFERENCE TO RELATED APPLICATIONS

This application claims the benefit of the filing date, under 35 U.S.C. § 119(e), of U.S. Provisional Application No. 62/181,061, filed on Jun. 17, 2015, the entire content of which, including all drawings, formulae, specification, and claims, is incorporated herein by reference.

FIELD OF THE INVENTION

The present invention generally relates to dimethyl fumarate particles, pharmaceutical compositions and uses thereof.

BACKGROUND OF THE INVENTION

TECFIDERA™ has been approved by the U.S. Food and Drug Administration for the treatment of patients with relapsing forms of multiple sclerosis (MS). TECFIDERA™ contains dimethyl fumarate (DMF), which has the following structure:

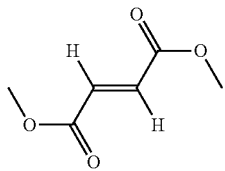

The starting dose for TECFIDERA™ is 120 mg twice a day orally. After 7 days, the dose is to be increased to the maintenance dose of 240 mg twice a day orally. TECFIDERA™ can be taken with or without food.

There is currently no FDA approved once a day dosing regimen, i.e., QD dosing, for DMF. One objective of the present invention is to develop a formulation (e.g., a unit dosage form) that is suitable for once a day dosing.

In addition, dimethyl fumarate (DMF) isolated from the current chemical synthesis needs to undergo a particle size reduction using a jet-milling process prior to drug product manufacturing. The reduced particles obtained by jet milling process have shown at times poor processability during drug product manufacture due to particle to particle cohesiveness.

Dimethyl fumarate also poses peculiar physical properties such as sublimation, low minimum ignition energy (MIE) and sensitizing effects so that the handling of this compound requires careful and at times tedious procedures to avoid employee exposures and ensure process safety (to avoid potential dust explosion.)

Therefore, there is a need for DMF particles with desirable bulk solid properties and manufacturing processability as well new processes for preparing such DMF particles with minimized safety risk.

SUMMARY OF THE INVENTION

In one aspect, the present invention provides pharmaceutical formulations (e.g., unit dosage forms) that are suitable for once a day dosing with DMF. The once a day formulations or unit dosage forms of the present invention are believed to have similar pharmacokinetic profile as the current FDA approved twice a day dosing regimen. In certain embodiments, the once a day unit dosage forms comprise two dosage components. Upon oral administration, the first dosage component provides a first immediate dose of DMF. The second dosage component is retained in stomach for a prolonged period of time, providing a delayed release of a second dose of DMF. Alternatively, the first dosage component is retained in the stomach and provides a delayed immediate dose of DMF; while the second dosage component is also retained in stomach for a prolonged period of time and provides a prolonged controlled release of a second dose of DMF. In certain embodiments, the present formulations or unit dosage forms can also improve DMF absorption into the blood stream.

It is known that DMF may cause gastrointestinal side-effects, such as nausea, vomiting and diarrhea. To minimize these GI side-effects, it is desirable that the unit dosage form of the present invention does not release significant amounts of DMF in stomach. Particularly, as the second dosage form and in some embodiments the first dosage form is retained in the stomach for a prolonged period time, it is essential to minimize the amount of DMF released when the dosage component is retained in the stomach. This objective is achieved by the enterically-coated DMF particles of the present invention. In certain embodiments, the enterically coated DMF particles of the present invention release no more than 20% DMF for 4 to 12 hours when subjected to an in vitro dissolution test employing USP Simulated Gastric Fluid (SGF) without pepsin as dissolution medium.

In another aspect, the present invention also provides DMF particles having desirable particle size, powder properties and morphology, suitable as starting material for preparing the enterically coated DMF particles of the present invention.

BRIEF DESCRIPTION OF THE DRAWINGS

FIG. 7C shows SEM images of coated DMF particles using unmilled coarse DMF; while

FIGS. 8A and 8B show a design of a delayed release tablet formulation. FIG. 8A shows a design of a coated delayed release minitablet/microtablet which contains a core tablet matrix, a seal coating layer, a semipermeable coating layer, and a pH7 release coating layer. FIG. 8B shows a picture and a microscopic view of a delayed release tablet having three coating layers: an inner seal coating layer, a semipermeable coating layer, and an outer pH 7 release coating layer.

FIGS. 20A and 20B shows exemplary designs for gastroretentive folded dosage form of the present invention. The dosage form shown in FIG. 20A has an internal layer comprising DMF coated particles of the present invention and two outer membranes sandwiching the internal layer therebetween. The dosage form shown in FIG. 20B has an internal layer comprising non-enterically coated DMF and two enteric layer sandwiching the internal layer therebetween. The dosage form also has two outer member covering the two enteric layer respectively.

DETAILED DESCRIPTION OF THE INVENTION

Figure 1:
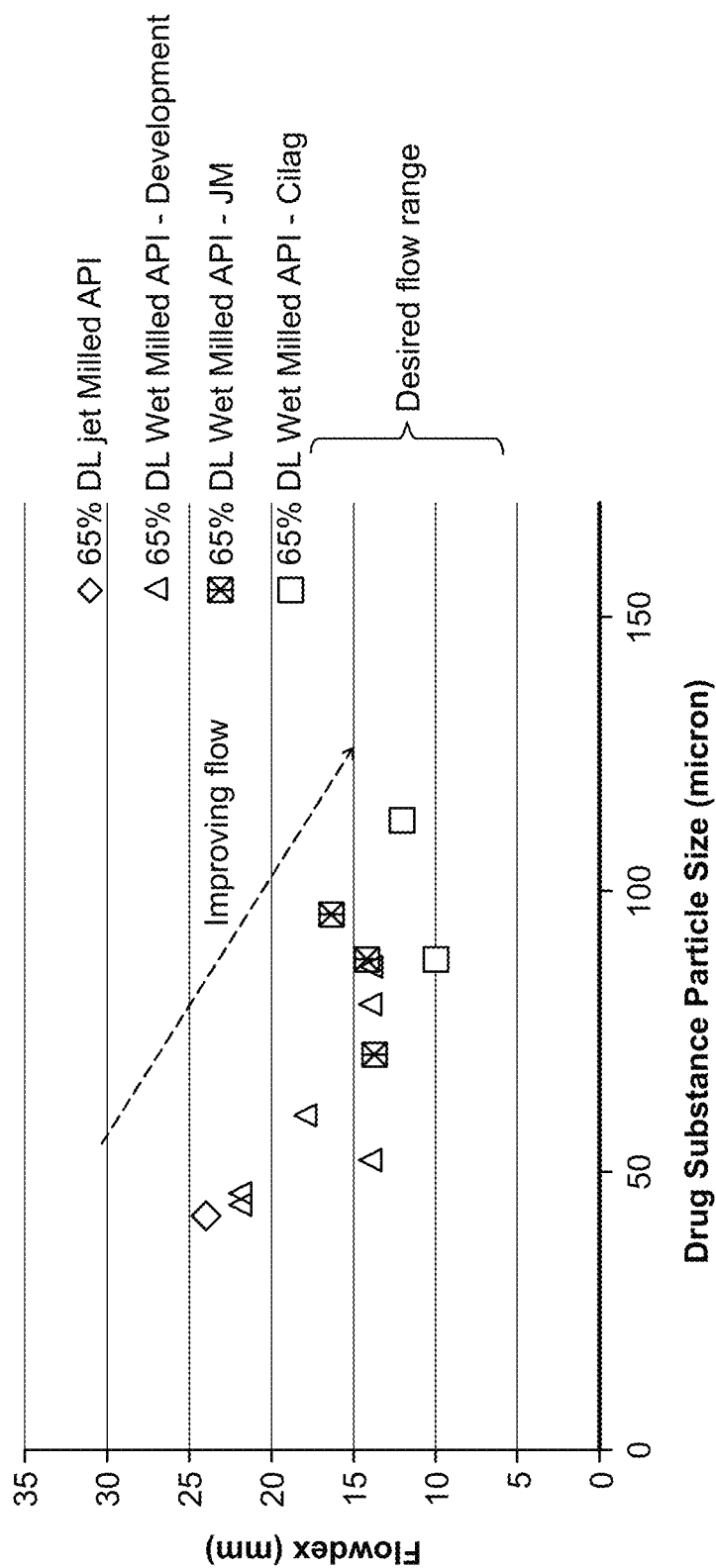
FIG. 1 shows flow measurements of drug product blend containing wet-milled dimethyl fumarate using Flodex. The y-axis indicates the aperture of cone containing the blend powder. Smaller aperture indicates better flow.

Reference will now be made in detail to certain embodiments of the invention, examples of which arc illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents that can be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention and different parts of the specification (including embodiments described only in the Examples) can be combined with one or more other embodiments of the invention, unless explicitly disclaimed or improper. Combination of embodiments are not limited to those specific combinations claimed via the multiple dependent claims.

Definitions

As use herein, the particle size is expressed in terms of volume diameter and the particle size distribution is expressed in terms of $D_{50}$, $D_{10}$, $D_{90}$ and span.

As particles are often non-spherical, it is difficult and complex to provide dimensional descriptions of these non-spherical particles. As used herein, "volume diameter" refers to diameter of a sphere with equal volume of the non-spherical particle.

In certain embodiments, the particle size described herein are measured using a laser diffraction technique that correlates light scattering to particle volume on which effective length or effective diameter is calculated. The distribution is based on a measurement of thousands of particles. Particle samples can be in dry form or in slurry. In one embodiment, the instrument used to determine particle size/distribution is a Beckman Coulter LS230 or a Malvern Mastersizer.

As used herein, "$D_{50}$", also known as the median diameter, corresponds to the value under which 50% of the particles has a lower volume diameter. "$D_{90}$" corresponds to the value under which 90% of the particles has a lower volume diameter. "$D_{10}$" corresponds to the value under which 10% of the particles has a lower volume diameter.

As used herein, "span" is a measure for particle size distribution. It is calculated according to the following equation:

$$Span = (D_{90} - D_{10})/D_{50}$$

In certain embodiments, powder characterization described herein can be determined using the FT4 Powder Rheometer (Freeman Technology Ltd, Tewkesbury, UK) with the 25 mm vessel assembly having 23.5 mm diameter blades, vented piston, a segmented rotational shear cell accessory and a 10 or 25 ml borosilicate vessel. Powder testing can be generally divided into three categories: dynamic tests, permeability test and shear test.

Dynamic testing uses the 23.5 mm diameter blades and a 25 ml powder sample in the borosiliate test vessel. Powder is filled into the vessel and the blades are simultaneously rotated and moved axially into the powder sample as the axial and rotational forces are measure and used to calculate the dynamic flowability parameters, such as flow rate index (FRI) and Specific Energy (SE).

As used herein, the "flow rate index" (or FRI) is a measure of a powder's sensitivity to variable flow rate and is obtained as the ratio of the total energy required to induce powder flow at 10 mm/s and 100 mm/s blade tip speed. A larger deviation from 1 indicates greater sensitivity of a powder to variable flow rate.

$$FRI = Flow\ Energy@10_{mm/s}/Flow\ Energy@100_{mm/s}$$

As used herein, "specific energy" or SE is a measure of the powder flow in low stress environment and is derived from the shear forces acting on the blades as they rotate upward through the powder. The SE is recorded as the flow energy of the powder normalized by its weight in mJ/g during the upward spiral movement of the blades in a FT4 Powder Rheometer describe above. A lower SE is an indication of a less cohesive powder and better flow properties.

Shear testing measures powder shear properties which involves the stress limit required to initiate a powder flow. The shear testing uses a segmented rotational shear cell head and a 10 ml powder sample in the borosilicate test vessel. Powder is filled into the vessel. The shear cell head is simultaneously rotated and moved axially under the powder sample at pre-determined normal stresses as the shear stresses are measured to calculate several parameters, including the flow function (FF).

Figure 21:
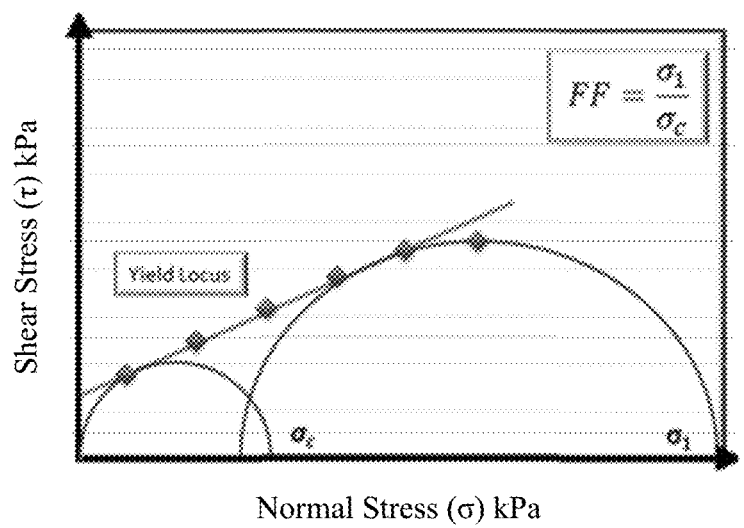
FIG. 21 shows the relationship between shear stress and normal stress, which is plotted to define the powder's Yield Locus.

As used herein, "flow function" or FF is a parameter commonly used to rank powder's flowability and is determined using a shear test. The data produced in the shear test represents the relationship between shear stress and normal stress, which can be plotted to define the powder's Yield Locus, which is shown in FIG. 21. Fitting Mohr stress circles to the yield locus identifies the Major Principle Stress (MPS) and Unconfined Yield Strength (UYS). Flow function is the ratio of Major Principle Stress (MPS) to the Unconfined Yield Strength (UYS):

$$FF = MPS/UYS.$$

Usually, powders of low cohesion have higher FF and that represents better flow properties.

The permeability test measure the ease of air transmission through a bulk powder which can be related to the powder's flowability. The permeability testing uses a vented piston with an aeration base and 10 mL powder sample in the borosilicated test vessel. Powder is filled into the vessel. The powder bed with a vested piston is exposed to varying normal stress increased stepwise from 1 kPa to 15 kPa. The pressure drop across the powder bed is measure while air is flushed through the powder at a constant velocity 2 mm/s.

As used herein, "permeability" is a measure of the powder's resistance to air flow. The permeability test utilizes the vented piston to constrain the powder column under a range of applied normal stresses; while air is passed through the powder column. The relative difference in air pressure between the bottom and the top of the powder column is a function of the powder's permeability. Tests can be carried out under a range of normal stresses and air flow rates. Usually, a lower pressure drop is indicative of higher permeability and often, better flow properties.

As used herein, "aspect ratio" is the ratio of width divided by length of a particle. "Elongation" is defined as 1-aspect ratio. Shapes symmetrical in all axes, such as circles or squares, will tend to have an elongation close to 0, whereas needle-shaped particles will have values closer to 1. Elongation is more an indication of overall form than surface roughness.

As used herein, "convexity" is a measurement of the surface roughness of a particle and is calculated by dividing the perimeter of an imaginary elastic band around the particle by the true perimeter of the particle. A smooth shape, regardless of form, has a convexity of 1 while a very 'spiky' or irregular object has a convexity closer to 0.

As used herein, "circularity" or "high sensitivity circularity" is a measurement of the ratio of the actual perimeter of a particle to the perimeter of a circle of the same area. A perfect circle has a circularity of 1 while a very narrow rod has a High Sensitivity (HS) Circularity close to 0. The higher the HS Circularity value the closer it is to a circle. Intuitively, circularity is a measure of irregularity or the difference from a perfect circle.

As used herein, "enteric coating" refers to a coating that is stable at the highly acidic pH (e.g., pH~3) found in the stomach, but breaks down rapidly at a less acidic pH (e.g., pH 7-9). In certain embodiments, the coating does not dissolve in the stomach for at least 2 hours, 4 hours, 6 hours or longer.

As used herein, "nucleation temperature" refers to the temperature for the initial formation of a crystal from a liquid solution. The nucleation temperature depends on the concentration of the liquid solution.

As used herein, "a" or "an" means one or more unless otherwise specified.

Unless specifically stated or obvious from context, as used herein, the term "about" is understood as within a range of normal tolerance in the art, for example, within 20% of the stated value. As used herein, "about" a specific value also includes the specific value, for example, about 10% includes 10%.

As used herein, the term "DMF," "BG-12," or "BG00012" refers to the compound dimethyl fumarate. And the term "MMF" refers to the compound, or an ionized form of monomethyl fumarate. A compound that can be metabolized into MMF in vivo, as used herein, includes DMF. A compound that can be metabolized into MMF in vivo, as used herein also includes, for example, any compound described in U.S. application Ser. No. 13/760,916, the content of which is incorporated herein by reference in its entirety.

As used herein, the abbreviation API refers to MMF, a compound that can be metabolized into MMF in vivo (e.g., DMF), or a pharmaceutically acceptable salt thereof or combinations thereof. In some embodiments, the API can include more than one compound, for example, a combination of MMF and DMF. In some embodiments, the API is a single compound, e.g., DMF. As used herein, API or DMF can also be referred to as "active ingredient" or "active agent."

Open terms such as "include," "including," "contain," "containing" and the like mean "comprising."

The term "treating" refers to administering a therapy in an amount, manner, or mode effective to improve a condition, symptom, or parameter associated with a disease or disorder.

As used herein, a controlled release dosage form may be any dosage form that is capable of releasing a drug in a body over an extended period of time. The controlled release dosage form herein includes, without limiting to, sustained release dosage form, delayed release dosage form, and pulsatile release dosage form. In some embodiments, the controlled release dosage form herein is gastric retentive, which is retained in the stomach for a period (i.e., the gastric retention time) that is longer than the normal emptying time from the stomach, e.g., longer than about 0.2 hours, following an average meal. In any of the embodiments described herein, the gastric retention time of a gastric retentive controlled release dosage form may be about 0.2 hours to about 18 hours. In some embodiments, a gastric retentive controlled release dosage form is retained in the stomach for about 0.2 hour, about 0.5 hour, about 1 hour, about 2 hours, about 3 hours, about 4 hours, about 6 hours, about 8 hours, about 10 hours, about 12 hours, about 14 hours, about 16 hours, about 18 hours, or any ranges thereof.

The term "microtablet" means a compact in the form of a small (micro) tablet having a mean diameter of less than 5,000 microns (e.g., about 1,000 microns to about 3,000 microns), excluding any coating, that comprises the active ingredient(s) and one or more excipients. The active ingredient(s) and excipients can be homogeneously or heterogeneously mixed in the microtablet. In any of the embodiments described herein, the microtablets may be coated, for example, by a seal coating, an enteric coating, or a combination thereof.

Delivering a drug (e.g., DMF) in a pulsatile manner or in pulses may be understood as involving rapid and transient release of a dose of the drug (e.g., DMF) within a short time period immediately after a lag time.

The term "lag time" as used herein refers to the time between the time of the beginning of delivery of a drug (e.g., DMF) from one component and the subsequent beginning of delivery of the drug (e.g., DMF) from another component. For example, the lag time may refer to the time between the beginning of delivery of the first and second doses of an API upon administering a unit dosage form (e.g., as described herein).

As used herein, a pre-determined lag time of a pulsatile dosage form refers to the lag time that may be determined by in vitro dissolution experiments. For example, for a pulse dosage form containing only one dose of a drug (e.g., DMF), a pre-determined lag time may refer to the time duration between the time when the dosage form is in contact with a gastric liquid or simulations thereof (i.e., the time around when an immediate release dosage form would release the drug) and the time when substantially all of the drug (e.g., DMF) is released from the gastro-retentive dosage form. Alternatively, for dosage forms that contain more than one dose of a drug (e.g., DMF), the pre-determined lag time may refer to the time between releases of any two consecutive doses as determined by in vitro dissolution experiments. The pre-determined lag time herein may be from about 2 hours to about 14 hours. In some embodiments, the pre-determined lag time is about 2 hours, about 4 hours, about 6 hours, about 8 hours, about 10 hours, about 12 hours, about 14 hours, or any ranges thereof. In some embodiments, the pre-determined lag time is about 8 hours to about 12 hours. A pre-determined lag time may be controlled via various techniques. For example, by varying polymer components and/or thickness of lag time control coatings or layers (e.g., pulsatile coatings described herein) in the controlled release dosage forms, different pre-determined lag times can be achieved.

The term "subject" as used herein generally refers to human, including healthy human or a patient with certain diseases or disorders.

As used herein, "an integrated device" is meant for any dosage form having a structure composed of different parts which are united together in one functional and physical whole, to provide, under essentially dry conditions, a structurally stable unified form. A preferred form of an integrated device in accordance with the invention is that wherein the one or more layers are laminated so as to form a laminated device.

As used herein, "laminated" is meant for a device comprising two or more layers/sheets (which may be the same of different), physically of chemically attached/bound together.

Figure 4:
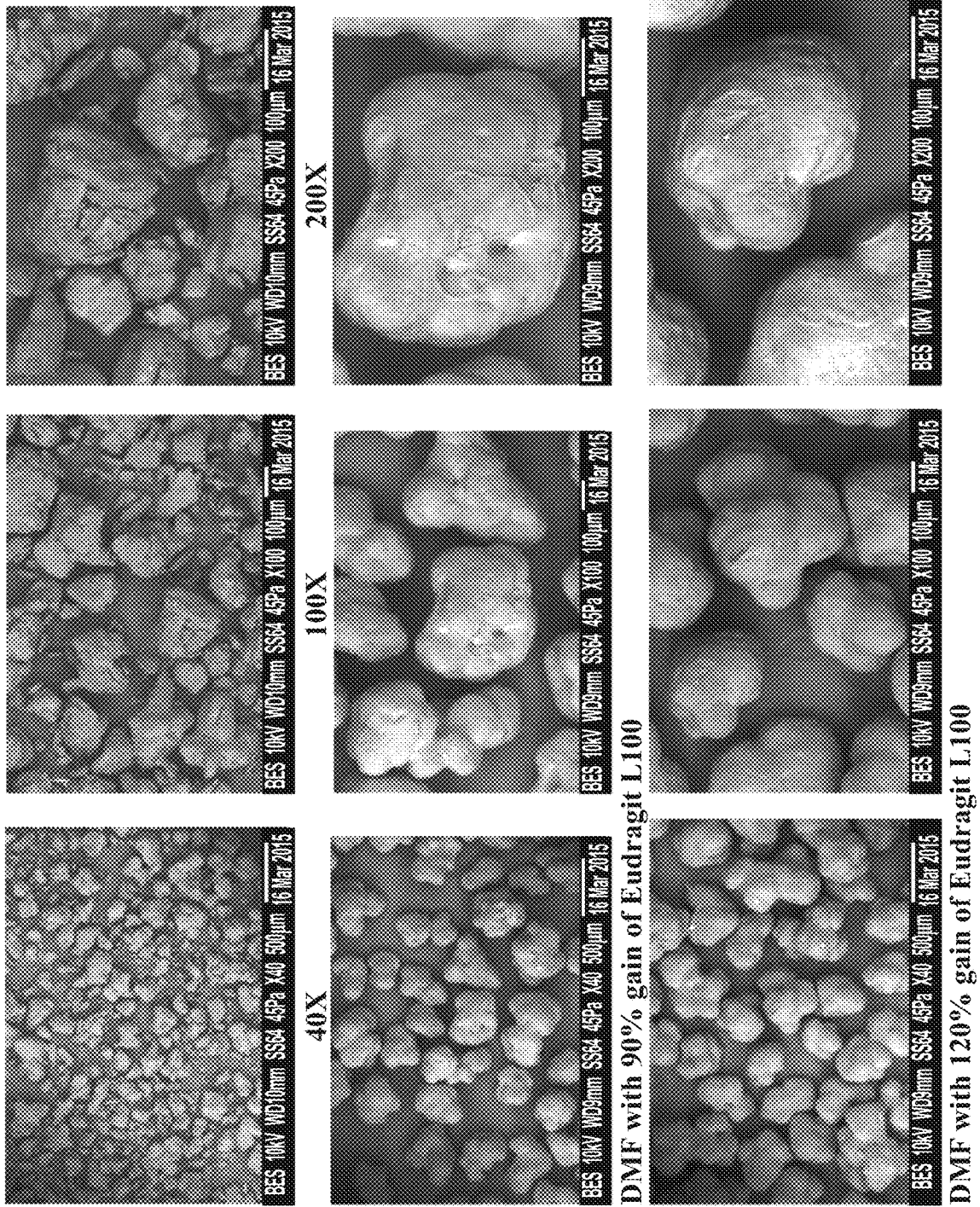
FIG. 4 shows SEM images for uncoated DMF particles and enterically coated DMF particles.

As used herein, "a folded device" is meant for a device that had been manipulated by one or more of folding about fold lines, bending, twisting, wrapping, winding, rolling, crimping and the like. For example, and without being limited thereto, folding may be parallel to the width of the unfolded device and designed to have folds which are symmetric mirror images about a first axis. This manner of folding may provides an accordion-like configuration for an originally essentially planar device; or the folding may be such that the folded device has folds of increasingly smaller amplitudes upon extending away from the first axis so as to form a partially rounded cross section; yet, a further example is of a folds of increasingly larger amplitudes upon extending away from one end of the first axis to its other end, so as to form a fan-like configuration. An example of a folded device is illustrated in FIG. 4.

As used herein, "unfolded" is meant for an essentially and generally planar configuration of the device. The term "essentially planar" or "generally planar" denotes a fully planar as well as wiggly or wavy shape of the device. Unfolding denotes any form of expansion of the device, which may result form unwinding, unrolling, inflating, swelling, and the like. Following expansion in the stomach, the unfolded and essentially planar device maintains its firmness due to its unique characteristics, as exemplified below As used herein, "gastro-retentive" or "gastro-retentivity" is meant the maintenance or withholding of the agent carried by the delivery device in the GI tract (either after being released from or still in association with one or more of the device's compartments/layers), for a time period longer than the time it would have been retained in the stomach when delivered in a free form or within a gastro-intestinal delivery vehicle which is not considered gastro-retentive. Gastro-retentivity may be characterized by retention in the stomach for a period that is longer than the normal emptying time from the stomach, i.e. longer than about 2 hours, following an average meal, particularly longer than about 3 hours and usually more than about 4, 5, 6, 7, 8, 9 or 10 hours. Gastroretentivity typically means retention in the stomach from about 3, 4, 5, 6, 7, 8, 9 or at times 10 hours up to about 18 hours. It is however noted that in accordance with the invention, retention of the gastroretentive delivery device is not observed after more than 48 hours after administration, and preferably not after 24 hours.

As used herein "enclosing" is meant for containing, especially so as to envelop or shelter the device in a container. The container (sometimes termed herein "envelop" or "enclosure") may be, without being limited thereto, a capsule (soft or solid) containing the folded device, an elongated tube, a ring or a thread (one or more) surrounding the folded device, a polymeric coating (e.g. a polymeric thread wrapping the device in a manner resembling a cocoon), a polymer or gel matrix embedding the folded device, enclosing by molding or pressing to a form of a tablet and the like.

As used herein, "a polymer" or "polymeric composition" is meant for a single or combination of polymers exemplified by, but not limited to, degradable polymers, non-degradable polymers, as well as a combination of at least degradable polymer and at least one non-degradable. A polymer may degraded in the stomach or in the intestine either through its solubility, chemical degradation such as hydrolysis of esters or solubilization in the gastric or the intestinal media, or through disintegration that is caused by the mechanical forces applied by the stomach on any solid content, or by a combination of both.

According to one embodiment, the polymer soluble in gastric content comprises one or more polymers selected from a hydrogel-forming polymer, a non-hydrogel polymer, or any combination thereof. Non-limiting examples of hydrogel-forming polymer comprise proteins, polysaccharides, including gums, gelatin, chitosan, polydextrose, cellulose derivatives, such as high molecular weight grades of hydroxypropyl cellulose, hypromelose, hydroxyethyl methyl cellulose, hydroxyethyl cellulose, methyl cellulose, polyethylene oxides, polyvinyl alcohols, soluble derivatives of any one of the above as well as any combination of two or more thereof. Non-limiting examples of non hydrogel polymer comprise povidones (PVP), povidone, and vinyl acetate copolymers (copovidone), methacrylic acid copolymer with dimethyl amino ethyl methacrylate (Eudragit E™), low molecular weight grades of hydroxypropyl cellulose, propylene glycol alginate, polyethylene glycols, poloxamers and soluble derivatives of any one of the above as well as any combination of two or more thereof. These soluble polymers can be further cross-linked, either with use of appropriate chemical cross-linking agent, or by physical cross-linking techniques, or via exposure to gamma radiation, to control their mechanical properties and behavior upon contact with simulated and natural gastric fluid.

According to another embodiment, the polymer may be a water insoluble polymer. A non-limiting list of polymers that are insoluble (non-degradable) comprises any polymer selected from a pharmaceutically acceptable enteric polymer, a pharmaceutically acceptable non-enteric polymer, or any combination thereof. An enteric polymer is preferably such that it is substantially insoluble at a pH of less than 5.5. Non-limiting examples of enteric polymers applicable with respect to the invention include, shellac, cellacefate, hypromelose phthalate, hydroxypropyl methylcellulose acetate succinate, zein, polyvinyl acetate phthalate, aliginic acid and its salts, carboxymethyl cellulose and its salts, methylmethacrylate-methacrylic acid copolymers, including ethyl acrylate copolymers (polymethacrylates), or substantially insoluble (at pH of less than 5.5) derivatives of any one of the above as well as any appropriate combination of two or more of the above. Non-limiting examples of non-enteric polymers applicable with respect to the invention include ethylcellulose; cellulose acetate; a copolymer of acrylic acid and methacrylic acid esters, having of from about 5% to about 10% functional quaternary ammonium groups; a polyethylene; a polyamide; a polyester; polyvinylchloride; polyvinyl acetate; and a combination of any two or more thereof.

The terms "swellable" and "swelling" mean, with respect to a polymer, that the polymer is capable of imbibing fluid and expanding when in contact with fluid present in the environment of use.

1. DMF Particles

In a first aspect, the present invention provides dimethyl fumarate (DMF) particles that have desirable bulk properties and processability for drug product manufacturing.

Dimethyl fumarate (DMF) isolated from the current chemical synthesis needs to undergo a particle size reduction process prior to drug product manufacturing. The coarse dimethyl fumarate, with a typical mean particle size in the range of 500-600 microns, is reduced using a jet milling process. The reduced particles obtained by jet milling process have shown at times poor processability during drug product manufacture due to particle to particle cohesiveness. Larger particles, such as those with a mean particle size of 50 microns or higher, may have improved flow properties. However, larger particles cannot be produced using a jet mill with current jet milling conditions since they are already in the lower end of equipment operating range. Further, changes to milder milling conditions (to obtain larger particles) will result in variability and oversized products. Generally, jet mill is used to reduce particles to under 20 microns.

Dimethyl fumarate also poses peculiar physical properties such as sublimation, low minimum ignition energy (MIE) and sensitizing effects. As such, the handling of this compound requires careful and at times tedious procedures to avoid employee exposures and to ensure process safety (to avoid potential dust explosion).

It is unexpectedly discovered that DMF particles having desirable particle size, bulk properties and processability for drug product manufacturing can be produced using a wet-milling process. The wet-milling process reduces the exposure of DMF dust to employee, providing a safer process.

In one embodiment, the DMF particles of the present invention have a median diameter ($D_{50}$) between 40 μm and 150 μm. In certain embodiments, the $D_{50}$ value for the DMF particles of the present invention is between 50 μm and 130 μm, between 60 μm and 130 μm, between 70 μm and 130 μm, between 50 μm and 100 μm, between 60 μm and 100 μm, between 70 μm and 100 μm, between 80 μm and 100 μm or between 80 μm and 90 μm.

In one embodiment, the DMF particles of the present invention are uniformly distributed. In certain embodiments, the DMF particles of the present invention have a span that is less than 2.0 (e.g., less than 1.9, less than 1.8, less than 1.7, or less than 1.6). In one embodiment, the span for the DMF particles of the present invention is in the range of 1.3 to 1.9, 1.4 to 1.9, or 1.5 to 1.9. In another embodiment, the span is in the range of 1.5 to 1.8. In another embodiment, the span is in the range of 1.3 to 1.7 or 1.3 to 1.8. In yet another embodiment, the span is in the range of 1.3 to 1.5.

In certain embodiments, less than 10% (e.g., less than 9%, less than 8%, less than 7%, less than 6%, etc.) of the DMF particles has a particle size below 10 μm. In another embodiment, less than 5% (e.g., less than 4%, less than 3%, less than 2% or less than 1%) of the DMF particles has a particle size below 5 μm.

In certain embodiments, the DMF particles of the present invention have desirable solid properties suitable for manufacturing process. The DMF particles of the present invention have one or more properties as described below.

In some embodiments, the DMF particles of the present invention have a flow rate index (FRI) that is less than 1.7 (e.g., less than 1.5, less than 1.4, or less than 1.3). In another embodiment, the FRI for the DMF particles of the present invention is less than 1.25, less than 1.20, less than 1.15 or less than 1.10. In one embodiment, the FRI for the DMF particles of the present invention is in the range of 1.0 to 1.7, 1.1 to 1.7, 1.0 to 1.6, 1.0 to 1.5, 1.0 to 1.4, 1.0 to 1.3 or 1.0 to 1.25. In another embodiment, the FRI is the in the range of 1.3 to 1.7.

In some embodiments, the DMF particles of the present invention have a specific energy (SE) that is less than 15.0 (e.g., less than 14.0, less than 13.0, less than 12.0, less than 11.0, less than 10.0, less than 9.0, less than 8.0, less than 7.0, less than 6.0 or less than 5.0). In one embodiment, SE for the DMF particles of the present invention is in the range of 4.0 to 15.0, 4.0 to 14.0, 4.0 to 13.0, 4.0 to 12.0, 4.0 to 11.0, 4.0 to 10.0, 4.0 to 9.0, 4.0 to 8.0, 4.0 to 7.0, 4.0 to 6.8, 4.0 to 6.5, 4.0 to 6.0 or 4.0 to 5.0. In another embodiment, the SE is in the range of 6.0 to 13.0, 6.0 to 13.0 or 10.0 to 13.0.

In some embodiments, the DMF particles of the present invention have a flow function (FF) that is greater than 2.0 (e.g., greater than 3.0, greater than 4.0, greater than 5.0, greater than 6.0, greater than 7.0, greater than 8.0, greater than 9.0 or greater than 10.0). In one embodiment, the flow function for the DMF particles of the present invention is in the range of 2.0 to 20.0, 2.0 to 15.0, 2.0 to 11.0, 2.5 to 15.0, 2.5 to 10.0, 4.0 to 20.0, 8.0 to 20.0, 2.5 to 8.0, 2.5 to 6.0, 4.0 to 10.0, 4.0 to 11.0, or 8.0 to 15.0.

In some embodiments, when subjected to a permeability test at 1 kPa using a FT4 powder rheometer, the pressure drop for the DMF particles of the present invention is less than 0.4 mbar (e.g., less than 0.35 mbar, less than 0.30 mbar, less than 0.25 mbar, less than 0.20 mbar, less than 0.15 mbar or less than 0.10 mbar).

In some embodiments, when subjected to a permeability test at 15 kPa using a FT4 powder rheometer, the pressure drop for the DMF particles of the present invention is less than 0.5 mbar (e.g., less than 0.4 mbar, less than 0.35 mbar, less than 0.3 mbar, less than 0.25 mbar, less than 0.20 mbar, less than 0.15 mbar, or less than 0.1 mbar).

In a $1^{st}$ specific embodiment, the DMF particles of the present invention have a $D_{50}$ value in the range of 50 μm to 100 μm and a span in the range of 1.3 to 1.9.

In a $2^{nd}$ specific embodiment, the DMF particles of the present invention have a $D_{50}$ value in the range of 80 μm to 100 μm and a span in the range of 1.3 to 1.7.

In a $3^{rd}$ specific embodiment, the DMF particles of the present invention (e.g., the DMF particles described in the $1^{st}$ or $2^{nd}$ specific embodiments have the following powder properties:
(i) FRI in the range of 1.0 to 1.7;
(ii) SE in the range of 4.0 to 13.0;
(iii) FF in the range of 2.0 to 11.0;
(iv) pressure drop less than 0.35 mbar when subjected to a permeability test at 1 kPa;
(v) pressure drop less than 0.35 mbar when subjected to a permeability test at 15 kPa.

In a $4^{th}$ specific embodiment, the DMF particles of the present invention (e.g., the DMF particles described in the $1^{st}$ or $2^{nd}$ specific embodiment) have the following powder properties:
(i) FRI in the range of 1.0 to 1.4; and
(ii) FF in the range of 5.0 to 15.0.

In a $5^{th}$ specific embodiment, the DMF particles of the present invention (e.g., the DMF particles described in the $1^{st}$, $2^{nd}$, $3^{rd}$ or $4^{th}$ specific embodiment) have the following powder properties:
(i) pressure drop less than 0.3 mbar when subjected to a permeability test at 1 kPa; and
(ii) pressure drop less than 0.3 mbar when subjected to a permeability test at 15 kPa.

In $6^{th}$ specific embodiment, the DMF particles of the present invention (e.g., the DMF particles described in the $1^{st}$, $2^{nd}$, $3^{rd}$, $4^{th}$ or $5^{th}$ specific embodiment) have a SE in the range of 4.0 to 7.0.

In a $7^{th}$ specific embodiments, the DMF particles of the present invention (e.g., the DMF particles described in the $1^{st}$, $2^{nd}$, $3^{rd}$, $4^{th}$, $5^{th}$ or $6^{th}$ specific embodiment) have a three dimensional morphology.

In one embodiment, the DMF particles of the present invention have higher percentage of thicker particles as compared to the DMF particles prepared by jet-milling process. The percentage of thicker particles can be determined using Malvern Instrument Morphologi G3. Morphologi G3 measures the size and shape of particles by the technique of static image analysis. The intensity of light is quantified by the grey scale factor which depends on the amount of light reaching the detector. The grey scale image of a particle ranges from 0 (black) to 255 (white) and it is related to the thickness of the particle. The lower the intensity value the darker the image therefore the thicker the particle. In certain embodiments, the DMF particles of the present invention have greater than 30%, greater than 40%, greater than 45% or greater than 50% of the particles with intensity less than 80. In one embodiment, 30-100%, 30-90%, 30-80%, 30%-70%, 30-60%, 40-60% or 40-50% of the DMF particles of the present invention have intensity less than 80.

In another embodiment, the DMF particles are slightly less elongated, more circular and less edgy, as indicated by higher aspect ratio, higher HS circularity and higher convexity values, respectively, than the DMF particles prepared by the jet-milling process.

In one embodiment, the DMF particles of the present invention has a circularity value in the rang of 0.8 to 0.95. In another embodiment, 40% of the DMF particles by accumulated volume has a circularity value in the range of 0.8 to 0.9.

In another embodiment, the DMF particles of the present invention has an aspect ratio in the range of 0.55 to 1.0.

In yet another embodiment, the DMF particles of the present invention has a convexity value in the range 0.95 to 1.0.

The three dimensional morphology renders the DMF particles of the present invention more suitable for drug product manufacturing, e.g., coating, mixing, compression, extrusion etc., than DMF particles prepared by the jet-milling process.

The DMF particles of the present invention can be prepared by any suitable processes known in the art. In certain embodiments, the DMF particles of the present invention are prepared by a process described herein.

In one aspect, the present invention provides new processes for preparing the DMF particles of the present invention.

In one embodiment, the process comprises the step of reducing DMF particle size by wet-milling. Wet-milling processes known in the art can be used in the processes of the present invention. According to the present invention, wet-milling can be performed using any kind of mill, e.g., disc mills, colloid mills or other shear mixer. In one embodiment, wet-milling in the processes of the present invention is performed using a high-shear mixer, e.g., an inline high-shear mixer (e.g., Silverson Verso inline mixer or IKA MagicLab inline mixer).

One process of the present invention comprises the step of wet-milling a slurry of DMF particles until desired particle size reduction is achieved.

In a first process, the slurry of DMF can be generated by cooling a solution of DMF to below its nucleation temperature. The solution of DMF can be original reaction mixture of fumaric acid and methanol upon completion of the reaction. The reaction can be carried out in any suitable solvent or any combination of solvents. In one embodiment, methanol is used as solvent. Alternatively, the solution of DMF can be prepared by dissolving coarse DMF in suitable solvent, such as methanol. Generally, the solvent is heated until complete dissolution of coarse DMF. In another alternative, the solution of DMF can be recycled mother liquor from previous wet-milling process.

In certain embodiments, the solution of DMF is a methanol solution and is 80%, 85%, 90%, 95% or 99.9% saturated at the boiling temperature of methanol, i.e., 64°-65°.

In one embodiment, the solution of DMF (e.g., direct reaction mixture in methanol) is cooled to temperature in the range of 60° C.-62° C. to generate a slurry comprising precipitated DMF before starting the wet-milling step.

In one embodiment, the slurry is continuously cooled during the wet-milling step. Generally, the slurry is cooled to a certain temperature to maximize precipitation of DMF. In one embodiment, the slurry is cooled to a temperature in the range of 10°-25° C. More specifically, the slurry is cooled to a temperature in the range of 10°-15° C. Generally, the solution is cooled down slowly. In certain embodiments, the slurry is cooled over a period of 4 to 20 hours, 4 to 15 hours, 4 to 10 hours, or 4 to 8 hours.

Alternatively, in a second process, a slurry comprising DMF is subjected to wet-milling until desired particle size reduction is achieved. The slurry of DMF can by formed by cooling a saturated DMF solution. Alternatively, DMF can be combined with a suitable solvent to provide a slurry comprising DMF. In one embodiment, the solvent is methanol. In another embodiment, DMF in the slurry is DMF crystals.

In a third process, a slurry of DMF is provided at a temperature between 50° C. to below its nucleation temperature. The slurry is then subjected to wet-milling until desired particle size reduction is achieved. Accordingly, in one embodiment, the process of the present invention comprises the steps of:

a) providing a slurry of DMF at a temperature in the range of 50° C. to below its nucleation temperature; and b) wet-milling the slurry until desired particle size reduction is achieved.

The slurry can be prepared by combining DMF with a suitable solvent and heating the solvent-DMF mixture to a temperature below its dissolution temperature or nucleation temperature. In one embodiment, the temperature is in the range of 50° C. to below nucleation temperature. In another embodiment, the slurry of DMF is at a temperature in the range of 60° C.-62° C.

In one embodiment, the wet-milling in step b) is carried out while the slurry is continuously cooled. The slurry is cooled to a certain temperature to maximize precipitation of DMF. In one embodiment, the slurry is cooled to a temperature in the range of 10°-25° C. More specifically, the slurry is cooled to a temperature in the range of 10°-15° C. Generally, the solution is cooled down slowly. In certain embodiments, the slurry is cooled over a period of 4 to 20 hours, 4 to 15 hours, 4 to 10 hours, or 4 to 8 hours.

In certain embodiments, the wet-milling in the processes described above is carried out by recirculating the slurry comprising DMF through a high-shear mixer until the desired particle size reduction is reached. The DMF particle size can be monitored during the wet-milling step.

In certain embodiments, for the processes described above (e.g., the first, second or third process), the process further comprises heating the slurry comprising DMF after the wet-milling step to a temperature below its nucleation temperature followed by cooling the heated slurry. In one embodiment, the slurry is heated to a temperature in the range of 20-50° C. More specifically, the slurry is heated to a temperature in the range of 38-42° C. Alternatively, the slurry is heated to about 28-32° C. In certain embodiments, for the process described above, the slurry is heated at 1° C./minute rate.

In some embodiments, for the process described above, the heated slurry is cooled to a temperature in the range of 0°-15° C., 0°-10° C. or 0°-5° C. In one embodiment, the slurry is cooled at 1° C./minute rate.

In some embodiments, any one of the processes described above further comprises isolating the DMF particles after the wet-milling step.

2. DMF Coated Particles

In a second aspect, the present invention provides dimethyl fumarate (DMF) coated particles, wherein the coated particles comprising DMF starting particles coated with an enteric coating. As used herein, DMF starting particles refer to DMF particles before they are coated with an enteric coating. The DMF coated particles of the present invention are highly stable in gastric fluid, suitable for use in gastro-retentive formulations or dosage forms. In addition, the DMF coated particles have smaller particle size than enterically coated DMF particles known in the art, which makes them suitable to be used in certain gastro-retentive dosage forms described below.

In a $1^{st}$ specific embodiment, the DMF coated particles of the present invention releases no more than 25%, or no more than 20% of the API (e.g., DMF) over 4 to 12 hours when subjected to an in vitro dissolution test employing USP Simulated Gastric Fluid (SGF) without pepsin as dissolution medium. In one embodiment, no more than 19%, 18%, 17%, 16%, 15%, 14%, 13%, 12%, 11%, 10%, 9%, 8%, 7%, 6% or 5% of DMF is released from the DMF coated particles over 4 to 12 hours.

In a $2^{nd}$ specific embodiment, the DMF coated particles of the present invention (e.g., the DMF coated particles descried in the $1^{st}$ specific embodiment) have a particle size less than 500 μm, less than 400 μm, or less than 300 μm. In one embodiment, the DMF coated particles have a particle size in the range of 100 μm to 500 μm, 100 μm to 400 μm, 100 μm to 350 μm, or 130 μm to 350 μm. In another embodiment, the DMF coated particles have a median diameter ($D_{50}$) in the range of 100 μm to 500 μm, 100 μm to 400 μm, 150 μm to 300 μm, 100 μm to 250 μm, 150 μm to 250 μm, or 150 μm to 200 μm.

In a $3^{rd}$ specific embodiment, the DMF coated particles of the present invention (e.g., the DMF coated particles descried in the $1^{st}$ or $2^{nd}$ specific embodiment) are uniformly distributed in size. In one embodiment, the DMF coated particles have a span that is equal to or less than 1.5 (e.g., less than 1.4, less than 1.3, less than 1.2, less than 1.0, less than 0.9, less than 0.8, less than 0.7, less than 0.6, or less than 0.5). In one embodiment, the span for the DMF coated particles of the present invention is in the range of 0.5 to 1.5, 0.5 to 1.2, 0.5 to 1.0, 0.5 to 0.9, 0.5 to 0.8 or 0.6 to 0.8.

In a $4^{th}$ specific embodiment, in the DMF coated particles of the present invention (e.g., the DMF coated particles descried in the $1^{st}$, $2^{nd}$ or $3^{rd}$ specific embodiment), the weight of the enteric coating is greater than 30% of the weight of the DMF starting particles, i.e., greater than 30% weight gain. In one embodiment, the weight of the enteric coating is greater than 40%, 50%, 60%, 70%, 80%, 90%, 110% or 120% of the weight of the DMF starting particles. In one embodiment, the weight of the enteric coating is 30-200%, 50-150%, 60-150%, 70-150%, 80-150%, 80-120% or 90-120% of the DMF starting particles.

Any enteric coating materials known in the art can generally be used in the present invention. In certain embodiments, the enteric coating comprises an excipient selected from the group consisting of a copolymer of methacrylic acid and methyl methacrylate, a copolymer of methacrylic acid and ethyl acrylate, hypromellose phthalate (HPMCP), cellulose acetate phthalate. More specifically, the enteric coating comprises a copolymer of methacrylic acid and methyl methacrylate. Even more specifically, the ratio of methacrylic acid to methyl methacrylate in the copolymer is 0.8:1 to 1.2:1, (e.g., 1:1). In an even more specific embodiment, the enteric coating comprises EUDRAGIT® L 100 (poly(methacylic acid-co-methyl methacrylate) 1:1).

In certain embodiments, the enteric coating of the present invention further comprises one or more plasticizers. Exemplary plasticizers include, but are not limited to, acetyltriethyl citrate, benzyl benzoate, castor oil, chlorobutanol, diacetylated monoglycerides, dibutyl sebacate, diethyl phthalate, glycerin, mannitol, polyethylene glycol, polyethylene glycol monomethyl ether, propylene glycol, pullulan, sorbitol, sorbitol sorbitan solution, triacetin, tributyl citrate, triethyl citrate and Vitamin E. In a more specific embodiment, the plasticizer is triethyl citrate.

In one embodiment, the enteric coating of the present invention comprises EUDRAGIT® L 100 and triethyl citrate. More specifically, the weight ratio of the triethyl citrate to EUDRAGIT® L 100 is from 1:1 to 1:20, from 1:1 to 1:10 or from 1:3 to 1:8. Even more specifically, the weight ratio of the triethyl citrate to EUDRAGIT® L 100 is 1:5.

In a $5^{th}$ specific embodiment, the DMF coated particles of the present invention:

(i) releases no more than 15% of the API (e.g., DMF) over 4 to 12 hours when subjected to an in vitro dissolution test employing USP Simulated Gastric Fluid (SGF) without pepsin as dissolution medium;

(ii) have a median diameter ($D_5O$) in the range of 100 μm to 250 μm with a span in the range of 0.5 to 1.0; and (iii) comprise an enteric coating, wherein the weight of the enteric coating is 80-120% of the weight of the DMF starting particles.

In a $6^{th}$ specific embodiment, for the DMF coated particles described in the $5^{th}$ specific embodiment above, the enteric coating comprises a copolymer of methacrylic acid and methyl methacrylate (e.g., EUDRAGIT® L 100 (poly(methacylic acid-co-methyl methacrylate) 1:1). In a more specific embodiment, the enteric coating further comprises a plasticizer. Even more specifically, the plasticizer is triethyl citrate. In another more specific embodiment, the enteric coating comprises EUDRAGIT® L 100 and triethyl citrate, wherein the weigh ratio of the triethyl citrate to EUDRAGIT® L 100 is 1:5.

In certain embodiments, the DMF starting particles in the DMF coated particles of the present invention (e.g., DMF coated particles described in the second aspect of the invention or the $1^{st}$, $2^{nd}$, $3^{rd}$, $4^{th}$, $5^{th}$ or $6^{th}$ specific embodiment or any more specific embodiments described therein) are the DMF particles described in the first aspect of the invention (e.g. the DMF particles described in the $1^{st}$, $2^{nd}$, $3^{rd}$, $4^{th}$, $5^{th}$, $6^{th}$ or $7^{th}$ specific embodiment or any more specific embodiments described therein).

3. Dosage Forms

The present invention provides dosage forms comprising DMF coated particles described in the second aspect of invention or any specific embodiments described therein.

In certain embodiments, the dosage forms (e.g. unit dosage form) of the present invention are suitable for once a day dosing. The dosage forms (e.g. unit dosage form) of the present invention are also believe to have improved DMF absorption.

A. Controlled Release Dosage Form

In a third aspect, the present invention provides controlled release dosage forms comprising the DMF coated particles described above in the second aspect of invention or any embodiments described therein.

In various embodiments, the invention provides a controlled release dosage form that releases MMF, a compound that can be metabolized into MMF in vivo (e.g., DMF), or a pharmaceutically acceptable salt thereof or combinations thereof (collectively "API"), in the gastrointestinal ("GI") tract of a subject in a sustained or pulsatile manner. In some embodiments, the API in the controlled release dosage form is retained in the stomach and/or small intestine of a subject treated for at least 3 hours (e.g., about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, or any ranges thereof). In some embodiments, the API in the controlled release dosage form is retained in the stomach and/or small intestine for about 3 hours to about 17 hours. In some embodiments, the API in the controlled release dosage form is retained in the stomach and/or small intestine of a subject treated for at least 4 hours, at least 5 hours, at least 6 hours, at least 7 hours, or at least 8 hours. In some embodiments, the API in the controlled release dosage form is retained in the stomach and/or small intestine of a subject treated for at least 5 hours, at least 6 hours, or at least 7 hours.

The controlled release dosage form can be a matrix dosage form, an osmotic dosage form, a gastric retention dosage form, an intestinal retention dosage form, or a combination thereof.

In some embodiments, a daily amount of the API (e.g., 480 mg of DMF) is provided by one or more units of the controlled release dosage system alone. In some embodiments, the daily amount of the API is provided by one or more units of the controlled release dosage form in combination with one or more units of an enterically coated immediate release dosage form.

In some embodiments, a subject administered one or more units (e.g., 1, 2, 3, 4, 5, or 6) of the controlled release dosage form (with or without food) once daily produces one or more of the following pharmacokinetic parameters in the subject: (a) a mean plasma MMF $AUC_{overall}$ ranging from about 4.81 h·mg/L to about 11.2 h·mg/L; (b) a mean plasma MMF $AUC_{0-12}$ ranging from about 2.4 h·mg/L to about 5.5 h·mg/L; and (c) a mean $AUC_{0-infinity}$ ranging from about 2.4 h·mg/L to about 5.6 h·mg/L. In some embodiments, the subject treated exhibits a pharmacokinetic profile characterized by both (a) and (b), both (a) and (c), or both (b) and (c). In some embodiments, the subject treated exhibits a pharmacokinetic profile characterized by (a), (b), and (c).

In some embodiments, a subject administered a single unit of the controlled release dosage form (with or without food) or a unit dosage form described herein once daily produces one or more of the following pharmacokinetic parameters in the subject: (a) a mean plasma MMF $AUC_{overall}$ ranging from about 4.81 h·mg/L to about 11.2 h·mg/L; (b) a mean plasma MMF $AUC_{0-12}$ ranging from about 2.4 h·mg/L to about 5.5 h·mg/L; and (c) a mean $AUC_{0-infinity}$ ranging from about 2.4 h·mg/L to about 5.6 h·mg/L. In some embodiments, the subject treated exhibits a pharmacokinetic profile characterized by both (a) and (b), both (a) and (c), or both (b) and (c). In some embodiments, the subject treated exhibits a pharmacokinetic profile characterized by (a), (b), and (c).

In some embodiments, a subject orally administered a single unit of the controlled release dosage form or a unit dosage form described herein (with or without food) once daily exhibits a mean MMF plasma area under the curve 0-12 ($AUC_{0-12}$) of about 2.36 h·mg/L to about 5.50 h·mg/L, from about 2.75 h·mg/L to about 5.10 h·mg/L, or from about 3.14 h·mg/L to about 4.91 h·mg/L. In one embodiment, the subject exhibits a mean $AUC_{0-12}$ of about 3.93 h·mg/L.

In some embodiments, a subject orally administered a single unit of the controlled release dosage form or a unit dosage form described herein (with or without food) once daily exhibits a mean MMF plasma overall area under the curve ($AUC_{overall}$) of about 4.81 h·mg/mL to about 11.2 h·mg/mL, or from about 6.40 h·mg/L to about 10.1 h·mg/L. In one embodiment, the subject exhibits a mean $AUC_{overall}$ of about 8.02 h·mg/L.

In some embodiments, suitable amounts of API for the controlled release dosage form include those that can provide, by itself or in combination with one or more doses from, for example, a second dosage form (e.g., a controlled release dosage form or an enterically coated immediate release dosage form), a daily amount of the respective compound (e.g., DMF) ranging from about 1 mg/kg to about 50 mg/kg (e.g., from about 2.5 mg/kg to about 20 mg/kg or from about 2.5 mg/kg to about 15 mg/kg).

The controlled release dosage form contains any therapeutically effective dose of an API, e.g., an amount that is effective in treating multiple sclerosis. For example, suitable doses of DMF in the controlled release dosage form may be any dose from about 20 mg to about 1 g of DMF. In some embodiments, the suitable doses of DMF in the controlled release dosage form may be any dose from about 80 mg to about 1000 mg of DMF. In some embodiments, the suitable doses of DMF in the controlled release dosage form may be any dose from about 100 mg to about 750 mg of DMF. In some embodiments, the suitable doses of DMF in the controlled release dosage form is about 200 to about 600 mg. In some embodiments, the suitable doses of DMF in the controlled release dosage form may be any dose from about 300 to about 600 mg. In some embodiments, the suitable doses of DMF in the controlled release dosage form is about 480 mg.

In some embodiments, the DMF in the controlled release dosage form is about 60 mg, about 80 mg, about 100 mg, about 120 mg, about 160 mg, about 200 mg, about 240 mg, about 320 mg, about 360 mg, about 400 mg, about 480 mg, about 600 mg, about 720 mg, about 800 mg, about 900 mg, about 1000 mg of DMF, or any ranges thereof.

The controlled release dosage form can contain an amount of a compound that that can metabolize into MMF that provides an equivalent amount of MMF as the doses of DMF described above.

In some embodiments, the daily amount of the API is provided by one or more units (e.g., 1, 2, 3, 4, or 5) of the controlled release dosage form herein. In some embodiments, the daily amount of the API is provided by a single unit of the controlled release dosage form herein, i.e., one unit per day. In some embodiments, one or more units (e.g., 1, 2, 3, 4, or 5) of the controlled release dosage form herein is co-administered with one or more units (e.g., 1, 2, 3, 4, or 5) of a second dosage form (e.g., as described herein) to provide the daily amount of the API to a subject. In some embodiments, the daily amount of the API is provided by one or more units (e.g., 1, 2, 3, 4, or 5) of the controlled release dosage form described herein and one or more units (e.g., 1, 2, 3, 4, or 5) of an enterically coated immediate release dosage form (e.g., as described herein). For example, in some embodiments, two units of the controlled release dosage form (e.g., two of the osmotic dosage form described herein) and one enterically coated immediate release dosage form is combined, for example, in a capsule, or a tablet, to provide the daily amount of the API (e.g., DMF) to a subject.

In some embodiments, the controlled release dosage form comprises an acid soluble outer coating. Suitable acid soluble coatings for the first dosage component are known in the art and include those coatings that dissolve at a pH less than 6.0. Non-limiting examples of acid soluble coatings include gelatin, Eudragit® E-100, polyvinyl acetyl diethylaminoacetate, and chitosan coatings. The acid-soluble coating may be applied using various techniques (e.g., spray techniques) known to one skilled in the art.

In addition to the components listed below for each controlled release dosage form, the controlled release dosage form may also comprise one or more pharmaceutically acceptable excipients in addition to those described above. Suitable pharmaceutically acceptable excipients are those known in the art, for example, binders, fillers, disintegrants, glidants, lubricants, diluents, plasticizers, etc. as described in Remington's Pharmaceutical Science, $18^{th}$ Edition, 1990, Mack Publishing Company, Easton, Pa. ("Remington's").

a. Matrix Dosage Form

In some embodiments, the invention provides a matrix dosage form for delivering an API to a subject treated. The matrix dosage form herein comprises a core comprising an API (e.g., DMF coated particles described above in the second aspect or any embodiments described therein), one or more release modifying polymers, and one or more pharmaceutically acceptable excipients. Suitable release modifying polymers for a matrix dosage form include cellulose and cellulose derivatives, such as microcrystalline cellulose, hydroxypropyl methyl cellulose, hydroxypropyl cellulose and methylcellulose, Eudragit polymers (e.g., Eudragit RS, RL), povidone, polyvinyl acetate, poly(ethyleneoxide) (PEO), polyethylene glycol (PEG), poly (vinyl alcohol) (PVA), xanthan gum, carrageenan and other synthetic materials. The amount of the release modifying polymers can be from about 2% to about 50% by weight of the matrix dosage form. In some embodiments, the amount of the release modifying polymers can be about 2%, about 5%, about 10%, about 15%, about 20%, about 25%, about 30%, about 35%, about 40%, about 45%, about 50%, or any ranges thereof, by weight of the matrix dosage form. Various techniques for preparing a matrix dosage form are known.

The matrix dosage form herein may also be coated. In some embodiments, the matrix dosage form comprises a seal coating encapsulating the core. In some embodiments, the matrix dosage form comprises an outer enteric coating. In some embodiments, the outer enteric coating encapsulates a seal coating. Various techniques for coating are known.

In some embodiments, the matrix dosage form exhibits zero-order release of the API. In some embodiments, the matrix dosage form releases the API in the GI tract of a subject in a sustained period of time from about 2 to about 24 hours (e.g., about 2, about 4, about 6, about 8, about 10, about 12, about 14, about 16, about 18, about 20, about 22, about 24 hours, or any ranges thereof). In some embodiments, the matrix dosage form releases the API in the GI tract of a subject in about 2 to about 10 hours. In some embodiments, the matrix dosage form releases the API in the GI tract of a subject in about 4 to about 6 hours. In some embodiments, the API is released in the stomach. In some embodiments, the API is released in the upper GI tract. In some embodiments, the API is released in the lower GI tract. In some embodiments, the API is released in the small intestine.

The rate of release can be modified by varying the amount, type, and ratio of the one or more release modifying polymers.

The rate of release can also depend on the form (e.g., tablet or microtablets) of the matrix dosage form. In some embodiments, the matrix dosage form comprising the API is a bilayer or monolithic tablet. In some embodiments, the matrix dosage form comprises a plurality of microtablets comprising the API. In some embodiments, the bilayer or monolithic tablet, or the microtablets are coated (e.g., enterically coated).

The release profile of the matrix dosage form herein can be determined by an in vitro dissolution method. Standard test protocols for in vitro dissolution are known. In some embodiments, the release profile of the matrix dosage form is characterized in that more than about 80% of the API is released in less than about 8 hours (e.g., about 6 hours, about 4 hours), when tested by United State Pharmacopoeia (USP) Dissolution Apparatus 2 according to standardized and specified in USP General Chapter <711> Dissolution, at an agitation speed of 75 rpm. In some embodiments, the release profile of the matrix dosage form is characterized in that more than about 80% of the API is released in less than about 8 hours (e.g., about 6 hours, about 4 hours), when tested by United State Pharmacopoeia (USP) Dissolution Apparatus 2 according to standardized and specified in USP General Chapter <711> Dissolution, at an agitation speed of 100 rpm.

b. Osmotic Dosage Form

In any of the embodiments described herein, the controlled release dosage form is an osmotic dosage form. Various techniques for preparing an osmotic dosage form that include, but are not limited to monolithic tablets, bilayer tablets, and trilayer tablets, are known. In some aspects, the osmotic dosage form comprises an osmotic monolithic tablet.

An osmotic dosage form can be a tablet with a semi-permeable membrane. The semi-permeable membrane allows water into the tablet which dissolves an osmotic agent that creates osmotic pressure and/or a hydrophilic polymer that suspends and carries the drug out of the coated tablet through a laser drilled hole in the coating.

The osmotic dosage form herein can include an osmotic core comprising an API (e.g., DMF coated particles described above in the second aspect or any embodiments described therein), one or more osmotic agents, one or more pharmaceutically acceptable excipients, and optionally one or more release modifying polymers. In some embodiments, the semi-permeable membrane coated tablets could be encapsulated in a gelatin capsule. Suitable material for the semi-permeable membrane coatings includes those known in the art, for example, cellulose products such as cellulose acetate, ethyl cellulose, hydroxyalkyl cellulose (e.g., hydroxypropyl cellulose, hydroxypropyl methyl cellulose, hydroxyethyl cellulose). Suitable osmotic agents include those known in the art, for example, a sugar such as sorbitol, mannitol, xylitol, fructose or salts (e.g. sodium chloride). In some embodiments, the osmotic agents can be in an amount of about 10%, about 20%, about 30%, about 40%, about 50%, about 60%, or any ranges thereof, by weight of total weight of the osmotic dosage form. In some embodiments, the semi-permeable membrane coatings can be in an amount of about 2% to about 20% (e.g., about 2%, about 5%, about 10%, about 15%, about 20%, or any ranges thereof) by weight of total weight of the osmotic dosage form.

Other suitable material for the osmotic dosage form include those known in the art, for example, the osmotic dosage form may comprise a water swellable polymer (e.g. polyethylene oxide), a water soluble polymer, a water insoluble polymer (e.g. sodium carboxyl methyl cellulose), a water insoluble and water swellable polymer, a water insoluble and water permeable polymer, or combinations thereof.

In some embodiments, the osmotic dosage form comprises a polymer selected from the group consisting of homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, methylcellulose, ethylcellulose, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan or xanthan gum polyethylene oxide, and hydroxypropyl methylcellulose.

In some embodiments, the osmotic dosage form comprises a polymer selected from the group consisting of hydroxypropylcellulose, cross-linked polyvinylpyrrolidone, cross-linked carboxymethylcellulose, pregelatinized starch, sodium starch glycolate, polyvinyl acetate, polyacrylic acid, acrylate-co-polymer, carboxymethylcellulose calcium, carboxymethylcellulose sodium, poly(hydroxyethyl-methacrylate), poly(methacrylic acid), poly(acrylamide), sodium starch glycolate, starch, poly(hydroxyalkyl methacrylate) with a molecular weight of 32,000 to 5,500,000, poly(electrolyte) complexes. poly(vinyl alcohol), acrylate polymers with water absorbability of roughly 400 times its original weight, a mixture of poly(vinyl alcohol) and poly(N-vinyl-2-pyrrolidone), poly(acrylic acid) with a molecular weight of 80,000 to 200,000, polyoxy polyethylene oxide polymers with a molecular weight of 100,000 to 5,000,000, polysaccharides, agar, acacia, karaya, tragacanth and algins, pectin with a molecular weight of 30,000 to 300,000, and polyoxybutylenepolyethylene block polymer.

In some embodiments, the osmotic dosage form comprises a polymer selected from the group consisting of cellulose acylate, cellulose acetate, cellulose diacylate, cellulose diacetate, cellulose triacylate, cellulose triacetate, mono-, di-, and tri-cellulose alkanylate, mono-, di- and tri-alkenylates, mono-, di- and tri-aroylates, cellulose trivalerate, cellulose trilaurate, cellulose tripalmitate, cellulose trioctanoate, cellulose tripropionate, cellulose diesters, cellulose disuccinate, cellulose dipalmitate, cellulose dioctanoate, cellulose dicarpylate, cellulose actate heptonate, cellulose valerate palmitate, cellulose acetate octonoate, cellulose propionate succinate, cellulose acetate valerate, cellulose acetaldehyde, dimethyl cellulose acetate, cellulose acetate ethylcarbamate, hydroxypropylmethylcellulose, semipermeable polyamylsulfanes, semipermeable urethane, cellulose acetate methylcarbamate, cellulose dimethylaminoacetate, semipermeable sulfonated polystyrenes, semipermeable silicone rubbers, semipermeable styrenes, sulfonated polystyrenes, polyurethanes, polydiethylaminomethylstyrene, cellulose acetate methylcarbamate, ethylcellulose, shellac, polymethylstyrene, polyvinylacetate, seimpermeble (polysodium styrenesulfonate), and semipermeable poly(vinylbenzymtrimethylammonium chloride.

In some embodiments, the osmotic dosage form comprises a polyethylene oxide or hydroxypropyl methylcellulose. Various commercially available polyethylene oxide (e.g., Polyox N-80, WSR N-750 or WSR-205) and hydroxypropyl methylcellulose (e.g., Methocel K 100 Premium LV or E50 Premium LV) are suitable for use in the osmotic dosage form.

In some embodiments, the osmotic dosage form releases the API and exhibits zero-order release of the API. In some embodiments, the osmotic dosage form releases the API in the GI tract of a subject in a sustained period of time from about 2 to about 24 hours (e.g., about 2, about 4, about 6, about 8, about 10, about 12, about 14, about 16, about 18, about 20, about 22, about 24 hours, or any ranges thereof). In some embodiments, the osmotic dosage form releases the API in the GI tract of a subject in about 2 to about 10 hours. In some embodiments, the osmotic dosage form releases the API in the GI tract of a subject in about 4 to about 6 hours. In some embodiments, the API is released in the stomach. In some embodiments, the API is released in the upper GI tract. In some embodiments, the API is released in the lower GI tract. In some embodiments, the API is released in the small intestine.

The release profile of the osmotic dosage form herein can also be determined by an in vitro dissolution method. Standard test protocols for in vitro dissolution are known. In some embodiments, the release profile of the osmotic dosage form is characterized in that more than about 80% of the API is released in less than about 8 hours (e.g., about 6 hours, about 4 hours), when tested by USP Dissolution Apparatus 2 according to standardized and specified in USP General Chapter <711> Dissolution, at 75 rpm. In some embodiments, the release profile of the matrix dosage form is characterized in that more than about 80% of the API is released in less than about 8 hours (e.g., about 6 hours, about 4 hours), when tested by USP Dissolution Apparatus 2 according to standardized and specified procedures in USP General Chapter <711> Dissolution, at 100 rpm.

c. Gastric Retention Dosage Form

In some embodiments, the invention provides a gastric retention dosage form for delivering an API to a subject treated. In some embodiments, the gastric retention dosage form releases the API in the GI tract of a subject in a sustained period of time (e.g., about 2, about 4, about 6, about 8, about 10, about 12, about 14, about 16, about 18, about 20, about 22, or about 24 hours). In some aspects, the gastric retention dosage form, by itself or in combination with a second dosage form (enterically coated immediate release or delayed release), releases the API in the GI tract of a subject in a pulsatile manner with a lag time from about 2 hours to about 14 hours (e.g., about 2 hours, about 4 hours, about 6 hours, about 8 hours, about 10 hours, about 12 hours, about 14 hours, or any ranges thereof).

In some embodiments, the gastric retention dosage form is retained in the stomach of a subject treated, for example, has a gastric retention time of from about 0.2 hour to about 18 hours (e.g., about 0.2 hour, about 0.5 hour, about 1 hour, about 2 hours, about 3 hours, about 4 hours, about 6 hours, about 8 hours, about 10 hours, about 12 hours, about 14 hours, about 16 hours, about 18 hours, or any ranges thereof). In some embodiments, the API in the gastric retention dosage form is retained in the stomach of a subject treated, for example, for about 0.2 hour to about 18 hours (e.g., about 0.2 hour, about 0.5 hour, about 1 hour, about 2 hours, about 3 hours, about 4 hours, about 6 hours, about 8 hours, about 10 hours, about 12 hours, about 14 hours, about 16 hours, about 18 hours, or any ranges thereof). In some embodiments, the API in the gastric retention dosage form is retained in the stomach of a subject treated for at least 3 hours (e.g., about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, or any ranges thereof). In some embodiments, the API in the gastric retention dosage form is retained in the stomach of a subject treated for about 3 hours to about 17 hours. In some embodiments, the API in the gastric retention dosage form is retained in the stomach of a subject treated for at least 4 hours, at least 5 hours, at least 6 hours, at least 7 hours, or at least 8 hours. In some embodiments, the API in the gastric retention dosage form is retained in the stomach of a subject treated for at least 5 hours, at least 6 hours, or at least 7 hours. Various means to achieve gastric retention are known. For example, in some embodiments, the gastric retention dosage form is a floating dosage form or a swelling dosage form.

Floating Dosage Form

In some embodiments, the controlled release dosage form is a floating dosage form that floats when exposed to gastric fluid and thereby retaining the API in the stomach of a subject treated. Various techniques for preparing a floating dosage form are known. In some embodiments, the floating dosage form is a floating tablet (e.g., a bilayer or a trilayer tablet) or a floating capsule.

The floating dosage form described herein can include an active layer and a floating layer, wherein the active layer comprises an API (e.g., DMF coated particles described above in the second aspect or any embodiments described therein) and one or more release modifying polymers. In some embodiments, the gastric retention time of the floating dosage form is from about 0.2 hour to about 18 hours (e.g., about 0.2 hour, about 0.5 hour, about 1 hour, about 2 hours, about 3 hours, about 4 hours, about 6 hours, about 8 hours, about 10 hours, about 12 hours, about 14 hours, about 16 hours, about 18 hours, or any ranges thereof). In some embodiments, the floating dosage form floats in the stomach until the active layer releases all the API (e.g., DMF coated particles described above in the second aspect or any embodiments described therein). In some embodiments, the floating dosage form floats in the stomach before the active layer releases all the API (e.g., DMF coated particles described above in the second aspect or any embodiments described therein). The gastric retention time of the floating dosage form can be controlled by adjusting the floating layer, for example, by adjusting the amount of gas that can be generated and the speed of gas generation. Other techniques for adjusting the gastric retention time are known.

Materials suitable for the floating layer include pharmaceutical excipients that can lower the density of the pharmaceutical composition. In some embodiments, the floating layer comprises one or more low density excipients selected from the group consisting of hydroxypropyl methylcellulose, hydrogenated castor oil, carboxymethylcellulose, ethylcellulose, cross-linked povidone, chitosan and combinations thereof. In some embodiments, the weight ratio for the one or more low density excipients are adjusted such that the density of the floating dosage form is lower than the density of the gastric fluid in a subject.

In some embodiments, the floating layer comprises a porous mineral material, such as calcium silicate. In some embodiments, the porous mineral material having air entrapped within are coated with a polymer (e.g., hydroxypropylcellulose or ethylcellulose) such that the air within the porous mineral material is retained. In some embodiments, the floating layer comprises a porous mineral material that further comprises one or more low density excipients as described herein.

In some embodiments, the floating layer comprises hollow microspheres or polycarbonate resin that floats in a gastric fluid of a subject.

In some embodiments, the floating layer comprises a gas-generating system. Suitable gas-generating systems are known in the art. In some embodiments, the floating layer comprises at least one gas-generating system (e.g., a carbon-dioxide generating system, e.g., comprises an alkali or alkaline earth metal carbonate or bicarbonate) and at least one hydrophilic polymer (e.g., polysaccharide substances, protein substances, poloxamers, high molecular weight polyethylene glycols, polymers of methacrylic acids, polymers of acrylic acids, derivatives of methacrylic acid, or derivatives of acrylic acid), a cellulose polymer such as hydroxyalkyl alkylcellulose (e.g., hydroxypropyl methylcellulose), or a porous mineral compound (e.g., a silica or silica derivative). In some embodiments, the floating layer comprises sodium carbonate and Methocel K100M. In some embodiments, the weight ratio of sodium carbonate to Methocel K100M is from about 1:50 to about 50:1 (e.g., about 1:1 to about 1:10, about 1:2 to about 1:5, or about 1:3). In some embodiment, the floating layer comprises an effervescent couple, wherein upon oral administration of the controlled release dosage form to a subject, the effervescent couple in the floating dosage form generates gas and causes the gastric retention dosage form to float in the gastric liquid of the subject.

The floating dosage form described herein can take various forms. For example, in some embodiments, the floating dosage form is a bilayer or a trilayer tablet, wherein the floating layer and the active layer are compressed or otherwise joined to form a tablet structure. In some embodiments, the floating dosage form is a double tablet structure, wherein the floating layer encapsulates the active layer. In some embodiments, the floating dosage form is a capsule (e.g., a soft gel or hard gel capsule) encapsulating the floating layer and the active layer. In some embodiments, the capsule is partially coated with acid insoluble polymer.

The floating dosage form described herein can be a sustained release dosage form or a delayed release dosage form depending on the configuration of the active layer.

In some embodiments, the floating dosage form can be a sustained release dosage form. For example, in some embodiments, the active layer is a matrix dosage form described herein or an osmotic dosage form described herein.

The floating dosage form can also be a delayed release dosage form. For example, in some embodiments, the active layer is a delayed release dosage form, which, when administered together with a second dosage form (e.g., an enterically coated immediate release dosage form, or a delayed release dosage form), provides a pulsatile release of the API with a lag time from about 2 hours to about 14 hours (e.g., about 2 hours, about 4 hours, about 6 hours, about 8 hours, about 10 hours, about 12 hours, about 14 hours, or any ranges thereof). Suitable methods for preparing a delayed release dosage form comprising an API (e.g., coated API) include those known. In some embodiments, the delayed release dosage form may contain an enterically coated active layer and/or an enterically coated API. In some embodiments, the delayed release dosage form comprises about 90% by weight of a coated API (e.g., coated DMF particles) and about 10% by weight of a cellulose polymer (e.g., hydroxypropyl methylcellulose, Methocel E3 LV). In some embodiments, the delayed release dosage form may contain a core comprising an API, an inner seal coating, followed by a semipermeable coating. In some embodiments, the delayed release dosage form may further comprise an outer enteric coating. See examples in Example 1.

More than one active layers and/or more than one floating layers can also be included in the floating dosage form described herein. In some embodiments, the floating dosage form comprises two floating layers. In some embodiments, the active layer is placed between the two floating layers. In any of the embodiments described herein, wherein the floating dosage form comprises three layers (e.g., two active layers one floating layer, or two floating layers one active layer), the floating dosage form may be a trilayer tablet or a capsule encompassing the three layers.

In some embodiments, the floating dosage form comprises a second active layer. In some embodiments, the second active layer is an enterically coated immediate release dosage component, provided that the enterically coated immediate release dosage component is not placed between the active layer and the floating layer in a trilayer tablet structure. In some embodiments, the floating dosage form comprises both a sustained release dosage component and an enterically coated immediate release dosage component. In some embodiments, the floating dosage form comprises both a delayed release dosage component and an enterically coated immediate release dosage component, wherein when administered, the floating dosage form provides a pulsatile release of the API with a lag time from about 2 hours to about 14 hours.

Swellable Dosage Form

In any of the embodiments described herein, the controlled release dosage form is a dosage form that swells when exposed to gastric fluid and thereby retaining the API (e.g., DMF coated particles described above in the second aspect or any embodiments described therein) in the stomach of a subject treated. Various techniques for preparing a swellable dosage form are known. For example, U.S. Pat. Nos. 5,972,389 and 6,723,340 B2, incorporated by reference herein, disclose a swellable dosage form that can be utilized in the embodiments disclosed herein.

The swelling dosage form described herein can include an API (e.g., DMF coated particles described above in the second aspect or any embodiments described therein) and one or more swelling polymer. Suitable swelling polymers include those known in the art, for example, polyethylene oxide (e.g., Polyox 205-NF) and/or hydroxyalkyl alkylcellulose (e.g., hydroxypropyl methyl cellulose, e.g., Methocel K4M, K100M) may be used. In some embodiments, the one or more swelling polymers are a combination of poly(ethylene oxide) and hydroxypropyl methylcellulose in various weight ratios (e.g., from about 10:1 to about 1:10).

In some embodiments, the swelling dosage form is a swelling tablet (e.g., a monolithic, bilayer, or trilayer tablet) or a swelling sheet (e.g., an Accordion Pill™, in which an API, optionally coated, is embedded in one section of the swellable polymer sheets). In some embodiments, the swelling dosage form is a monolithic tablet comprising an active layer comprising an API (e.g., DMF coated particles described above in the second aspect or any embodiments described therein) and a swelling layer. In some embodiments, the swelling layer encapsulates the active layer. In some embodiments, the swelling dosage form is a bilayer tablet comprising an active layer comprising an API (e.g., DMF coated particles described above in the second aspect or any embodiments described therein) and a swelling layer. In some embodiments, more than one active layer are present in the swelling dosage form. In some embodiments, more than one swelling layer are present in the swelling dosage form.

The swellable dosage form herein may be a sustained release or delayed release dosage form.

In some embodiments, the swelling dosage form is a sustained release dosage form. In some embodiments, the API together with the swelling polymer form a swellable matrix. In some embodiments, the API is coated (e.g., seal coated, enterically coated, or a combination thereof). In some embodiments, the API in the swellable dosage form may be in an amount of about 20%, about 30%, about 40%, about 50%, about 60%, about 70%, about 80%, or any ranges thereof, by weight of total weight of the swellable dosage form. The one or more swelling polymers in the swellable dosage form may be in an amount of about 10%, about 15%, about 20%, about 25%, about 30%, about 35%, about 40%, about 45%, about 50%, or any ranges thereof, by weight of total weight of the swellable dosage form. The swellable dosage form may also include pharmaceutical excipients in an amount of about 0.1%, about 0.5%, about 1%, about 2%, about 5%, about 10%, or any ranges thereof, by weight of total weight of the swellable dosage form. For example, the swellable dosage form may be composed of about 60% coated DMF; about 24% Polyox 205-NF (PEO); about 15% Methocel K4M (HPMC); and about 1% magnesium stearate.

In some embodiments, the swellable matrix releases the API in a sustained manner over a period of from about 2 to about 24 hours (e.g., about 2 hours, about 4 hours, about 6 hours, about 8 hours, about 10 hours, about 12 hours, about 14 hours, about 16 hours, about 18 hours, about 20 hours, about 22 hours, about 24 hours, or any ranges thereof). In some embodiments, the swellable matrix exhibits zero-order release of the API.

In some embodiments, the swelling dosage form is a delayed release dosage form, which, when administered together with a second dosage form (e.g., an enterically coated immediate release dosage form, or a delayed release dosage form), provides a pulsatile release of the API with a lag time from about 2 hours to about 14 hours (e.g., about 2 hours, about 4 hours, about 6 hours, about 8 hours, about 10 hours, about 12 hours, about 14 hours, or any ranges thereof). In some embodiments, the swellable pulsatile release dosage form comprises one or more swelling polymers and an API. In some embodiments, the API is coated (e.g., seal coated, enterically coated, or a combination thereof). Suitable swellable polymers are described above.

In some embodiments, the swelling dosage form comprises both a delayed release dosage component and an enterically coated immediate release dosage component, wherein when administered, the swelling dosage form provides a pulsatile release of the API with a lag time from about 2 hours to about 14 hours.

Folded Dosage Form

In certain embodiments, the controlled release dosage forms of the present invention are folded dosage forms as those described in U.S. Pat. Nos. 6,685,962, 8,609,136 and 8,771,730, the entire teaching of which is incorporated herein by reference.

In a first embodiment, the folded dosage form of the present invention is a folded device configured for unfolding from a folded configuration for oral intake to an unfolded configuration for gastric retention, wherein the device comprises:

two external layers sandwiching a functional layer therebetween;

the functional layer comprises DMF;

the functional layer being configured for imparting mechanical strength to the device sufficient to enable, upon unfolding of the device, the preservation of said unfolded configuration to provide gastric retention.

In one embodiment, the DMF in the functional layer is DMF coated particles described in the second aspect or any embodiments described therein.

In another embodiment, the DMF in the functional layer is DMF without enteric coating. In certain embodiments, when non-enterically coated DMF is used in the functional layer, the device can further comprise two enteric layers sandwiching the functional layer therebetween and the two external layers are located on the outside of the enteric layer. Alternatively, the non-enterically coated DMF can be embedded into an enteric layer. In another embodiment, the non-enterically coated DMF is embedded into the functional layer comprising one or more enteric polymers.

The enteric layer comprises one or more enteric polymer described herein.

In one embodiment, at least one of the external layers comprises perforations. Alternatively, both external layers comprises perforations.

In some embodiments, the folded device is folded parallel to one of the sides of the unfolded laminated/integrated device. In some embodiments, the folded dosage component has folds of increasingly smaller amplitudes upon extending away from the middle thereof so as to have an overall rounded cross section and to allow the folded device to be easily insertable into a container (envelop, e.g. capsule).

In some embodiments, the functional layer comprises a matrix further comprising one or more layers and a pharmaceutical composition comprising the DMF coated particles of the present invention, wherein DMF is releasable from the matrix. In some embodiments, the matrix comprises a polymer or polymer combination that is insoluble in gastric content. In some other embodiments, the functional layer may comprise a combination of compartments enclosing a pharmaceutical composition comprising the DMF coated particles and a matrix embedding the DMF coated particles.

In some other embodiments, the matrix comprises at least one soluble polymer or a soluble combination of polymers in combination with at least one insoluble polymer (or insoluble combination of polymers).

In some embodiments, the functional layer does not release DMF or DMF coated particles in the stomach. In one embodiment, the functional layer releases less than 20%, less than 15%, less than 10%, less than 5% or less than 1% of DMF coated particles in the stomach.

Alternatively, the functional layer releases DMF coated particles in the stomach over a long period time, such as 8-20 hours, 8-15 hours or 8-12 hours. In one embodiment, the functional layer releases 70-100%, 80-100%%, or 90-100% of DMF coated particles from the internal layer over 4-20 hours, over 8-20 hours, over 8-12 hours or over 4-8 hours.

The one or more layers may also comprise a layer of an enforcing polymeric composition so as to provide the desired configuration of the single or multi-layered device, once unfolded (e.g. following wetting by gastric content or by a medium resembling gastric content). The desired configuration may be achieved by the incorporation of an enforcing polymeric composition having a mechanical strength enabling, upon wetting and unfolding of the device, the preservation of the unfolded configuration of the device, i.e. after ingestion. The enforcing polymeric composition may be provided over DMF carrying layer (e.g. polymeric matrix), over the compartments comprising DMF, and/or may be integrally formed with or in the DMF layer.

According to one embodiment, the enforcing polymeric composition is in the form of one or more continuous or non-continuous polymer strips. For example, the strips may define a continuous or non-continuous frame at said device's periphery. The continuous or non-continuous frame may be either affixed or attached to the matrix or integrally formed with the matrix. Further, when as a strip or in a continuous form to form the so-called frame, the enforcing strip/frame may comprise a single or plurality of defects, e.g. gaps, depressions or slits, typically along the width of the strip/frame. Without being bound by theory, it is believed that such slits are essential for providing breakable areas along the strip/frame such that after a pre-determined time (e.g. when expulsion of the device from the body is desired, for example, after 12 hours) the areas containing the slits weaken and break, resulting in the disintegration of the device and its eventual removal from the stomach through the pylorus sphincter.

The combination of the enforcing composition, polymeric matrix and the pharmaceutical composition comprising DMF or DMF coated particles (or collectively as the pharmaceutical DMF composition) constitute, at times, the functional layer (the functionality denoting that these combined layers constitute a significant functional portion of the device, on the one hand, the gastro-retentivity, established by the enforcing layer, and the active principle ingredient, i.e. DMF, on the other hand). According to this embodiment, the assembly step may comprise assembling at least one layer of the enforcing composition, e.g. in a form of one or more continuous or non-continuous strips, with one or more layers comprising the DMF pharmaceutical composition or with the DMF pharmaceutical composition enclosed within the enforcing strips.

In accordance with one embodiment, the strips are in the form of a frame have inner boundaries defining a void, and the method comprises assembling the frame with one or more layers comprising the pharmaceutical DMF composition, such that the one or more layers comprising the pharmaceutical DMF composition is affixed, attached or integrally formed within said void. Alternatively or in addition, the pharmaceutical DMF composition may be enclosed, at least partially, within the frame.

The pharmaceutical DMF composition may be contained in the device in various forms. The incorporation of the pharmaceutical DMF composition thereof in the device is carried out in the assembly step. Thus, in accordance with an embodiment of the invention, the assembly step comprises at least one of the following: embedding the pharmaceutical DMF composition into one or more layers or into one or more compartments within one or more layers (e.g. a single layer may comprise areas of different composition of the polymer material forming it thereby forming distinguishable areas/compartments within the layer and these compartments may differently carry/release DMF so as to provide a differential release profile of DMF from the device); trapping the pharmaceutical DMF composition within at least two layers (e.g. such that the layers form a pouch housing the agent); enveloping the pharmaceutical DMF composition within at least one polymeric membrane segment; attaching said pharmaceutical DMF composition to or in at least one of said one or more layers of the device, or to a carrier, the carrier may be in the form of nano- or microspheres, nano- or microcapsules comprising particulate matter (i.e. a matrix) accommodating the active agent (by embedding, entrapping or having the agent affixed to the particulate's outer surface), beads coated or impregnated with the active agent, granules, pellets and compressed tablets.

In order to provide the desired mechanical strength in situ, once the device is in an unfolded state in the stomach, it is preferable that the enforcing polymeric composition, or at least one other layer of the device comprises a polymer that is insoluble in gastric juices/content. Alternatively, the mechanical strength can be provided by a combination of enteric and non-enteric insoluble polymers.

In addition to the aforementioned composition, the enforcing composition, irrespective of its shape or its number (e.g. number of strips made of the enforcing composition) within the device may further comprise a polymer, soluble in gastric content, which is either entrapped in the insoluble composition or is cross-linked in such way that it does not exude from the insoluble composition and can not be extracted without disintegrating the whole frame.

In accordance with a preferred embodiment, the device is a laminated device comprising two external layers made of a first material and sandwiching one ore more layers comprising one or more strips made of a second material and comprising the pharmaceutical DMF composition. The external sheets may comprise one or more polymers selected from the group consisting, without being limited thereto, polymers soluble in gastric content, polymers insoluble in gastric content, and a combination of any two or more thereof.

Nonetheless, in accordance with some other embodiments, the laminated device comprises two external layers made of a first material and sandwiching one ore more layers comprising one or more strips made of a second material, such that the one or both external layers comprise the pharmaceutical DMF composition. In the context of this embodiment, the pharmaceutical DMF composition may be embedded in as well as deposited to the outer surface of one or both external layers, e.g. by inkjet printing. An ink jet technology that has been developed is such that allows the preparation of poly(lactic-co-polycolic acid) (PLGA) microspheres with uniform particle size distribution [Radulescu D et al. Uniform paclitaxel-loaded biodegradable microspheres manufactured by ink jet technology Proceedings of the Winter Symposium and 11.sup.th International Symposium on Recent Advances in Drug Delivery Systems Salt Lake City, Utah, USA (2003)]. These microspheres while carrying the agent may then be affixed or attached to the one or both external layers.

In accordance with one embodiment, the external layers comprise a polymer or polymer composition that is soluble in gastric content. In another embodiment, the external layers are degradable in intestine.

According to another embodiment, the external layer is comprised of a mixture of a soluble polymer and an enteric polymer. According to another embodiment, the external layer comprises a cross-linked water soluble polymer, e.g. a soluble polymer cross-linked with glutaraldehyde, or an enzymatically hydrolyzed cross-linked gelatin and a derivative thereof.

Another example of external layer composition can be polyvinyl alcohol film, cross-linked with glutaraldehyde. Alternatively, said polyvinyl alcohol film could be subjected to one or more freeze-thaw cycles to induce crystallization.

Yet another example of external layer composition can be polyethylene oxide film, cross-linked by gamma irradiation.

In addition to the mentioned composition, the layers independently may comprise fillers, lubricants, plasticizers and other pharmaceutically acceptable processing adjuvants.

In some embodiments, one or more external layers comprise perforations. In one embodiment, both external layers of the device comprise perforations. The perforations may be generated before the layers are integrated into the device; as a sub-step in the assembly step or following the assembly step (i.e. after alt layers are assembled together into a whole unit), however, before the folding step; or the external layers may constitute a combination of materials such that when the device is wetted (or at least the external layers), perforations are produced. The dimensions, distribution pattern, shape and amount of perforations may vary between one device to another, within a layer of a single device as well as between the two external layers of a device, depending on the specific design of the device and the manner of their formation (e.g. mechanical slicing of holes or perforations resulting from dissolution of a component of the external layer following wetting by gastric content).

The perforations may be achieved by the use of a perforation apparatus having an array of pins or slicing knives presses against the layer to be perforated. As indicated above, the perforations may be of various dimensions and distribution patterns, and may be different between the two external layers. To this end, the perforation apparatus may comprise a series of differently arranged array of pins, the pins (or knives) being of the same or different dimensions etc.

In some embodiments, perforations comprise a plurality of holes. In other embodiments, perforations comprise a plurality of pores.

The assembly of the device's layers may be facilitated by various integration/lamination techniques known to those in the art, such as those described in the U.S. Pat. No. 8,609,136.

The assembly of the device's layers may be facilitated by various integration/lamination techniques known to those versed in the art. The assembly may be achieved by applying onto at least portions of some of the layers an integration agent, prior to bringing the respective layers into contact. The coating may be on one or more layers. A particular example includes application to at least one surface of the external layers, the strip/frame and the layer carrying the agent or agent-releasing formulation.

In accordance with one embodiment, the integration agent is an adhering agent which may be sprayed onto at least some of the layers of the device. In accordance with this embodiment, the adhering agent is preferably an organic solvent, a mixture of organic solvents, or a mixture of organic and water-based solvents such as salt solutions. More preferably the organic solvent is ethanol or mixture of ethyl acetate and ethanol.

In accordance with some other embodiments, the assembly is facilitated by other techniques such as welding (heat-welding, welding by high frequency, welding by ultrasound etc.), by curing (e.g. heat curing), fusion or any other technique involving melting both layers to form adherence at the interface between the layers as well as pressing the layers together (with or without heating to temperatures above room/ambient temperature). The said other techniques may involve the a priori application of an agent or substance to the layer so as to facilitate the assembly, as appreciated by those versed in the art.

In another preferred embodiment, the composition of the outer layer is treated so as to modify the properties of the outer surface, e.g. so as to prevent adhering of the undulated surface of the device as a result of folding. To this end, the assembly step may further comprise coating of the outer surface of one or both external layers with an anti-adhering coating, e.g. powder coating, polymer coating, liquid spray coating, dispersion (latex) coating, etc. The application of the powder may involve the a priori application of an adhering agent as defined above so as to facilitate adherence of the powder coating onto the respective layer.

In accordance with one preferred embodiment of the present invention, there is provided a method for producing a laminated device, preferably a gastro-retentive dosage form, comprising: (i) assembling a laminated device that comprises: a) a first external layer made of a first, typically polymeric material; b) a frame of a second, typically polymeric, material mounted on the first external layer; c) a drug-releasing formulation housed within the frame; and d) a second external layer made of the first material and mounted on the frame; and (ii) folding the laminated device into a folded device; and (iii) at least partially enclosing the folded device to produce the delivery device, preferably gastro-retentive dosage form, that can be administered orally.

In some preferred embodiments, the frame comprises one layer. In other embodiments, the frame comprises two or more layers. In accordance with one, non-limiting, embodiment, the frame has a thickness of around 400 microns, independent of the number of layers therein.

Further, in accordance with some other embodiments, the invention is directed to a method for producing an oral agent-releasing dosage form, comprising: (i) preparing or providing two first, essentially planar, polymeric sheet portions made of a first polymeric material that when wetted is permeable to the active agent, and a having outer boundaries; (ii) preparing or providing a second, essentially planar, polymeric sheet portion made of a second polymeric material defining a frame with outer boundaries and inner boundaries, the outer boundaries being of essentially the same shape as the outer boundaries of the first polymeric sheet portion and the inner boundaries defining a void area; (iii) preparing or providing a third, essentially planar, polymeric sheet portion made of a third polymeric sheet comprising an agent or agent releasing formulation releasable from the third sheet when in contact with an aqueous medium and defining a drug-containing and releasing matrix, said matrix having outer boundaries to fit within the void area; (iv) assembling the four portions such that said third sheet is placed within the void area and the two (the second sheet portion and the third sheet portion) being jointly sandwiched between the two first polymeric sheet portions, with all the outer boundaries essentially overlapping one another thus yielding a laminated device; (v) folding the laminated device into a form to fit into a capsule, and inserting it within a capsule made of a material that dissolves in the gastric fluids.

In some cases, this method comprises preparing first, second and third polymeric sheets made of the first, second and third polymeric materials, respectively, and cutting out the respective first, second and third polymeric sheet portions therefrom such that all sheets have essentially the same outer shape so as to facilitate the overlap between the outer boundaries thereof.

Yet further, in accordance with another embodiment, a method for producing an agent delivery device, comprising: (i) assembling an agent or an agent-releasing formulation within a generally planar assembly to form an integrated or laminated device, wherein the generally planar assembly may comprise a single or plurality of layers and may comprise or consist of a frame; (ii) manipulating the integrated or laminated device into a compacted integrated device, wherein the projected surface area of the compacted laminated dosage form is at least five times less than that of the integrated device; and (iii) at least partially enclosing the compacted device to produce the gastro-retentive dosage form.

In accordance with this embodiment, the projected surface area of the compacted device may also be at least six times, at least seven times, at least eight times, at least nine times and even at least ten times less than that of the integrated/laminated device form. The agent/agent releasing formulation may be assembled as part of a layer carrying the same and surrounded, at least partially, by the frame. Further, the generally planar assembly may comprise one or more external layers. A preferred embodiment in accordance with this method concerns a generally planar assembly comprising at least three integrated/laminated layers.

Further, in accordance with another embodiment of the present invention, the assembling step comprises introducing the agent or agent-releasing formulation into a layer of a second material (different from the material forming the external layers and/or the strips/frame).

Additionally, in accordance with another embodiment of the present invention, the folding step comprises: mounting the laminated device between two opposite faces of a press, each of which constituting a block having corrugated surface with ridges of one being essentially opposite to troughs of the other and essentially fitting one into the other; and pressing the two opposite faces one versus the other so as to form an undulated, three-dimensional device, wherein the undulations thereof correspond to the shape of the corrugated surface.

In another preferred embodiment, the folding step further comprises applying a force so as to press the undulated device from two sides and in a direction perpendicular to the undulations, into a folded device having folds formed along ridges and troughs of the undulations.

In some preferred embodiments, the folded device is folded parallel to one of the sides of the unfolded laminated/integrated device. In another preferred embodiment, the folded device has folds of increasingly smaller amplitudes upon extending away from the middle thereof so as to have an overall rounded cross section and to allow the folded device to be easily insertable into a container (envelop, e.g. capsule).

Thus, in accordance with the latter preferred embodiment, the two opposing surfaces of the press have such corrugations that following pressing, undulations with amplitudes that decrease from the middle towards the ends are formed, and upon the subsequent pressing in the said perpendicular direction an essentially circular cross-section is eventually attained, thus having an overall cylindrical form with a longitudinal axis parallel to the folds.

In one preferred embodiment, the eventual cross-section is such to allow the insertion of the folded device into a capsule of a kind conventionally used in pharmaceutical dosage forms. In accordance with this latter embodiment the process preferably further comprises at least partially enclosing the folded device within a capsule by pushing it along the longitudinal axis into one half of a capsule.

In accordance with a preferred embodiment of the present invention, the at least partially enclosing step of the above embodiment comprises:

placing the folded device into a capsule base (i.e. one half of the capsule before enclosure); and fitting a capsule cap (i.e. the other half of the capsule) onto the capsule base so as to form an encapsulated folded integrated delivery device/dosage form.

In some other embodiments, the folded device is at least partially enclosed within an enclosure through at least one process selected from: wrapping (e.g. with a polymeric thread), dipping (e.g. to form mold), spraying (e.g. with a polymeric coating material), encapsulating, binding (e.g. with a polymeric thread), tying (e.g. with a polymeric thread), molding (e.g. to form mold), enveloping and sealing.

In a second embodiment, the folded dosage form of the present invention are biodegradable, multi-layered gastroretentive dosage forms that have sustained release of DMF in the GI tract as described in U.S. Pat. No. 8,771,730.

In one embodiment, the folded dosage form comprises an internal layer containing DMF or DMF coated particles of the present invention (e.g., as described in the second aspect and any specific embodiments described therein) and a degradable polymer which is not instantly soluble in gastric fluid. The internal layer includes a first side and an opposing second side. At least one membrane is covering the internal layer. The membrane comprises at least one polymeric combination of a hydrophilic polymer and a polymer, insoluble in gastric media, the membrane being hydratable in the gastric media. The membrane is directly secured to and covers both sides of the internal layer and has a predetermined length greater than 20 mm in a planar orientation, the membrane and internal layer being arranged in an accordion folded orientation sufficiently compact to be placed within a capsule dissolvable within the stomach of a patient and simulated gastric media. The membrane and internal layer unfold from the accordion folded orientation to a length of at least 20 mm within 30 minutes of being exposed to gastric media. The membrane permits passage of gastric media from the environment to the internal layer and permits passage of the active agent from the internal layer through the membrane to the environment.

In another embodiment, the folded dosage form of the present invention comprise an internal layer comprising DMF or DMF coated particles of the present invention (e.g., as described in the second aspect and any specific embodiments described therein) and a degradable polymer which is not instantly soluble in gastric fluid. A first and second membranes cover the internal layer, the membranes including at least one polymeric combination of a hydrophilic polymer and a polymer, insoluble in gastric media and the membranes being hydratable. The first and second membranes are having a width and length greater than a width and length of the internal layer. The first and second membranes are being ultrasonically welded or otherwise affixed or attached directly together about the periphery of the first and second membranes. The first membrane is being ultrasonically welded to a first side of the internal layer, the second membrane is being ultrasonically welded to the second side of the internal layer. The ultrasonically welded internal layer and first and second membranes have a predetermined length greater than 20 mm in a planar orientation, the membrane and internal layer being arranged in an accordion folded orientation sufficiently compact to be placed within a capsule dissolvable within the stomach or simulated gastric media. The ultrasonic welds having sufficient mechanical strength and stability to remain intact when being exposed to gastric fluid.

In still another embodiment, the folded dosage form of the present invention comprises an internal layer comprising DMF or DMF coated particles of the present invention (e.g., as described in the second aspect and any specific embodiments described therein) and a degradable hydrophilic polymer which is not instantly soluble in gastric fluid and a degradable enteric polymer which is substantially insoluble at pH less than 5.5, and optionally a plasticizer. At least one membrane covers the internal layer, the membrane includes at least one polymeric combination of a hydrophilic polymer and a polymer, insoluble in gastric media, and at least one plasticizer. The membranes swell in the presence of gastric fluid. At least one of the materials in each of the internal layer and membranes are being capable of being ultrasonically welded together. The membrane is directly secured to and covers both sides of the internal layer and has a predetermined length greater than 20 mm in a planar orientation. The membrane and internal layer are being arranged in an accordion folded orientation sufficiently compact to be placed within a capsule dissolvable within the stomach or in simulated gastric media. The membrane permits passage of gastric media from the environment to the internal layer and permits passage of the active agent from the internal layer through the membrane to the environment. The membrane and internal layer unfold from the accordion folded orientation to a length of at least 20 mm within 30 minutes of being exposed to gastric fluid.

In still another embodiment, the folded dosage form of the present invention comprises an internal layer comprising DMF or DMF coated particles of the present invention (e.g., as described in the second aspect and any specific embodiments described therein) and a degradable hydrophilic polymer which is not instantly soluble in gastric fluid and a degradable enteric polymer which is substantially insoluble at pH less than 5.5, and a plasticizer. First and second membranes cover the internal layer, the membranes include at least one polymeric combination of a hydrophilic polymer and a polymer, insoluble in gastric media, and at least one plasticizer. The membranes swell in the presence of gastric fluid. At least one of the materials in each of the internal layer and membranes are being capable of being ultrasonically welded together. The membranes being directly secured to and covering both sides of the internal layer and having a predetermined length greater than 20 mm in a planar orientation, the membranes and internal layer being arranged in an accordion folded orientation sufficiently compact to be placed within a capsule dissolvable within the stomach. The membranes and internal layer unfold from the accordion folded orientation to a length of at least 20 mm within 30 minutes of being exposed to gastric fluid. The first and second membranes have a width and length greater than a width and length of the internal layer. The first and second membranes are ultrasonically welded or otherwise affixed or attached directly together about a periphery of the first and second membranes. The first membrane is ultrasonically welded to a first side of the internal layer. The second membrane is ultrasonically welded to the second side of the internal layer. The membrane permits passage of gastric media from the environment to the internal layer and permits passage of the active agent from the internal layer through the membrane to the environment. The ultrasonically welded internal layer and first and second membranes have a predetermined length greater than 20 mm in a planar orientation. The membrane and internal layer being arranged in an accordion folded orientation sufficient to be placed within a capsule dissolvable within the stomach. The ultrasonic welds having sufficient mechanical strength and stability to remain intact when being exposed to gastric fluid.

In one embodiment, the gastroretentive drug formulations are for the sustained release of DMF in the gastrointestinal tract and comprise: i.) an internal layer or compartment comprising the DMF coated particles (as described in the second aspect or any embodiments therein) and one or more pharmaceutical excipients, of which at least one is a polymer; ii.) two membranes forming together an envelope around the inner membrane, each comprising at least one polymeric combination of a polymer which is not soluble in gastric juice, and a hydrophilic swelling polymer, and at least one plasticizer; and iii.) optionally an additional layer covering each outer membrane comprising a powder or a film that prevents adherence of the outer membrane onto itself when folded inside the capsule.

In preferred embodiments, the gastroretentive drug formulations effectively unfold and retain their mechanical integrity in acidic pH for up to 24 hours and completely biodegrade after 3 hours in simulated intestinal fluid.

In one aspect, the polymer in the internal layer is a degradable polymer which is not instantly soluble in gastric fluid. In another aspect, the polymer is a degradable enteric polymer which is substantially insoluble at pH less than 5.5. The invention also contemplates mixtures of polymers as described above.

In one embodiment, the enteric polymer in the internal layer is polymethacrylate copolymer. In different embodiments, the enteric polymer is cellulose acetate phthalate, or hydroxypropylmethyl cellulose phthalate, or hydroxypropyl methyl cellulose acetate succinate. In a preferred embodiment, the DMF coated particles described above in the second aspect or any embodiments described therein and the polymer are substantially uniformly distributed in the internal layer.

In another embodiment, the polymeric combination of the outer membranes comprises gelatin and hydroxypropyl methyl cellulose acetate succinate as enteric polymer. In one embodiment, the enteric polymer in the outer membranes is polymethacrylate copolymer type A. In a different embodiment, the enteric polymer in the outer membranes is polymethacrylate copolymer type C. In a further embodiment, the plasticizer in the outer membranes is propylene glycol.

In a preferred embodiment, the internal layer or compartment, the outer membranes and the optional additional layers are sealed by applying ultrasonic welding.

In an additional embodiment, the internal layer provides at least 50% of the mechanical strength of the whole gastroretentive drug formulations when wetted with gastric fluid. In a preferred embodiment, the gastroretentive drug formulation reaches its maximum strength within one hour in simulated gastric fluid. In yet another preferred embodiment, the internal layer has a planar-accordion geometry that unfolds to at least 50% of its original length within 30 minutes in gastric media.

In one aspect, the gastroretentive drug formulation is fully degradable within 3 hours in simulated intestinal fluid. In an additional aspect, the gastroretentive drug formulation provides gastric retention for up to 24 hours under low or medium calorie diet. In yet another aspect, the gastroretentive drug formulation moves in the stomach during gastric retention.

The gastroretentive drug formulations are designed for oral administration and are compacted or folded into a standard size capsule which is easily swallowed. The active ingredient DMF is incorporated in the gastroretentive drug formulations as dissolved matter in composition of the formulation, powders, grains, spheres, particles, microparticles, nanoparticles, multiparticulates, tablets or microcapsules.

In one embodiment, the gastroretentive drug delivery system includes an internal layer and an outer layer. The outer layer is formed from two films which are slightly larger than the internal layer and which are sealed or welded together around their perimeter and completely envelope the internal layer. Along with welding which connects the outer layers together, the outer portion of the internal layer is also welded to the outer layers.

Alternatively, the gastroretentive drug delivery system includes an internal layer and an outer layer, whereas the outer layer is formed from two membranes which are equal in size with the internal layer and which are sealed or welded together around their perimeter and the outer portion of the inner layer. Optionally the gastroretentive delivery system comprises an additional layer which is either larger or equal in size to the inner/outer membranes assembly, and envelops the assembly to prevent adhesion of the membranes onto themselves; the said layer can be formed with one or more membranes, ultrasonically welded or otherwise attached or affixed onto the assembly, and can optionally comprise an API. The ultrasonically welded or otherwise attached internal layer and outer layers are folded in an accordion arrangement and placed within a capsule. In some embodiments, the capsules are made from gelatin or hypromelose. The layers are shaped in essentially oval polygonal form such that they maximize the amount of space within the capsule that is filled. Once the gelatin or hypromelose capsule dissolves within the gastric medium, the internal layer and outer layers expand from the accordion folded orientation to a more planar orientation.

The gastroretentive drug formulations of the present invention markedly improve absorption and bioavailability of DMF due to its ability to withstand peristalsis and mechanical contractility of the stomach, and consequently, release the drug in a controlled manner onto its absorption sites and without premature transit into non-absorbing regions of the GI tract. The gastroretentive drug formulation can provide gastric retention of DMF having a narrow absorption window for up to 24 hours under low or medium calorie diet. In addition, administration of these formulations to a mammal can improve the pharmacokinetic and pharmacodynamic properties of DMF. Since the gastroretentive drug formulations are fully degradable, they provide a means to administer the proper dose of the drug without generating non-degradable residues that would not be eliminated after drug release.

The gastroretentive drug formulations are stable, fully degradable and provide efficient delivery of DMF in the gastrointestinal tract due to the combination of an internal layer having planar-accordion geometry where all components are fully biodegradable. The combination of swelling outer membrane layers with a substantially non-swelling internal layer having planar accordion geometry causes the internal layer to undergo an unfolding process once the formulation reaches the stomach, thus extending gastric residence time and preventing the dosage form from being evacuated until substantial or complete release.

Sustained-Release Gastroretentive Drug Formulations

In one embodiment, the present invention provides a stable, degradable, multi-layered gastroretentive drug formulation for the sustained release of DMF in the gastrointestinal tract. The gastroretentive drug formulation comprises: i.) an internal layer or compartment comprising DMF coated particles of the present invention (e.g., as described in the second aspect and any specific embodiments described therein), one or more polymers and one or more modifying agents such as plasticizers and/or solubilizers and/or fillers; ii.) two outer membranes, each comprising at least one polymeric combination of hydrophilic polymer and a polymer insoluble in gastric media, and at least one plasticizer; and iii.) optionally an additional layer covering each outer membrane and comprising a powder or a film that prevents adherence of the outer membranes to itself.

In accordance with another embodiment of the invention, degradable, multi-layered gastroretentive drug formulation for the sustained release of DMF can be combined with one or more immediate release layers covering the outer membranes and comprising DMF (e.g., DMF coated particles of the present invention, such as those described in the second aspect and any specific embodiments described therein) and a polymer and optionally other excipients, known in the art, that provides for the immediate release of DMF to form degradable, multi-layered gastroretentive drug formulation for combined immediate-release and sustained-release of DMF. Optionally an additional layer covering each outer membrane and comprising a powder or a film that prevents adherence of the outer membranes to itself is included. Additional disclosure regarding the immediate and controlled release formulations are provided below.

a) Internal Layer

The internal layer or compartment in the gastroretentive drug formulations comprise the DMF coated particles of the present invention (e.g., those described in the second aspect and any specific embodiments described therein) and a polymer substantially uniformly distributed throughout the internal layer. The polymer can be a degradable hydrophilic polymer which is not instantly soluble in gastric fluid, a degradable enteric polymer which is substantially insoluble at pH less than 5.5, a hydrophobic polymer or mixtures thereof. It can further comprise acceptable pharmaceutical additives, such as plasticizers, humectants, fillers and others.

Examples of degradable hydrophilic polymers which are not instantly soluble in gastric fluid suitable for the invention are hydroxypropyl cellulose, hydroxypropylmethyl cellulose, polyvinyl pyrrolidone, polyethylene oxide and methylcellulose. Preferably, the enteric polymer is a polymethacrylate copolymers, cellulose acetate phthalate, hypromelose acetate succinate or hypromellose phthalate. These polymers are combined with the DMF coated particles of the present invention (e.g., those described in the second aspect and any specific embodiments described therein).

Preferably, the internal layer has planar accordion geometry. This feature, together with the presence of polymers as described above in the internal layer or compartment provides the internal layer with substantial mechanical strength.

Preferably, the internal layer has a mechanical strength with Young's modulus of from about 0.5 to 15 Kgf/mm$^2$. Preferably, the range could be from about 3.0 to about 10.0 Kgf/mm$^2$ or from about 3.0 to about 6.0 Kg f/mm$^2$. The stress may range from about 0.03 to about 0.6 Kgf/mm$^2$ after 1 hour in simulated gastric fluid, such that the gastroretentive drug formulation reaches its maximum strength within one hour in simulated gastric fluid. Alternatively the range for stress may be from about 0.05 to about 0.4 Kgf/mm$^2$ or about 0.1 to about 0.4 Kgf/mm$^2$.

The components of the internal layer may be altered. In some instances, the internal layer does not allow effective welding between the outer and internal layer. In such situations, the internal layer may be composed of the two or more portions, where each portion has definite function. In one instance, the central region (welding free) can be formulated as separate film to hold the active ingredient and be placed into the central portion and over the inner film comprising an additional portion that will support this central portion. This additional portion can then be welded to the outer layer. In another instance, whereas the internal layer cannot be formulated to develop the necessary mechanical strength in the gastric medium, at least one additional layer, optionally comprising no drug, could be used as a scaffold, whereupon the formulated drug reservoir film could be laid and welded or otherwise attached or affixed, onto one or both sides of said backbone, and the assembly could be welded to the outer membranes and other components of the delivery system.

b) Outer Membranes

Each of the outer membranes in the gastroretentive drug formulations comprises at least one polymeric combination of a hydrophilic polymer and a polymer, insoluble in gastric media, and at least one plasticizer.

Examples of suitable ingredients for the invention include gelatin, hydroxypropylcellulose, hydroxypopyl methycellulose, pectin, polyethylene oxide, starch, and zein. Preferably, the hydrophilic polymer is gelatin. The amount of gelatin in each of the outer membranes is between about 20 and about 45% of the total outer membrane composition, and preferably between about 25 and about 35% of the total outer membrane composition.

Examples of enteric polymers that can be used in the outer membranes include hypromellose phthalate, hypromellose acetate succinate and polymethacrylate co-polymers. Preferably, the enteric polymer is polymethacrylate copolymer type A or polymethacrylate copolymer type C.

Plasticizers suitable for the invention include various polyethylene glycols, glycerin, triethylcitrate. Preferably, the plasticizer is propylene glycol.

The outer membranes swell in the presence of gastric fluid and are fully degradable within two hours in simulated intestinal fluid. The combination of swelling outer membrane layers with a non-swelling internal layer having planar accordion geometry causes the internal layer to undergo an unfolding process once the formulation reaches the stomach, thus extending gastric residence time and preventing the drug-containing dosage form from being evacuated until complete release. In one embodiment the internal layer has a swelling rate less than the swelling rate of the membrane.

The membrane permits passage of gastric medium from the environment to the internal layer and permits passage of the DMF coated particles from the internal layer through the membrane to the environment.

In some instances the kinetics of such transport can be unacceptably low. Therefore in some embodiments the outer membranes can be perforated with one or more orifices to facilitate the mass transfer processes through the membrane. In preferred embodiments the orifices are uniformly distributed over the area hereabout the formulated drug layer.

c) Optional Additional Layer

The gastroretentive drug formulations of the invention may further comprise an optional additional layer covering each outer membrane and comprising a powder or a film. In some instances it may be found that the outer layers stick together in the capsule and do not unfold properly upon dissolving of the capsule. In such situations, this optional layer prevents adherence of the outer membranes to themselves and allows for the proper opening of the GRDF. In preferred embodiments, the optional layer comprises at least one powder, and optionally at least one polymer. In other embodiments the preferred polymers are rapidly-dissolving film formers, which can be selected from but not limited to soluble cellulose derivatives, i.e. methyl cellulose, hydroxypropyl cellulose, hydroxyethyl cellulose, hypromelose; various grades of povidone; polyvinyl alcohol and its derivatives, i.e. Kollicoat IR; soluble gums and others. The films may further comprise surface-active agents, plasticizers and humectants.

Ultrasonic Welding

The internal layer or compartment, the outer membranes, the optional layers and/or the immediate release layers may be attached to each other by many means. Preferably, they are sealed by applying ultrasonic welding. One example of a device suitable for these purposes is the Dynamic 745 ultrasonic welder from Rinco Ultrasonics, but other devices may be employed. The welding effectively seals the internal layer within the outer layer by welding the outer layers together and also welding the perimeter of the internal layer to the outer layer. It can also efficiently attach the layers to one another without sealing a whole envelope, meaning that there is no need for same-material welding, should the formulations be compatible.

Different patterns and times may be used for the welding based on the needs of those skilled in the art. Although the periphery of the layers can be welded together, the current embodiments do not weld the central portion of the GRDF device so as to minimize any heating or effects on the majority of the internal layer which holds the active pharmaceutical agent for controlled release. In some situations it may be necessary to weld more of the internal layer based on the composition of the GRDF.

Gastric Retention Under Low and Medium Calorie Diet

The gastroretentive drug formulations maintain their physical integrity over a prolonged period of time, such that DMF is retained in the stomach for up to 24 hours under low or medium calorie diet. The use of a low and medium calorie diet is advantageous because it follows normal dietary habits of the patients and does not demand an excessive meal with each instance of dosing of the GRDF. Although the GRDF may be retained in the stomach for extended periods of time all of the GRDF components are degradable and undergo complete degradation once they reach the intestine.

In a third embodiment, the folded gastroretentive dosage form of the present invention comprises an internal layer comprising DMF and at least one outer membrane covering the internal layer, wherein the outer membrane is hydratable at a rate greater than that of the internal layer. The outer membrane and the internal layer are arranged in an accordion folded configuration and the outer membrane and the internal layer provide sufficient mechanical force to unfold from the initial accordion folded configuration to an unfolded configuration when exposed to gastric fluid.

In certain embodiments, the gastrorentive dosage form is retained in the stomach for at least 3 hours, at least 4 hours, at least 8 hours, or at least 12 hours.

In a first specific embodiment, the folded gastroretentive dosage form is a delayed pulse release form, which does not substantially release DMF when the device is retained in the stomach; while provides immediate release of DMF in small intestine. In one embodiment, less than 20%, less than 10%, less than 5% or less than 1% of DMF is released is released in the stomach. In one embodiment, more than 70%, more than 80%, more than 90%, more than 95% or more than 99% of DMF is released within 2 hours or within 1 hour in small intestine.

In one embodiment, in the delayed pulse release form described above, the internal layer comprises DMF coated particles of the present invention.

In another embodiment, in the delayed pulse release form described above, the internal layer comprises non-enterically coated DMF. In one embodiment, the non-enterically coated DMF is embedded into an enteric layer. Alternatively, the dosage form further comprises two enteric layers sandwiching the internal layer therebetween, wherein the enteric layer comprises one or more enteric polymers described herein. In another embodiment, the non-enterically coated DMF is embedded into the internal layer comprising one or more enteric polymers. Any enteric polymers known in the art, particularly those described herein can be used in the dosage forms described herein.

In one embodiment, the internal layer comprises the DMF coated particles of the present invention (e.g., those described in the second aspect and any specific embodiments described therein) and a polymer substantially uniformly distributed throughout the internal layer. The polymer can be any suitable polymer or polymer combinations that are insoluble in gastric medium.

In a second specific embodiment, the folded gastroretentive dosage form is a delayed sustained release form. The internal layer comprises DMF coated particles of the present invention and releases DMF coated particles in the stomach over an extended period of time. In one embodiment, 70-100%, 80-100%%, or 90-100% of DMF coated particles are released from the internal layer over 4-20 hours, over 8-20 hours, over 8-12 hours or over 4-8 hours.

The internal layer comprises the DMF coated particles of the present invention (e.g., those described in the second aspect and any specific embodiments described therein) and a polymer substantially uniformly distributed throughout the internal layer. The polymer can be a degradable hydrophilic polymer which is not instantly soluble in gastric fluid, a degradable enteric polymer which is substantially insoluble at pH less than 5.5, a hydrophobic polymer or mixtures thereof. It can further comprise acceptable pharmaceutical additives, such as plasticizers, humectants, fillers and others.

Examples of degradable hydrophilic polymers which are not instantly soluble in gastric fluid suitable for the invention are hydroxypropyl cellulose, hydroxypropylmethyl cellulose, polyvinyl pyrrolidone, polyethylene oxide and methylcellulose. Preferably, the enteric polymer is a polymethacrylate copolymers, cellulose acetate phthalate, hypromelose acetate succinate or hypromellose phthalate. These polymers are combined with the DMF coated particles of the present invention (e.g., those described in the second aspect and any specific embodiments described therein).

In certain embodiments, the internal layer described above (e.g. in the third embodiment or the first or second specific embodiment) has planar accordion geometry. This feature, together with the presence of polymers as described above in the internal layer provides the internal layer with substantial mechanical strength. Preferably, the internal layer has a mechanical strength with Young's modulus of from about 0.5 to 15 Kgf/mm$^2$. Preferably, the range could be from about 3.0 to about 10.0 Kgf/mm$^2$ or from about 3.0 to about 6.0 Kg f/mm$^2$. The stress may range from about 0.03 to about 0.6 Kgf/mm$^2$ after 1 hour in simulated gastric fluid, such that the gastroretentive drug formulation reaches its maximum strength within one hour in simulated gastric fluid. Alternatively the range for stress may be from about 0.05 to about 0.4 Kgf/mm$^2$ or about 0.1 to about 0.4 Kgf/mm$^2$.

In certain embodiments, the outer membranes in the device described above swell in the presence of gastric fluid and are fully degradable within two hours in simulated intestinal fluid. The combination of swelling outer membrane layers with a non-swelling internal layer having planar accordion geometry causes the internal layer to undergo an unfolding process once the formulation reaches the stomach, thus extending gastric residence time and preventing the drug-containing dosage form from being evacuated until complete release. In one embodiment the internal layer has a swelling rate less than the swelling rate of the membrane.

Each of the outer membranes in the gastroretentive drug formulations comprises at least one polymeric combination of a hydrophilic polymer and a polymer, insoluble in gastric media, and at least one plasticizer.

Examples of suitable ingredients for the invention include gelatin, hydroxypropylcellulose, hydroxypopyl methycellulose, pectin, polyethylene oxide, starch, and zein. Preferably, the hydrophilic polymer is gelatin. The amount of gelatin in each of the outer membranes is between about 20 and about 45% of the total outer membrane composition, and preferably between about 25 and about 35% of the total outer membrane composition.

Examples of enteric polymers that can be used in the outer membranes include hypromellose phthalate, hypromellose acetate succinate and polymethacrylate co-polymers. Preferably, the enteric polymer is polymethacrylate copolymer type A or polymethacrylate copolymer type C.

Plasticizers suitable for the invention include various polyethylene glycols, glycerin, triethylcitrate. Preferably, the plasticizer is propylene glycol.

In certain embodiments, the outer membrane permits passage of gastric media from the environment to the internal layer and permits passage of the active agent from the internal layer through the membrane to the environment.

In certain embodiments, the folded gastroretetive dosage form described in the third embodiment or the first or second specific embodiment comprises two outer membranes sandwiching the internal layers therebetween. When the dosage form further comprises two enteric layers as described above, the two outer membranes are located outside of the two enteric layers respectively.

In certain embodiments, the folded gastroretentive dosage form described above is placed in a capsule for oral intake, wherein the capsule is dissolvable in the stomach.

In certain embodiments, when exposed to gastric medium, the dosage form unfold from the initial accordion folded configuration to an unfolded configuration having a length of at least 20 mm within 30 minutes, within 20 minutes, within 15 minutes or within 10 minutes.

In certain embodiments, the gastroretentive drug formulations effectively unfold and retain their mechanical integrity in acidic pH for up to 24 hours and completely biodegrade after 3 hours in simulated intestinal fluid.

d. Intestinal Retention Dosage Form

In some embodiments, the invention provides an intestinal retention dosage form for delivering an API to a subject treated. In some embodiments, the intestinal retention dosage form releases the API in the GI tract of a subject in a sustained period of time between about 0.25 and about 24 hours (e.g., about 2, about 4, about 6, about 8, about 10, about 12, about 14, about 16, about 18, about 20, about 22, or about 24 hours). Various methods for achieving intestinal retention are known, for example, via mucoadhesion or mechanical retention.

Mucoadhesive Dosage Form

In some embodiments, the intestinal retention dosage form is a mucoadhesive dosage form, which is adhesive to mucosal surface of the gastrointestinal tract (e.g., small intestine) of a subject treated. In some embodiments, the API (e.g., the DMF coated particles described in the second aspect or any embodiments described therein) in the mucoadhesive dosage form is retained in the small intestine of a subject treated. Various techniques for preparing a mucoadhesive dosage form are known. For example, U.S. Pat. No. 6,022,562, incorporated by reference herein, discloses microcapsules containing particles of drug that are coated with a film-forming polymer derivative, a hydrophobic plasticizer, a functional agent, and a nitrogen-containing polymer. These microparticles remain in the small intestine and release the drug over a period of time. Methods for evaluating effectiveness of mucoadhesive dosage forms are also known.

U.S. Publication No. 2004/0234601 A1, incorporated by reference herein, also discloses a mucoadhesive dosage form.

Another example of a mucoadhesive dosage form is disclosed in U.S. Pat. No. 8,298,574 B2, incorporated by reference herein.

Mucoadhesive dosage forms herein can comprise an API and one or more mucoadhesive polymers. In some embodiments, the API is seal coated, enterically coated, or seal and enterically coated. In some embodiments, the only active pharmaceutical ingredient in the mucoadhesive dosage form is DMF. Suitable mucoadhesive polymers are known and include any polymer that is or becomes adhesive to a mucosal membrane (e.g., mucosal membrane of small intestine) upon hydration. The mucoadhesive polymers can be cationic, anionic, or neutral. The mucoadhesive polymers can be natural or synthetic. The mucoadhesive polymer can be biocompatible. The mucoadhesive polymer can be water soluble or water insoluble.

Non-limiting synthetic mucoadhesive polymers suitable for the invention include, for example, poly(acrylic acid), polyvinyl alcohol, polyamides, hydroxypropyl methylcellulose (HPMC), poly(methylacrylate) derivatives, polycarbonates, polyalkylene glycols, polyvinyl ethers/esters/halides, methylcellulose (MC), sodium carboxymethylcellulose (CMC), polymethylmethacrylic acid, and hydroxypropyl cellulose (HPC).

Non-limiting biocompatible mucoadhesive polymers suitable for the invention also include, for example, cellulose based polymers, ethylene glycol polymers and its copolymers, oxyethylene polymers, polyvinyl alcohol, polyvinyl acetate, and esters of hyaluronic acid.

Non-limiting synthetic mucoadhesive polymers suitable for the invention also include, for example, cellulose derivatives (e.g., CMC, sodium CMC, thiolated CMC, hydroxylethyl cellulose (HEC), HPC, HPMC, methyl cellulose (MC), methylhydroxyethylcellulose) and poly(acrylic acid)-based polymers (e.g., polyacrylic acid (PAA), polyacrylates, poly (methylvinylether-comethacrylic acid), poly(2-hydroxyethyl methacrylate), poly(acrylic acid-co-ethylhexylacrylate), poly(methacrylate), poly(alkylcyanoacrylitte), poly (isohexylcyanoacrylate), poly(isobutylcyanoacrylate), or copolymer of acrylic acid and PEG).

Non-limiting natural mucoadhesive polymers suitable for the invention include, for example, agarose, chitosan, gelatin, pectin, sodium alginate, and various gums (e.g., guar, xanthan, gellan, carrageenan).

Non-limiting cationic mucoadhesive polymers suitable for the invention include, for example, aminodextran, chitosan, trimethylated chitosan, and dimethylaminoethyl dextran.

Non-limiting anionic mucoadhesive polymers suitable for the invention include, for example, Chitosan-EDTA, Cellulose Propionate (CP), CMC, pectin, PAA, polycarbonate (PC), sodium alginate, sodium CMC, and xanthan gum.

Non-limiting neutral mucoadhesive polymers suitable for the invention include, for example, hydroxyethyl starch, HPC, poly(ethylene oxide), Poly(Vinyl Acetate) (PVA), poly (vinyl pyrrolidone) (PVP), and scleroglucan.

Non-limiting water soluble mucoadhesive polymers suitable for the invention include, for example, CP, hydroxylethylcellulose (HEC), HPC, HPMC, PAA, sodium CMC, and sodium alginate.

Non-limiting water insoluble mucoadhesive polymers suitable for the invention include, for example, chitosan, ethyl cellulose (EC), and PC.

In some embodiments, the one or more mucoadhesive polymers comprises chitosan, lectin, or a combination thereof. In some embodiments, the one or more mucoadhesive polymer can be any combination of the suitable mucoadhesive polymers described above.

In any of the embodiments described herein, the mucoadhesive dosage form may be in any suitable forms (e.g., microspheres, microparticles, nanoparticles, films, or tablets). In some embodiments, the mucoadhesive dosage form is in the form of microspheres. In some embodiments, the mucoadhesive dosage form is in the form of tablets.

In some embodiments, the mucoadhesive dosage form releases the API (e.g., DMF) in the GI tract of a subject in a sustained period of time (e.g., about 2, about 4, about 6, about 8, about 10, about 12, about 14, about 16, about 18, about 20, about 22, or about 24 hours).

Mechanical Retention

In some embodiments, the intestinal retention dosage form is a dosage form comprising a plurality of API containing microparticles having a mean diameter of about 50 microns to about 1000 microns (e.g., about 50, 100, 150, 200, 300, 400, 500, 750, 1,000 microns, or any ranges thereof) that are retained (e.g., mechanically retained) in the GI tract (e.g., small intestine) for an extended period of time from about 2 hours to about 12 hours (e.g., about 2, 3, 4, 5, 6, 7, 8, 10, 12, or any ranges thereof). In some embodiments, the API in the intestinal retention dosage form is retained in the small intestine of a subject treated. In some embodiments, the microparticles have a mean diameter of about 100 microns to about 500 microns. In some embodiments, the microparticles have a mean diameter of about 50 microns to about 500 microns. In some embodiments, the only active pharmaceutical ingredient in the intestinal retention dosage form is DMF. Methods for preparing a mechanically retained intestinal retention dosage form are known, for example, via the Micropump® method.

B. Unit Dosage Forms

In a fourth aspect, the present invention provides unit dosage forms comprising the DMF coated particles described above in the second aspect of invention or any embodiments described therein. In certain embodiments, the unit dosage forms of the present invention have similar pharmacokinetic profile as the current twice a day dosing regimen and are suitable for once a day dosing.

The controlled release dosage form described in the third aspect of the present invention may be provided as a unit dosage form or part of a unit dosage form or in a kit.

In some embodiments, a kit (e.g., a blister pack) comprises one or more pharmaceutical formulations, wherein the pharmaceutical formulation when orally dosed to a subject delivers to the GI tract (e.g., upper GI tract or lower GI tract) of the subject treated, the total daily dose of API, in a sustained or pulsatile manner (e.g., to the upper gastrointestinal tract or lower GI tract (e.g., small intestine) of a subject treated). In some embodiments, the kit (e.g., a blister pack) comprises at least two physically separated dosage forms (e.g., two capsules, two tablets, or one capsule and one tablet), wherein at least one of the dosage forms is a controlled release dosage form described herein. In some embodiments, the only active ingredient in the pharmaceutical formulation(s) of the kit (e.g., a blister pack) is DMF.

In some embodiments, the invention provides a unit dosage form. In some embodiments, the unit dosage form is a single unit of a controlled release dosage form described herein. In some embodiments, the unit dosage form is a combination of one or more units of a controlled release dosage form described herein and one or more units of a second dosage form (e.g., a controlled release dosage form described herein, an enterically coated immediate release dosage form, a combination thereof). In some embodiments, the controlled release dosage form is a sustained release dosage form. In some embodiments, the second dosage form is a delayed release dosage form.

In some embodiments, the unit dosage form, when orally dosed to a subject, delivers to the GI tract (e.g., upper GI tract or lower GI tract (e.g., small intestine)) of the subject treated, more than one dose of the API, in a sustained or pulsatile manner, wherein the unit dosage form comprises a first dosage component comprising a first dose of the API; and a second dosage component comprising a second dose of the API.

In some embodiments, the second dose of the API in the unit dosage form is retained in the stomach and/or small intestine of a subject treated for at least 3 hours (e.g., about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, or any ranges thereof). In some embodiments, the second dose of the API in the unit dosage form is retained in the stomach and/or small intestine for about 3 hours to about 17 hours. In some embodiments, the second dose of the API in the unit dosage form is retained in the stomach and/or small intestine of a subject treated for at least 4 hours, at least 5 hours, at least 6 hours, at least 7 hours, or at least 8 hours. In some embodiments, the second dose of the API in the unit dosage form is retained in the stomach and/or small intestine of a subject treated for at least 5 hours, at least 6 hours, or at least 7 hours.

In some embodiments, the second dosage component of the unit dosage form is a controlled release dosage form described above (e.g., gastroretentive folded dosage forms described in the third aspect of the present invention).

In some embodiments, the first and second dosage components may be in one dosage form (e.g., a tablet or a capsule). In some embodiments, the only active ingredients in the unit dosage form is DMF.

In some embodiments, the unit dosage form (e.g., as described herein) releases MMF, or a compound that can be metabolized into MMF in vivo, in a bimodal or multi-modal manner in which a first dose of the API after an initial delay time to provide a pulse of drug release and one or more additional doses of the API are released each after a respective lag time to provide additional pulses of drug release. In some embodiments, the pulses of drug release are delivered to the upper gastrointestinal tract of a subject treated. In some embodiments, the pulses of drug release are delivered to the lower gastrointestinal tract of a subject treated. In some embodiments, one pulse of drug release is delivered to the upper gastrointestinal tract of a subject treated and a second pulse of drug release is delivered to the lower gastrointestinal tract of the subject treated.

It may be advantageous to deliver DMF in pulses to the upper GI tract rather than to the lower GI tract for absorption. In some embodiments, the pulses of DMF are delivered to the upper gastrointestinal tract of a subject treated.

In some embodiments, the invention provides a unit dosage form that delivers MMF, or a compound that can be metabolized into MMF in vivo, in pulses to the upper GI tract upon oral administration of the unit dosage form. In some embodiments, the unit dosage form comprises a first dosage component comprising a first dose of API; and a second dosage component comprising a second dose of API;

wherein when the unit dosage form is administered to a subject orally, the first and second doses of API, are delivered to the upper GI tract of the subject in a pulsatile manner.

In some embodiments, the second dosage component of the unit dosage form is a controlled release dosage form described above in the third aspect of the invention.

In some embodiments, patients orally administered a unit dosage form described herein (with or without food) once daily exhibit one or more of the following pharmacokinetic parameters in the subject: (a) a mean plasma MMF $AUC_{overall}$ ranging from about 4.81 h·mg/L to about 11.2 h·mg/L; (b a mean plasma MMF $AUC_{0-12}$ ranging from about 2.4 h·mg/L to about 5.5 h·mg/L; and (c) a mean $AUC_{0-infinity}$ ranging from about 2.4 h·mg/L to about 5.6 h·mg/L. In some embodiments, the subject treated exhibits a pharmacokinetic profile characterized by both (a) and (b), both (a) and (c), or both (b) and (c). In some embodiments, the subject treated exhibits a pharmacokinetic profile characterized by (a), (b), and (c).

In some embodiments, a subject orally administered a unit dosage form described herein once daily exhibits a mean MMF plasma area under the curve 0-12 ($AUC_{0-12}$) of about 2.36 h·mg/L to about 5.50 h·mg/L, from about 2.75 h·mg/L to about 5.10 h·mg/L, or from about 3.14 h·mg/L to about 4.91 h·mg/L. In one embodiment, the subject exhibits a mean $AUC_{0-12}$ of about 3.93 h·mg/L.

In some embodiments, a subject orally administered a unit dosage form described herein (with or without food) once daily exhibits a mean MMF plasma overall area under the curve ($AUC_{overall}$) of about 4.81 h·mg/mL to about 11.2 h·mg/mL, or from about 6.40 h·mg/L to about 10.1 h·mg/L. In one embodiment, the subject exhibits a mean $AUC_{overall}$ of about 8.02 h·mg/L.

First Dosage Component

Upon oral administration of the unit dosage form to a subject, the first dosage component comprising a first dose of API, may provide the first dose, for example, as a first pulse of an API, for absorption in the upper GI tract of the subject. In any of the embodiments described herein, the first dosage component can be an enterically coated immediate release or a delayed release dosage form. In some embodiments, the only active ingredient in the first dosage component is DMF. In some embodiments, the first dosage component comprises the DMF coated particles of the present invention as described in the second aspect or any specific embodiments described therein.

In some embodiments, suitable amounts of API for the first dosage component include those that can provide, by itself or in combination with one or more doses from, for example, a second dosage component, a daily amount of the respective compound ranging from about 1 mg/kg to about 50 mg/kg (e.g., from about 2.5 mg/kg to about 20 mg/kg or from about 2.5 mg/kg to about 15 mg/kg).

Suitable doses of DMF for the first dosage component may be any therapeutically effective dose, e.g., an amount that is effective in treating multiple sclerosis. For example, suitable doses of DMF for the first dosage component may be any dose from 20 mg to 1 g of DMF. In some embodiments, the suitable doses of DMF in the first dosage component may be any dose from about 80 mg to about 1000 mg of DMF. In some embodiments, the suitable doses of DMF in the first dosage component may be any dose from about 100 mg to about 750 mg of DMF. In some embodiments, the suitable doses of DMF in the first dosage component is about 200 to about 600 mg. In some embodiments, the suitable doses of DMF in the first dosage component may be any dose from about 300 to about 600 mg.

In some embodiments, the DMF in the first dosage component is about 60 mg, about 80 mg, about 100 mg, about 120 mg, about 160 mg, about 200 mg, about 240 mg, about 320 mg, about 360 mg, about 400 mg, about 480 mg, about 600 mg, about 720 mg, about 800 mg, about 900 mg, about 1000 mg of DMF, or any ranges thereof.

The first dosage component can contain an amount of a compound that that can metabolize into MMF that provides an equivalent amount of MMF as the doses of DMF described above.

Suitable first dosage component may be in a form of a micro-pellet, a micro-tablet, a capsule (such as a soft or hard gelatine capsule), a granulate, or a tablet. In some embodiments, the first dosage component is in the form of micro-tablets or micropellets (e.g., enteric-coated microtablets or micropellets). Suitable microtablets or micropellets are, without limitation, those having a mean diameter of 5,000 microns or less (e.g., 4,000 microns or less, 3,000 microns or less, 2,000 microns or less, 1,000 microns or less, or 500 microns or less) exclusive of any optional coating applied to the microtablets or micropellets. Methods for preparing microtablets or micropellets (e.g., enteric-coated microtablets or micropellets) comprising DMF are known in the art, for example, as described in U.S. Pat. No. 6,509,376 and incorporated by reference in its entirety herein.

In some embodiments, the first dosage component comprises an acid soluble outer coating. For example, in some embodiments, the first dosage component is in the form of enteric-coated microtablets or micropellets, and the enteric-coated microtablets or micropellets are encapsulated with an acid soluble coating, e.g., in a soft-shell or hard-shell gelatin capsule.

Other suitable acid soluble coatings for the first dosage component are known in the art and include those coatings that dissolve at a pH less than 6.0. Non-limiting examples of acid soluble coatings include gelatin, Eudragit® E-100, polyvinyl acetyl diethylaminoacetate, and chitosan coatings.

The acid-soluble coating may be applied using various techniques (e.g., spray techniques) known to one skilled in the art.

The first dosage component may also comprise one or more pharmaceutically acceptable excipients in addition to those described above. Suitable pharmaceutically acceptable excipients are those known in the art, for example, binders, fillers, disintegrants, glidants, lubricants, diluents, plasticizers, etc. as described in Remington's Pharmaceutical Science, 18$^{th}$ Edition, 1990, Mack Publishing Company, Easton, Pa. ("Remington's").

Second Dosage Component

The second dosage component is a controlled release dosage form described above in the third aspect or any embodiments described therein (e.g. the gastroretentive folded dosage forms described in the third aspect of the invention). In some embodiments, the only active ingredient in the second dosage form is DMF.

In some embodiments, suitable amounts of API for the second dosage component include those that can provide, by itself or in combination with one or more doses from, for example, a first dosage component, a daily amount of the respective compound (e.g., DMF) ranging from about 1 mg/kg to about 50 mg/kg (e.g., from about 2.5 mg/kg to about 20 mg/kg or from about 2.5 mg/kg to about 15 mg/kg).

Suitable doses of DMF for the second dosage component may be any therapeutically effective dose, e.g., an amount that is effective in treating multiple sclerosis. For example, suitable doses of DMF for the second dosage component may be any dose from 20 mg to 1 g of DMF. In some embodiments, the suitable doses of DMF in the second dosage component may be any dose from about 80 mg to about 1000 mg of DMF. In some embodiments, the suitable doses of DMF in the second dosage component may be any dose from about 100 mg to about 750 mg of DMF. In some embodiments, the suitable doses of DMF in the second dosage component is about 200 to about 600 mg. In some embodiments, the suitable doses of DMF in the second dosage component may be any dose from about 300 to about 600 mg.

In some embodiments, the DMF in the second dosage component is about 60 mg, about 80 mg, about 100 mg, about 120 mg, about 160 mg, about 200 mg, about 240 mg, about 320 mg, about 360 mg, about 400 mg, about 480 mg, about 600 mg, about 720 mg, about 800 mg, about 900 mg, about 1000 mg of DMF, or any ranges thereof.

The second dosage component can contain an amount of a compound that that can metabolize into MMF that provides an equivalent amount of MMF as the doses of DMF described above.

In some embodiments, the second dosage component comprises an acid soluble outer coating as described for the first dosage component.

Relationship of First and Second Dosage Components

In some embodiments, the first dosage component and the second dosage component are both part of a capsule. In some embodiments, the second dosage component is a floating capsule comprising an acid soluble cap (e.g., gelatin cap), and the first dosage component is placed between a pulsatile coating or layer of the second dosage component and the acid soluble cap (e.g., gelatin cap). Upon oral administration, the acid soluble cap (e.g., gelatin cap) is dissolved in the gastric fluid and releases the first dose of drug (e.g., DMF) from the first dosage component. At the same time, the second dosage component floats in the gastric fluid and is slowly eroded by the gastric fluid until a pulsatile coating or layer is disintegrated and releases the second dose of drug (e.g., DMF).

In some embodiments, the first dosage component encapsulates the second dosage component. In some embodiments, the first dosage component is further encapsulated by an acid soluble coating. In some embodiments, the second dosage component comprises an outer acid resistant coating.

In some embodiments, the first dosage component and the second dosage components are not physically attached to each other (e.g., as two capsules, two tablets, or one capsule and one tablet), which are provided (e.g., packaged) in a kit (e.g., a blister pack). For example, in some embodiments, the first dosage component is a non-gastro-retentive capsule (e.g., containing 120 mg or 240 mg DMF) and the second dosage component is a controlled release dosage form (e.g., as described herein). Thus, oral administration of the unit dosage form requires orally administering a non-gastro-retentive capsule (e.g., containing 120 mg or 240 mg DMF) and one controlled release dosage form (e.g., as described herein) at the same or substantially the same time as a single dose.

In another embodiment, the unit dosage form is a gastroretentive folded dosage form comprising an immediate-release component and a controlled release component. These dosage forms comprise an internal layer or compartment and at least two outer membranes as described above in the second embodiment of the third aspect of the present invention, and additionally comprise one or more immediate release layers covering the outer membranes and comprising DMF (e.g., DMF coated particles described in the second aspect invention or any embodiments described therein) and a soluble polymer that provides for the immediate release of DMF. Examples of soluble polymers that can be used in the immediate release which can be selected from soluble cellulose derivatives, i.e. methyl cellulose, hydroxypropyl cellulose, hydroxyethyl cellulose, hypromelose; various grades of povidone; polyvinyl alcohol and its derivatives, i.e. Kollicoat IR; soluble gums and others. The films may further comprise surface-active agents, plasticizers and humectants, such as PEGs, different grades of polysorbates and sodium lauryl sulfate, for example.

In another embodiment, the unit dosage form are for the immediate release and the sustained release of DMF in the gastrointestinal tract and comprise: i.) an internal layer or compartment comprising the DMF coated particles of the present invention (e.g., those described in the second embodiment or any specific embodiments described above) and a polymer; ii.) two membranes forming together an envelope around the inner membrane, each comprising at least one polymeric combination of a polymer which is not soluble in gastric juice, and a hydrophilic swelling polymer, and at least one plasticizer; and iii.) one or two layers comprising DMF (e.g., the DMF coated particles described in the second embodiment or any specific embodiments described therein) and a soluble polymer that provides for the immediate release of DMF and is attached to the outside of one outer membrane or both outer membranes or part of an outer membrane. Optionally an additional layer may be covering each immediate release membrane comprising a powder or a film that prevents adherence of the outer membrane or IR membrane onto itself when folded inside the capsule. In some embodiments, the immediate-release membranes possess surface properties that prevent adherence onto itself when folded inside the capsule.

While the internal layer and outer layer are generally welded together, the immediate release layer will not generally require such a strong connection with the rest of the GRDF device. Rather the immediate release formulation will quickly dissolve in order to deliver the drug of interest. The immediate release layer may be affixed to the outside of the GRDF using a compatible solvent, ultrasonic welding, or other means.

The ability to add an additional immediate release layer is particularly helpful in the development of once a day dosage forms. By combining the immediate and controlled release nature of the current invention, one can alter DMF release profile. Consequently, patients may receive both an immediate bolus of DMF as well as a prolonged delivery of DMF with the purpose of establishing therapeutic levels of the drug quickly and maintaining these levels for prolonged period of time, up to 24 hour.

Coating

As an additional method of delivering the immediate release of the drug, a coating may be applied to the capsule comprising the drug. Upon entry into the stomach, the coating will immediately allow release of the drug and enhance the release profile of the drug. Methods for applying coating to a capsule arc well known to those of skill in the art.

In one embodiment, the unit dosage form of the present invention comprises:

a first dosage component comprising a first dose of DMF, wherein the first dosage component is an enterically coated immediate release dosage form; and a second dosage component comprising a second dose of DMF, wherein the second dose of DMF in the unit dosage form is retained in the stomach a subject treated for at least 3 hours, wherein the second dosage component is any gastroretentive folded dosage forms described in the third aspect of the invention.

In one embodiment, the gastrorentive folded dosage form is as described in the third embodiment described above. More specifically, the gastrorentative folded form is a delayed pulse release dosage form described in the first specific embodiment above. In another more specific embodiment, the gastrorentative folded form is a delayed sustained release dosage form described in the second specific embodiment above.

In certain embodiments, the first dosage component and the second dosage component are not physically attached to each other (e.g., as two capsules, two tablets, or one capsule and one tablet), which are provided (e.g., packaged) in a kit (e.g., a blister pack).

Unit Dosage Form Comprising More than Two Dosage Components

In some embodiments, the unit dosage form is configured to have more than two dosage components, e.g., to provide a sustained release, or more than two pulses of releases of the API. In some embodiments, the unit dosage form comprising the first and second dosage components further comprises one or more dosage components comprising one or more doses of the API, wherein upon oral administration of the unit dosage form to a subject, the first, second, and the one or more doses of the API, are delivered to GI tract (e.g., upper GI tract or lower GI tract) of the subject in a sustained or pulsatile manner. The time between two consecutive pulses (e.g., between the first and second pulse, or the second and third pulses, etc.) in a pulsatile delivery system may be the same or different, each may be about 2 hours, about 4 hours, about 6 hours, about 8 hours, about 10 hours, about 12 hours, about 14 hours, or any ranges thereof.

4. Method of Treatment

DMF and its active metabolite MMF have been indicated as useful for the treatment or prophylactic treatment of various diseases or disorders. Thus, in some embodiments, the invention also provides a method of treatment of diseases or disorders where administering DMF is helpful, the method comprising orally administering to a subject in need thereof a unit dosage form (e.g., as described herein) once per day (i.e., QD dosing). In some embodiments, the invention also provides a method of treatment or prophylactic treatment of diseases or disorders where administering DMF is helpful, the method comprising orally administering to a subject in need thereof a pharmaceutical composition comprising DMF particles described in the first aspect of the invention or DMF coated particles described in the second aspect of the invention. The pharmaceutical composition of the present invention comprises the DMF particles or the DMF coated particles of the present invention and a pharmaceutically acceptable carrier or excipient.

The treatment may be acute or chronic (e.g., more than 1, 2, 3, 4, 5, 8, 10, or 12 weeks) treatments.

In some embodiments, the disease or disorder where administering DMF is helpful is:

an autoimmune disease selected from the group consisting of polyarthritis, rheumatoid arthritis, multiple sclerosis, graft-versus-host reactions, juvenile-onset diabetes, Hashimoto's thyroiditis, Grave's disease, systemic Lupus erythematodes (SLE), Sjogren's syndrome, pernicious anaemia and chronic active (=lupoid) hepatitis, psoriasis, psoriatic arthritis, neurodermatitis and enteritis regionalis Crohn;

a mitochondrial disease selected from the group consisting of Parkinson syndrome, Alzheimer's disease, Chorea Huntington disease, retinopathia pigmentosa or forms of mitochondrial encephalomyopathy;

a NF-kappaB mediated diseases selected from the group consisting of progressive systemic sclerodermia, osteochondritis syphilitics (Wegener's disease), cutis marmorata (livedo *reticularis*), Behcet disease, panarteriitis, colitis ulcerosa, vasculitis, osteoarthritis, gout, artenosclerosis, Reiter's disease, pulmonary granulomatosis, types of encephalitis, endotoxic shock (septic-toxic shock), sepsis, pneumonia, encephalomyelitis, anorexia nervosa, hepatitis (acute hepatitis, chronic hepatitis, toxic hepatitis, alcohol-induced hepatitis, viral hepatitis, jaundice, liver insufficiency and cytomegaloviral hepatitis), Rennert T-lymphomatosis, mesangial nephritis, post-angioplastic restenosis, reperfusion syndrome, cytomegaloviral retinopathy, adenoviral diseases such as adenoviral colds, adenoviral pharyngoconjunctival fever and adenoviral ophthalmia, AIDS, Guillain-Barré syndrome, post-herpetic or post-zoster neuralgia, inflammatory demyelinising polyneuropathy, mononeuropathia multiplex, mucoviscidosis, Bechterew's disease, Barett oesophagus, EBV (Epstein-Barr virus) infection, cardiac remodeling, interstitial cystitis, diabetes mellitus type II, human tumour radiosensitisation, multi-resistance of malignant cells to chemotherapeutic agents (multidrug resistance in chemotherapy), granuloma annulare and cancers such as mamma carcinoma, colon carcinoma, melanoma, primary liver cell carcinoma, adenocarcinoma, kaposi's sarcoma, prostate carcinoma, leukaemia such as acute myeloid leukaemia, multiple myeloma (plasmocytoma), Burkitt lymphoma and Castleman tumour;

a cardiovascular disease selected from the group consisting of cardiac insufficiency, myocardial infarct, angina pectoris and combinations thereof;

a respiratory disease selected from the group consisting of asthma, chronic obstructive pulmonary diseases, PDGF induced thymidine uptake of bronchial smooth muscle cells, bronchial smooth muscle cell proliferation, and combinations thereof;

a neurodegeneration or neuroinflammation selected from the group consisting of Adrenal Leukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cerebral palsy, Cockayne syndrome, Corticobasal degeneration, Creutzfeldt-Jakob disease, Familial Fatal Insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjögren-Batten disease (also known as Batten disease), Spinocerebellar ataxia, Spinal muscular atrophy, Steele-Richardson-Olszewski disease, Tabes *dorsalis*, Toxic encephalopathy, LHON (Leber's Hereditary optic neuropathy), MELAS (Mitochondrial Encephalomyopathy; Lactic Acidosis; Stroke), MERRF (Myoclonic Epilepsy; Ragged Red Fibers), PEO (Progressive External Opthalmoplegia), Leigh's Syndrome, MNGIE (Myopathy and external ophthalmoplegia; Neuropathy; Gastro-Intestinal; Encephalopathy), Kearns-Sayre Syndrome (KSS), NARP, Hereditary Spastic Paraparesis, Mitochondrial myopathy, and Friedreich Ataxia; or a demyelinating neurological disorder selected from the group consisting of optic neuritis, acute inflammatory demyelinating polyneuropathy (AIDP), chronic inflammatory demyelinating polyneuropathy (CIDP), acute transverse myelitis, progressive multifocal leucoencephalopathy (PML), acute disseminated encephalomyelitis (ADEM) or other hereditary disorders (e.g., leukodystrophies, Leber's optic atrophy, and Charcot-Marie-Tooth disease).

In some embodiments, the disease or disorder where administering DMF is helpful is a neutrophil mediated disease or disorder (e.g., an allergic disease or disorder, an inflammatory disease or disorder, an autoimmune disease or disorder, or a tumor).

Non-limiting examples of autoimmune diseases or disorders include autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), or autoimmune skin blistering diseases (AIBD).

Non-limiting examples of autoimmune skin blistering diseases include epidermolysis bullosa acquistita (EBA), pemphigoid disease (e.g., bullous pemphigoid, mucous membrane pemphigoid, or pemphigoid gestationis), IgA-mediated bullous dermatoses (e.g., Dermatitis Herpetiformis or Linear IgA Bullous Dermatosis), and pemphigus disease (e.g., IgA Pemphigus).

Non-limiting neutrophil mediated diseases or disorders also include an inflammatory skin or subcutaneous disease selected from the group consisting of Pyoderma Gangrenosum, Erosive Pustular Dermatosis of the Scalp, Sweet's Syndrome, Bowel-associated Dermatosis-arthritis Syndrome, Pustular Psoriasis, Acute Generalized Exanthematous Pustulosis, Keratoderma Blenorrhagicum, Sneddon- Wilkinson Disease, Amicrobial Pustulosis of the Folds, Infantile Acropustulosis, Transient Neonatal Pustulosis, Neutrophilic Eccrine Hidradenitis, Rheumatoid Neutrophilic Dermatitis, Neutrophilic Urticaria, Still's Disease, Erythema *Marginatum*, Unclassified Periodic Fever Syndromes/Autoinflammatory Syndromes, Bullous Systemic Lupus Erythematosus, and Neutrophilic Dermatosis of the Dorsal Hands (Pustular Vasculitis);

Non-limiting neutrophil mediated diseases or disorders also include:

an allergic condition selected from the group consisting of anaphylaxis, allergic rhinitis and allergic asthma;

neutrophil mediated respiratory disease selected from the group consisting of lung cancer, severe asphyxic episodes of asthma, acute lung injury, and Acute Respiratory Distress Syndrome;

an acute tissue injury selected from the group consisting of acute kidney injury, ischemia reperfusion injury, sepsis, and septicemia with multiorgan failure;

an inflammatory bowel disease selected from the group consisting of ulcerative colitis, Crohn's disease, and inderteminate colitis; and sickle cell crisis or acute chest syndrome.

In some embodiments, the disease or disorder where administering DMF is helpful is a disease or disorder that is associated with aberrant PI3K/AKT signaling including cancer, chronic inflammation and allergy, neurodegerative disease, cardiovascular disease and metabolic diseases. Non-limiting examples of disease or disorders that are associated with aberrant PI3K/AKT signaling include all forms of cancer, precancerous lesions, cardiovascular disease, rheumatologic disease, pulmonary disease, dermatologic disease, gynecological diseases, vascular disease, neurologic disease, and infectious disease including bacterial, viral, retroviral, and parasitic diseases. In some embodiments, the disease or disorder to be treated is cancer. Non-limiting examples of cancer include breast cancer, lung cancer, ovarian cancer, uterine cancer, brain cancer, sarcoma, melanoma, leukemia, lymphoma, colorectal cancer, prostate cancer, and liver cancer. In some embodiments, the disease or disorder to be treated is rheumatologic disease, e.g., rheumatoid arthritis or osteoarthritis. In some embodiments, the disease or disorder to be treated is pulmonary disease, e.g., allergic rhinitis, chronic obstructive pulmonary disease (COPD).

In some embodiments, the disease or disorder where administering DMF is helpful is a disease or disorder that is associated with aberrant p38 MAPK signaling. Non-limiting examples of such diseases include COPD (including chronic bronchitis and emphysema), asthma, paediatric asthma, cystic fibrosis, sarcoidosis, idiopathic pulmonary fibrosis, allergic rhinitis, rhinitis, sinusitis, allergic conjunctivitis, conjunctivitis, allergic dermatitis, contact dermatitis, psoriasis, ulcerative colitis, inflamed joints secondary to rheumatoid arthritis or osteoarthritis, rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

In some embodiments, the invention provides a method of treating multiple sclerosis (e.g., relapsing-remitting MS, secondary progressive MS, primary progressive MS, progressive relapsing MS) in a subject in need thereof, wherein the method comprises administering to the subject a controlled release dosage form or an unit dosage form (e.g., as described herein) once per day.

In some embodiments, the unit dosage form comprises a first dosage component comprising a first dose of about 80 mg to about 360 mg (e.g., about 120 mg or about 240 mg) of an API; and a second dosage component comprising a second dose of about 80 mg to about 720 mg (e.g., about 120 mg or about 240 mg) of the API;

wherein when the unit dosage form is administered to a subject orally, the first and second doses of the API are delivered to the upper GI tract of the subject in a sustained or pulsatile manner.

In any of the embodiments described herein, the controlled release dosage form or unit dosage form may be administered to a subject with or without food.

In some embodiments, the first and second dosage components of the unit dosage form are physically separated from each other (e.g., as two capsules, two tablets, or one capsule and one tablet) and are provided in a kit (e.g., a blister pack). In some embodiments, the first and second dosage components of the unit dosage form are both part of one dosage form (e.g., a pill, a tablet, or a capsule).

In some embodiments, the only active ingredient in the controlled release dosage form or unit dosage form is DMF.

In some embodiments, the method comprises orally administering to the subject the controlled release dosage form or unit dosage form with or without food once per day, wherein the subject exhibits one or more of the following pharmacokinetic parameters: (a) a mean plasma MMF $AUC_{overall}$ ranging from about 4.81 h·mg/L to about 11.2 h·mg/L; (b) a mean plasma MMF $AUC_{0-12}$ ranging from about 2.4 h·mg/L to about 5.5 h·mg/L; and (c) a mean $AUC_{0-infinity}$ ranging from about 2.4 h·mg/L to about 5.6 h·mg/L. In some embodiments, the subject treated exhibits a pharmacokinetic profile characterized by both (a) and (b), both (a) and (c), or both (b) and (c). In some embodiments, the subject treated exhibits a pharmacokinetic profile characterized by (a), (b), and (c).

In some embodiments, the subject exhibits a mean MMF plasma area under the curve 0-12 ($AUC_{0-12}$) of about 2.36 h·mg/L to about 5.50 h·mg/L, from about 2.75 h·mg/L to about 5.10 h·mg/L, or from about 3.14 h·mg/L to about 4.91 h·mg/L. In some embodiments, the subject exhibits a mean $AUC_{0-12}$ of about 3.93 h·mg/L.

In some embodiments, the subject exhibits a mean MMF plasma overall area under the curve ($AUC_{overall}$) of about 4.81 h·mg/mL to about 11.2 h·mg/mL, or from about 6.40 h·mg/L to about 10.1 h·mg/L. In some embodiments, the subject exhibits a mean $AUC_{overall}$ of about 8.02 h·mg/L.

EXAMPLES

Example 1. General Description of Wet-Milling Process 50 kg Fumaric acid was added to the reactor followed by 229.3 kg methanol and 10.6 kg sulfuric acid. The reactor contents was heated to 62-65° C. (or reflux conditions) and held at that temperature for at least 3 h to allow conversion of fumaric acid to dimethyl fumarate product. At the end of hold period the solution is recirculated through a Silverson™ high-shear mixer (HSM) operated at 3400-3600 RPM while simultaneously cooled to terminal temperature 10-15° C. in a 4-10 h cooling ramp. The dimethyl fumarate particles which were crystallized out of solution initially (nucleation point) around 60-61° C. and throughout the cooling period were exposed to the shear actions during the recirculation from the reactor through the Silverson HSM. The shear actions broke the large particles to smaller particles. The milling maybe stopped when the particle size reaches the desired target. This can be determined based on in-process measurements and/or milling time or number of recirculation. After the milling completion, the slurry containing milled dimethyl fumarate was transferred to the filter or centrifuge to isolate the solids, the isolated solids were washed with 3-6×50 L methanol, and finally vacuum dried at 24-28° C. with nitrogen bleed until less than 1500 ppm residual methanol was achieved.

The dimethyl fumarate product obtained by the process and equipment described above has shown improved bulk powder properties relative to material produced using jet mill (dry mill). The improved powder rheology property can be associated among other things by two key factors below:

a. Powder uniformity and the presence of less fines particles with size less than 10 microns; Table 1 below show particle size distribution which shows smaller span (a measure of particle uniformity) for wet milled material compare to jet milled material (dry mill).

b. The differences in permeability as measured by FT4 (Freeman Technology) bulk powder testing. The powder permeability (see Table 2) can be associated to its tendency towards bridging or segregation which are highly undesired occurrences during the manufacture of drug product. The permeability number measures relative ease for air to travel through a conditioned powder bed; low number indicates high permeability and therefore less chances for bridging/segregation

TABLE 1

Particle Size of Dimethyl fumarate measured by Malvern Laser Diffraction.

|  | ≤10 µm | D × 10 (µm) | D × 50 (µm) | D × 90 (µm) | D × 97 (µm) | Span |
|---|---|---|---|---|---|---|
| Wet-Milled | | | | | | |
| 2014-4281-A.4 | 2.61% | 31.9 | 96 | 182 | 235 | 1.562 |
| 2014-4281-A.8 | 3.87% | 27.2 | 70.8 | 148 | 208 | 1.71 |
| 2014-4281-A.9 | 3.02% | 26.8 | 88.2 | 166 | 210 | 1.58 |
| A14DS0977 | 1.87% | 51.5 | 127 | 249 | 319 | 1.554 |
| A14DS0978 | 2.32% | 44.1 | 113 | 224 | 294 | 1.593 |
| A14DS1097 | 2.89% | 33.1 | 87.8 | 189 | 257 | 1.772 |
| Jet-Milled | | | | | | |
| 11P1310 | 11.48% | 9 | 30 | 70 | 97 | 2.05 |

* Batches 2014-4281-A.4, A.8 and A.9 are produced using a Silverson high-shear mixer. Batches A14DS0977, 0978 and 1097 are produced using a IKA high-shear mixer.

TABLE 2

Dimethyl Fumarate Rheology Properties measured by FT4

|  | Low Stress | | | High Stress | |
|---|---|---|---|---|---|
|  | Specific Energy | Flow Rate Index | Permeability (1 kpa) | Permeability (15 kpa) | Flow Function |
| Wet-Milled | | | | | |
| 2014-4281-A.4 | 4.87 | 1.11 | 0.05 | 0.10 | 5.84 |
| 2014-4281-A.8 | 6.64 | 1.37 | 0.04 | 0.12 | 3.29 |
| 2014-4281-A.9 | 6.42 | 1.33 | 0.09 | 0.18 | 2.50 |
| A14DS0978 | 8.67 | 1.68 | 0.15 | 0.17 | 12.84 |
| A14DS1097 | 9.19 | 1.54 | 0.15 | 0.18 | 5.97 |
| Jet-Milled | | | | | |
| B1417-140304 | 5.48 | 1.50 | 0.24 | 0.52 | 2.25 |

The improvement in powder flow for wet milled dimethyl fumarate has been also shown with drug product blends containing dimethyl fumarate and other excipients such as in the current FDA approved twice a day formulation. See FIG. 1.

Example 2. DMF Wet Milling—Large Scale Run 350 kg Fumaric acid in approximate 2100 L methanol and 77 kg sulfuric acid are heated to 60-65° C. (reflux conditions) and held at that temperature to convert the fumaric acid to dimethyl fumarate. After a period of hold time (at least 4 h) the product solution is polished filtered to the crystallizer. The hot product solution in the crystallizer is then recirculated through a silverson UHS450 high-shear mixer (HSM) and back to the crystallizer. The HSM is equipped with a choice of mill head or stator. Two stators type may be used, such as slotted disintegrating (medium stator) or square-hole high shear stator (fine stator). After the recirculation is established, the solution is cooled to 5-10° C. to crystallize the product out of solution while simultaneously milled in the HSM. The particle size reduction induced by the HSM is monitored by crystal chord length (CLD) measurements using FBRM (focused-beam reflective measurement) technology with probe positioned in either/and both the recirculation line or in the vessel. The recirculation (milling) is discontinued when the target CLD is achieved such as when the median value of a mean-square weighted CLD distribution is less than 100 µm. Subsequently, the milled DMF is isolated using a filter centrifuge and dried to yield the final product.

The results of powder characterization for two 350 kg batches obtained with two different mill head are summarized in table below:

TABLE 3

|  | Run 1 | Run 2 |
|---|---|---|
| Mill Head/Stator Type | Slotted-Disintegrating | Square-hole high-shear |
| Analysis by Laser Diffraction: | | |
| $d_{10}$ | 35 µm | 39 µm |
| $d_{50}$ | 83 µm | 83 µm |
| $d_{90}$ | 156 µm | 150 µm |
| Powder Characterization by FT4: | | |
| Flow rate Index (FRI) | 1.61 | 1.39 |
| Specific Energy (mJ/g) | 12.21 | 12.18 |
| Permeability at 1 kPa (mbar) | 0.31 | 0.31 |
| Permeability at 15 kPa (mbar) | 0.33 | 0.34 |
| Flow Function (FF) | 10.3 | 4.95 |

Example 3. DMF Powder Characterization

DMF powder characterization was conducted using the FT4 Powder Rheometer (Freeman Technology Ltd, Tewkesbury, UK) using the 25 mm vessel assembly which consists of 23.5 mm diameter blades, vented piston, a segmented rotational shear cell accessory; and a 10 or 25 ml borosilicate vessel. All powders were pre-conditioned by the instrument's built-in conditioning step.

Powder testing can be generally classify into three testing category, such as: dynamic tests to determine flow rate index (FRI) and specific energy (SE), permeability tests to measure air transmission through a powder bed, and shear test to determine flow function (FF) which is an indication of powder flow properties under stress. Below are further descriptions of the tests.

Dynamic Testing

Dynamic testing used the 23.5 mm diameter blades and a 25 ml powder sample in the borosilicate test vessel. Powder was filled into the vessel. The blades were simultaneously rotated and moved axially into the powder sample as the axial and rotational forces were measured and used to calculate the dynamic flowability parameters. Among dynamic parameters tested are Flow rate Index (FRI) and Specific Energy (SE). Their measurement techniques are described below:

Flow Rate Index (FRI):

The FRI is a measure of a powder's sensitivity to variable flow rate and it is obtained as the ratio of the total energy required to induce powder flow at 10 mm/s and 100 mm/s blade tip speed. A larger deviation from 1 indicates greater sensitivity of a powder to variable flow rate.

Specific Energy (SE)

SE is a measure of the powder flow in low stress environment and is derived from the shear forces acting on the blades as they rotate upward through the powder. The SE is recorded as the flow energy of the powder normalized by its weight in mug during the upward spiral movement of the blades. A lower SE is an indication of a less cohesive powder and better flow properties.

Permeability Testing

The permeability test measures the ease of air transmission through a bulk powder which can be related to the powder's flowability. The permeability testing used a vented piston with an aeration base and a 10 ml powder sample in the borosilicate test vessel. Powder was filled into the vessel. The powder bed with a vented piston is exposed to varying normal stresses increased stepwise from 1 kPa to max 15 kPa. The pressure drop across the powder bed was measured while air was flushed through the powder at a constant velocity of 2 mm/s. The pressure drop values recorded in mBar at the lowest, 1 kPa, and highest, 15 kPa, A lower pressure drop is indicative of higher permeability and usually, better flow properties.

Shear Testing

Shear testing measures powder shear properties which involves the stress limit required to initiate a powder flow. The shear testing used a segmented rotational shear cell head and a 10 ml powder sample in the borosilicate test vessel. Powder was filled into the vessel. The shear cell head was simultaneously rotated and moved axially unto the powder sample at pre-determined normal stresses as the shear stresses were measured to calculate several parameters that include the flow function (FF) and powder cohesion (in kPa). Usually, powders of low cohesion have higher FF and that represents better flow properties.

Example 4. Comparison of Morphology for Jet Milled and Wet Milled DMF

Figure 2:
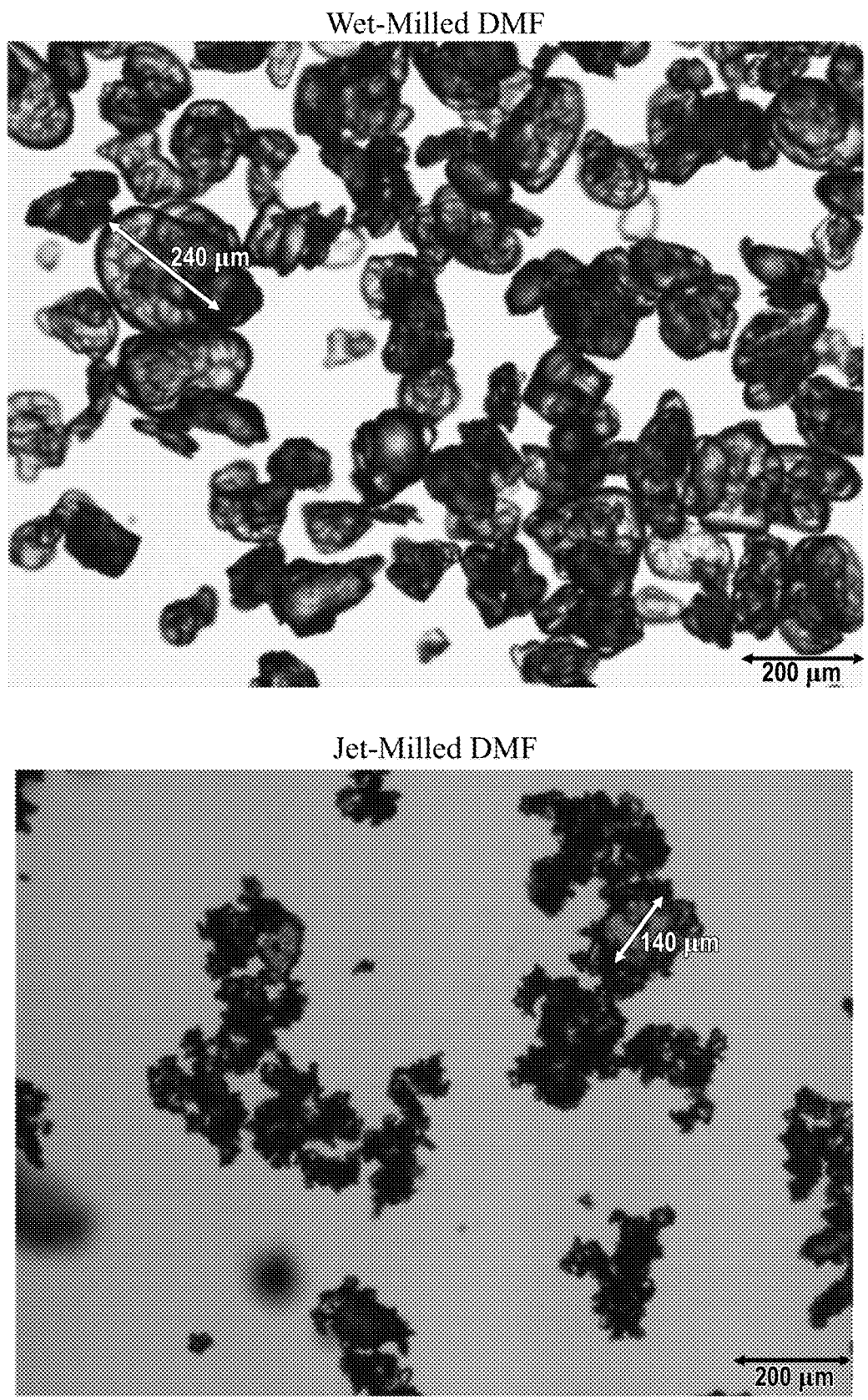
FIG. 2 shows particle images for wet-milled dimethyl fumarate and jet-milled dimethyl fumarate.

Two DMF lots produced by jet milling and wet milling are compared using Malvern Instrument Morphologi G3. Images of both particles are shown in FIG. 2.

Figure 3:
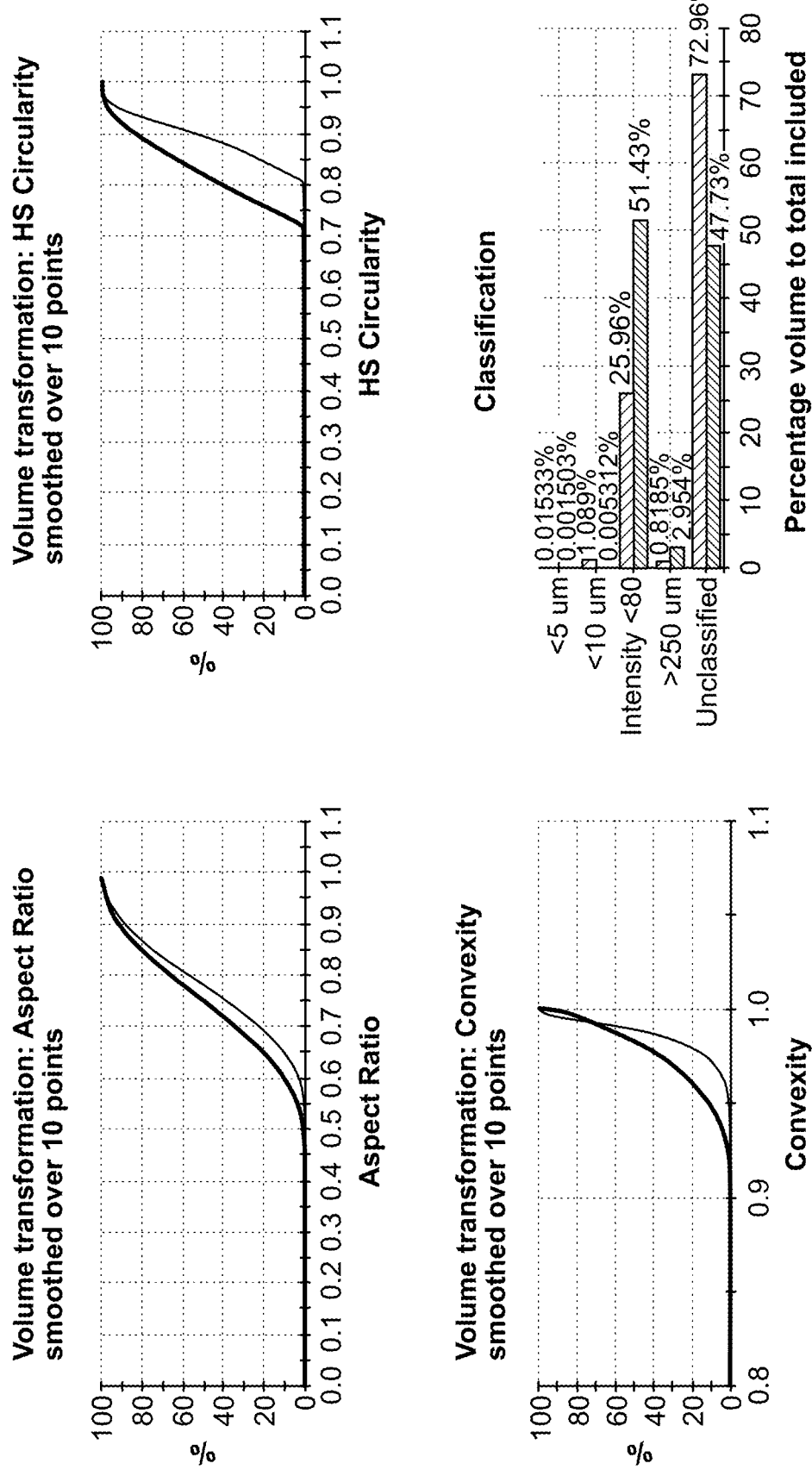
FIG. 3 shows various morphology properties for wet-milled DMF and jet-milled DMF.

G3 morphologi analyzes morphological features of each individual particle in the sample in term of aspect ratio, circularity, and convexity. The results are shown in FIG. 3.

The measurement with G3 morphologi reveals that wet milled material is slightly less elongated, more circular and less edgy, as indicated by higher aspect ratio, higher HS circularity and higher convexity values, respectively, as compared to the jet milled material. In addition, wet milled material contained more thick particles, which was indicated by the higher percentage of particles with intensity <80.

Example 5. Method of Preparing DMF Coated Particles

1) Experimental Method

The enteric coated DMF is prepared using a Glatt GPCG-2 fluid bed granulator with a 6' Wurster column. Dissolution was run with USP apparatus II by the Pharmaceutical Analytical Development Department with the following method.

TABLE 4

| Dissolution method | |
|---|---|
| Method | USP Apparatus II (paddle) |
| Dissolution media | Acid Stage: 0.1N HCl |
| | Buffer Stage: SIF without pancreatin, pH 6.8 |
| Dissolution Volume (mL) | 500 |
| Temp (° C.) | 37 ± 0.5 |
| Rotation Speed (rpm) | 100 |
| Sampling | Auto Sampler: |
| Replicate | N = 2 |

2) Sample Preparation

DMF first de-lumped with a Frewitt Comill with screen size 1.0 mm. Then, it is mixed with silicon dioxide (Aerosil) and being fluidize in the fluid bed granulator for 5 minutes.

TABLE 5

| Powder formulation | |
|---|---|
| Ingredients | Weight % |
| DMF | 99.5 |
| Aerosil 200 | 0.5 |

Eudragit L100 and triethyl citrate is used for coating an enteric layer for stomach acid protection on the DMF API particles. Samples were taken at different L100 weight gain to compare gastric protection capability.

TABLE 6

| Enteric coat formulation | |
|---|---|
| Ingredients | Weight % |
| Eudragit L100 | 6.5 |
| IPA | 90.7 |
| Water | 1.5 |
| Triethyl citrate | 1.3 |

The coating parameters are as follow:

TABLE 7

| Coating parameters | | | |
|---|---|---|---|
| Airflow (m3/hr) | Product temp (° C.) | Spray rate (g/min) | Atom pressure (bar) |
| 40 | 22-25 | 15-20 | 2.5 |

Figure 5:
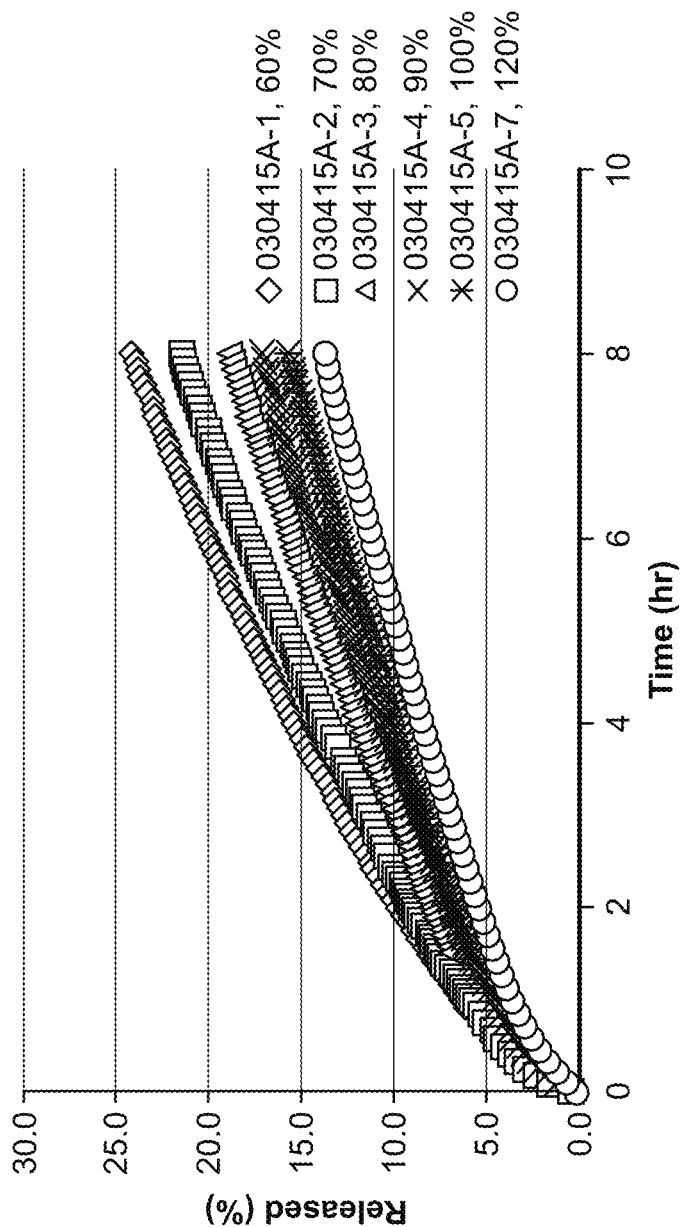
FIG. 5 shows DMF release profile for coated DMF particles in Simulated Gastric Fluid (SGF).
Figure 6:
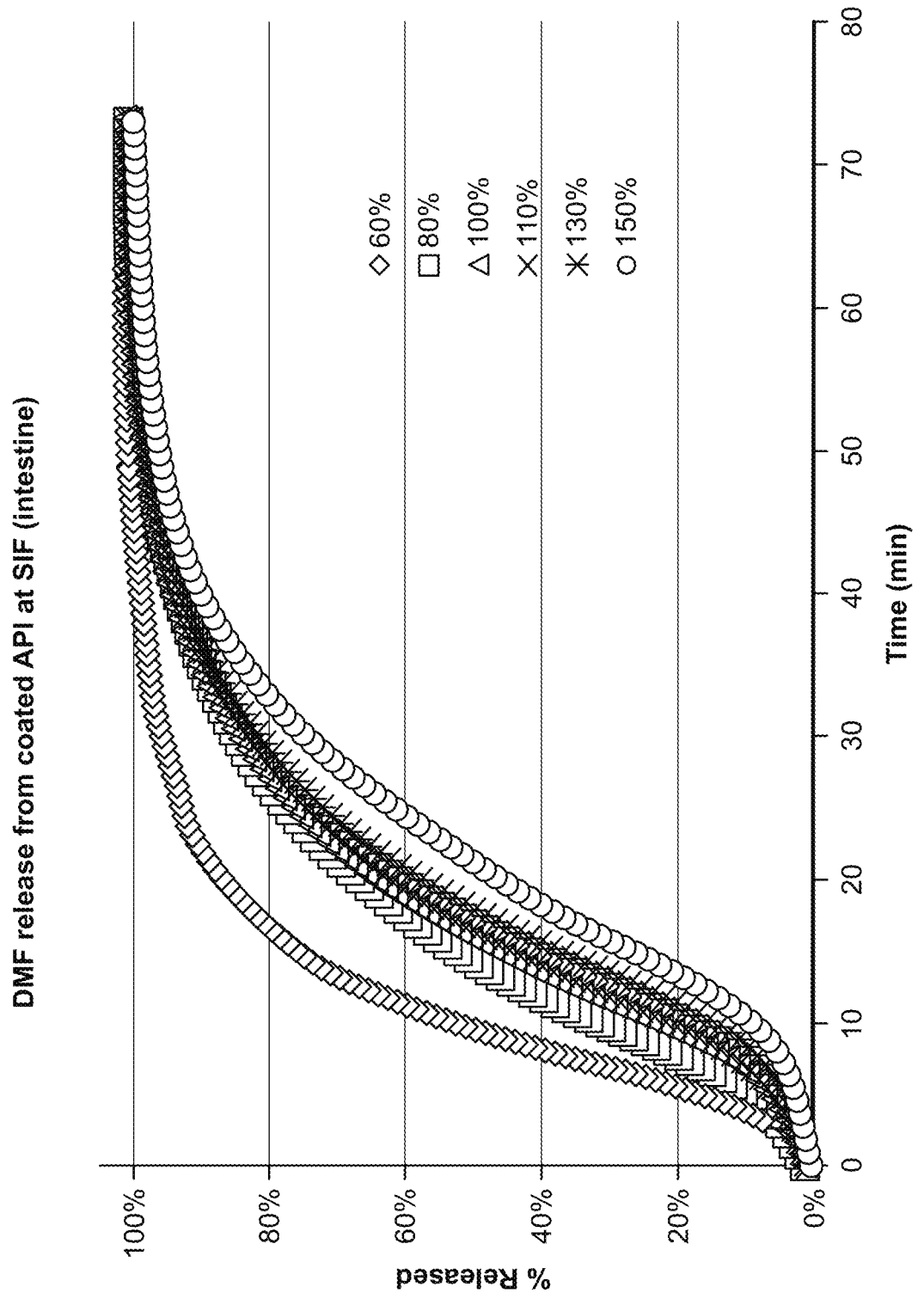
FIG. 6 shows DMF release profiled for coated DMF particles of the present invention in Simulated Intestine Fluid (SW).

FIG. 4 shows the SEM images of uncoated DMF and enterically coated DMF. FIGS. 5 and 6 show dissolution profiles for DMF coated particles in SGF and SIF.

Example 6. Comparison of Enteric Coated DMF Using Unmilled Coarse DMF Versus Wet-Milled DMF Unmilled coarse DMF were coated according to the method of described in Example 5. Various properties of the unmilled coarse DMF and enterically coated DMF are compared with wet-milled DMF and enterically coated DMF made from wet-milled DMF. See Table 8.

TABLE 8

Figure 7B:
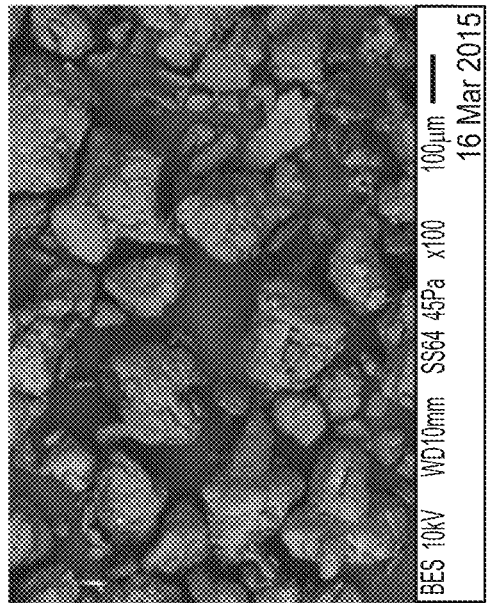
FIG. 7B shows SEM image of wet-milled DMF.
Figure 7D:
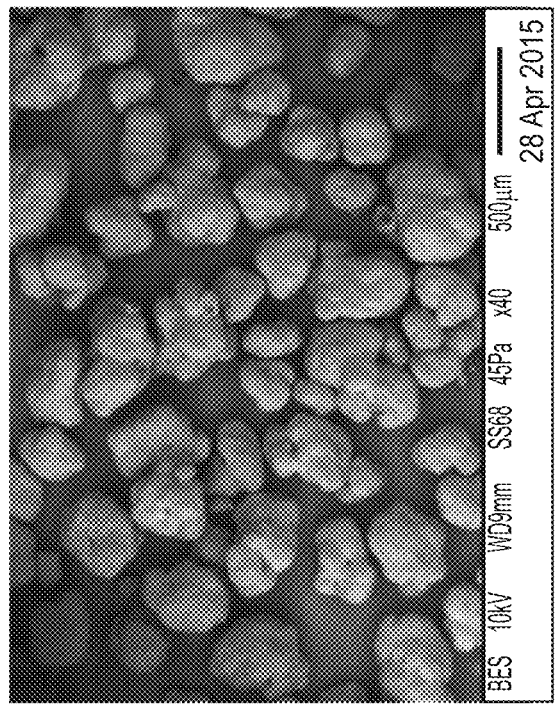
FIG. 7D shows SEM images of coated DMF particles using wet-milled DMF of the present invention.
Figure 7A:
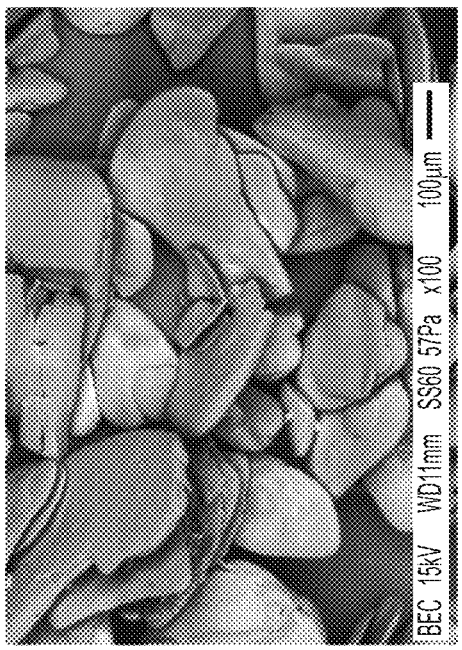
FIG. 7A shows SEM images of unmilled coarse DMF.
Figure 7C:
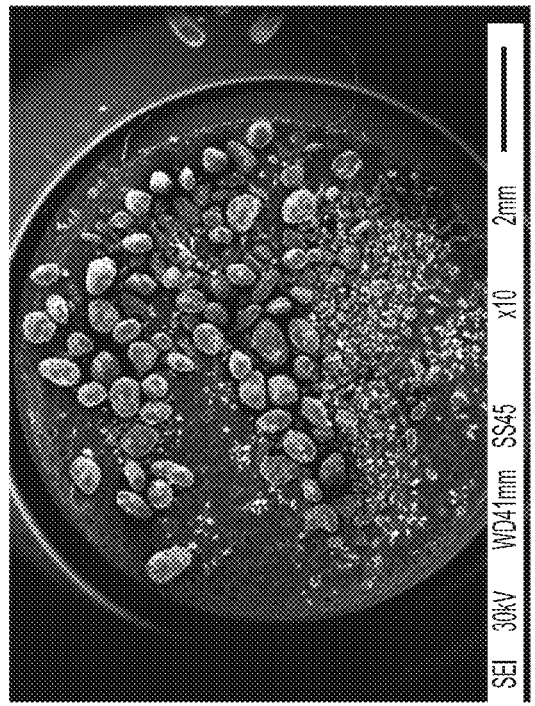
Figure 9:
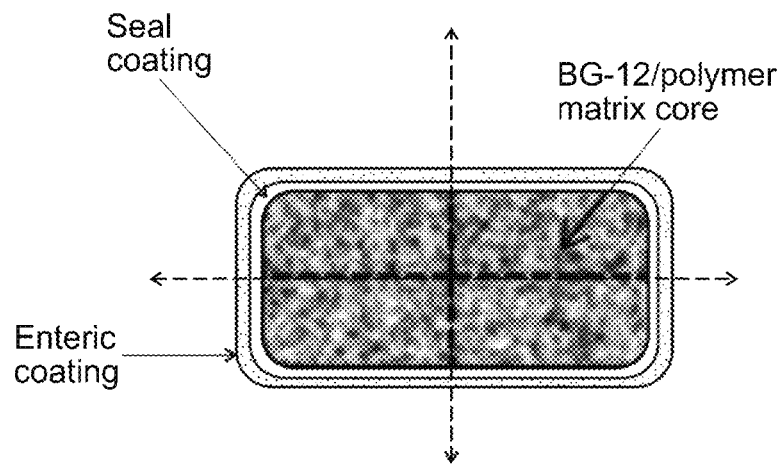
FIG. 9 shows a design of a polymer matrix system which contains a core containing DMF and a polymer, a seal coating encapsulating the core, and an outer enteric coating. In this design, DMF may be released through matrix erosion over a sustained period of time (e.g., about 6 hours.)
Figure 10:
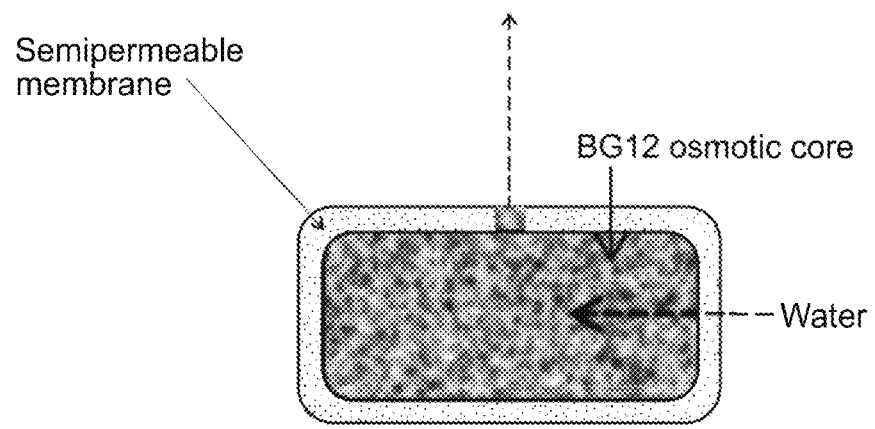
FIG. 10 shows a design of an osmotic dosage form which contains an osmotic core containing DMF and a semipermeable membrane coating encapsulating the core. The semipermeable membrane allows water into the tablet which creates osmotic pressure that forces the drug out of the coated tablet through a laser drilled hole in the coating. In this design, DMF may be released over a sustained period of time (e.g., about 6 hours).
Figure 11A:
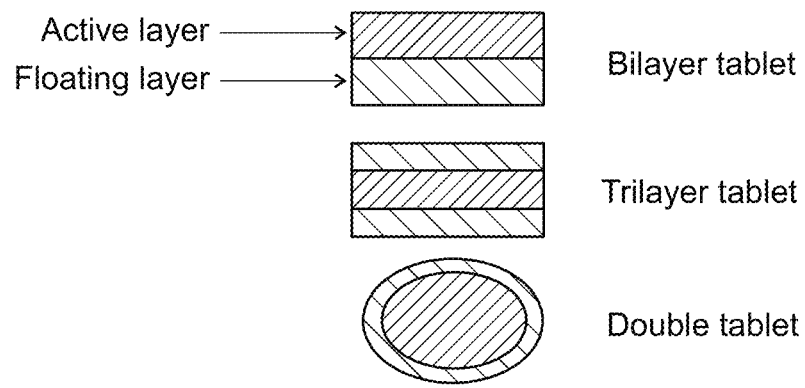
FIG. 11A shows three different designs of a floating dosage formulation: a bilayer, a trilayer, and a double tablet. Each design has an active layer, which contains DMF, and a floating layer. The bilayer design contains only one active layer and one floating layer. The trilayer design contains two floating layers and one active layer in between. The double tablet design has the floating layer encapsulating the active layer.
Figure 11B:
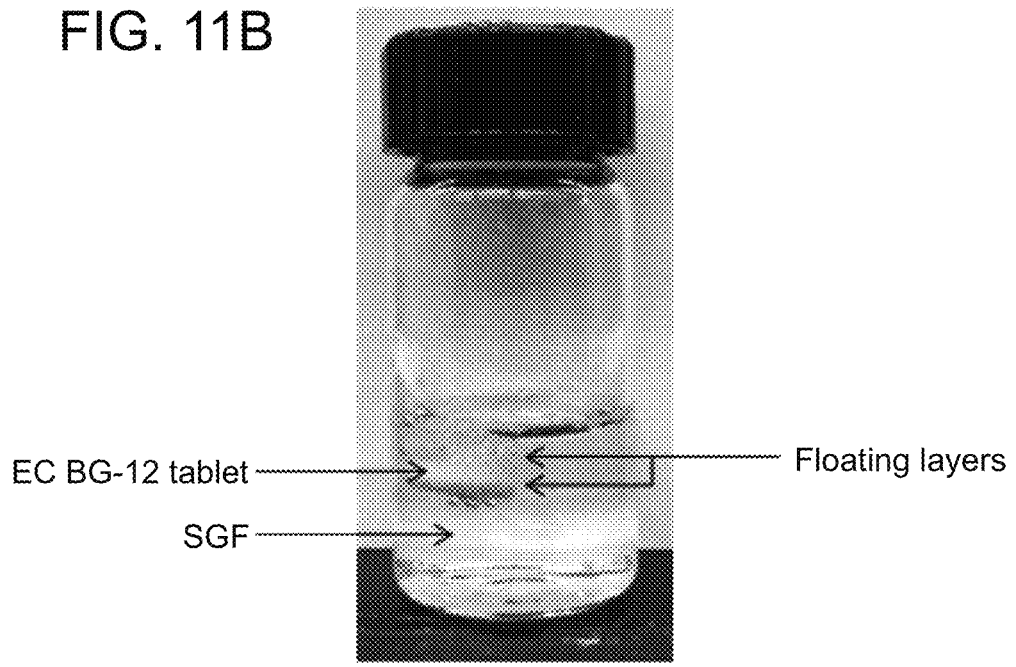
FIG. 11B shows a picture of a trilayer floating tablet, which contains two effervescent floating layer with one enterically coated active layer containing DMF, floating in simulated gastric fluid.
Figure 12A:
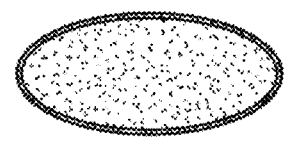
FIG. 12A shows a design of swellable tablet formulation for sustained release. The swellable tablet contains an API (e.g., DMF) that is seal coated and enterically coated and one or more swelling polymers.
Figure 12B:
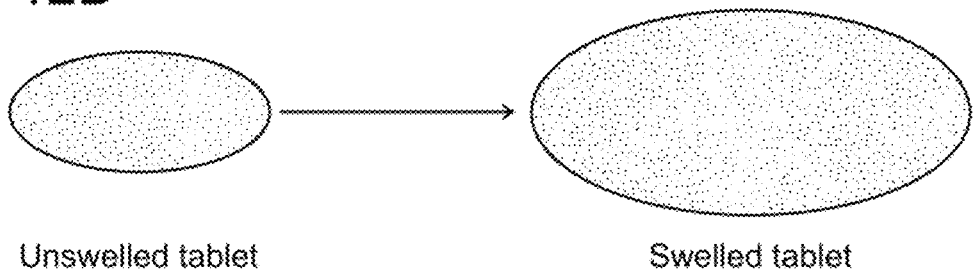
FIG. 12B shows that the swellable tablet can expand significantly which allows the swelled tablet to be retained in the stomach of a subject treated.
Figure 12C:
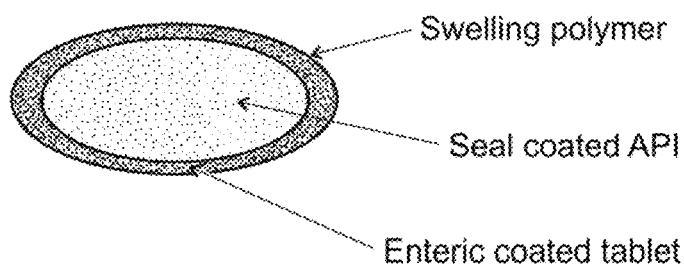
FIG. 12C shows a design of swellable tablet formulation for delayed release. The swellable tablet contains a core containing an API (e.g., DMF) that is seal coated and enterically coated and one or more swelling polymers encapsulating the core.
Figure 12D:
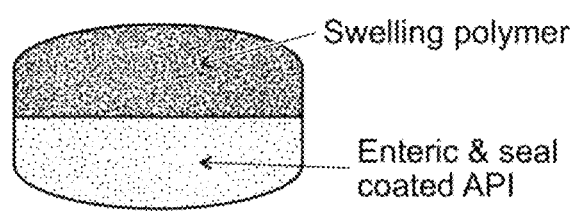
FIG. 12D shows another design of swellable tablet formulation for delayed release. The swellable tablet contains two layers: an active layer containing an API (e.g., DMF) that is seal coated and enterically coated and a swelling layer containing one or more swelling polymers. The two layers are joined together to form a bilayer tablet structure.
Figure 13A:
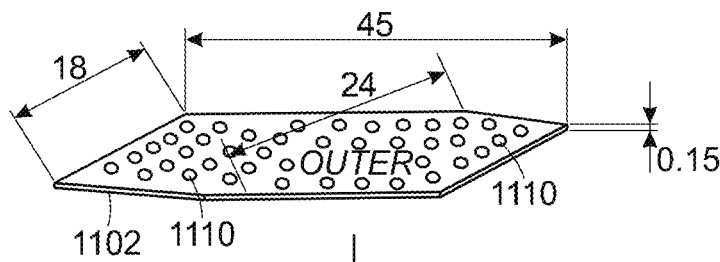
FIG. 13A-13E shows a side view of components (FIGS. 13A-13D) in the gastroretentive folded device (FIG. 13E) of the present invention before the components are folded.
Figure 13B:
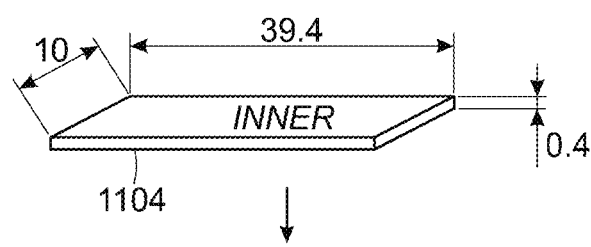
Figure 13C:
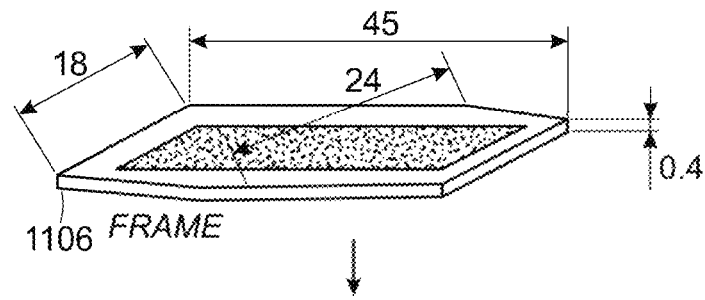
Figure 13D:
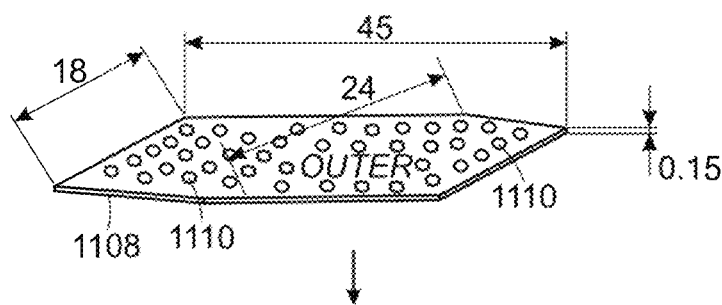
Figure 13E:
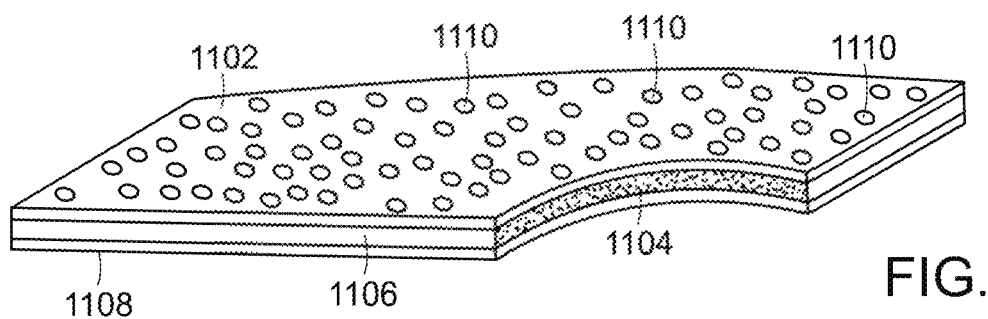
Figure 14A:
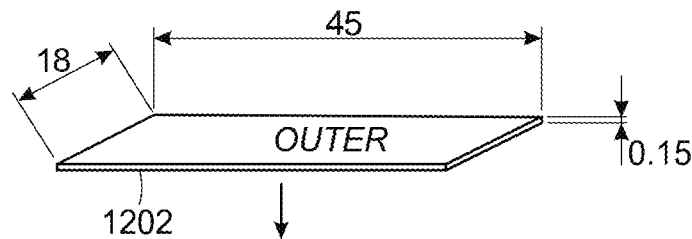
FIG. 14A-14E shows a side view of components (FIGS. 14A-14D) in the gastroretentive folded device (FIG. 14E) of the present invention before the components are folded. The DMF coated particles are incorporated into separate compartments (FIG. 14B) to form the integrated device.
Figure 14B:
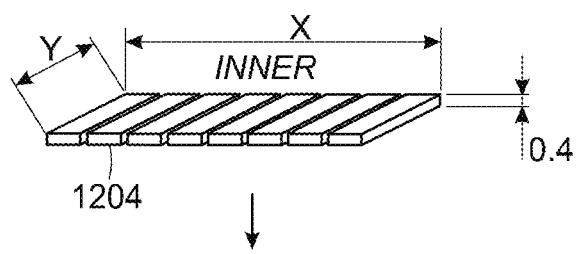
Figure 14C:
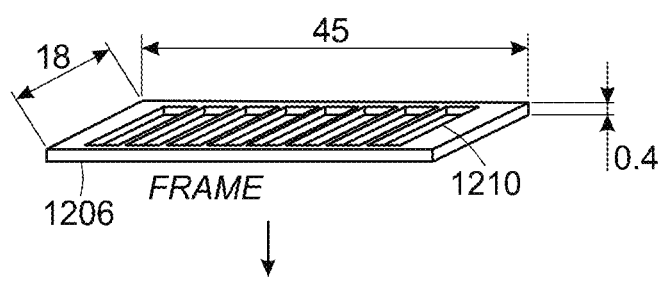
Figure 14D:
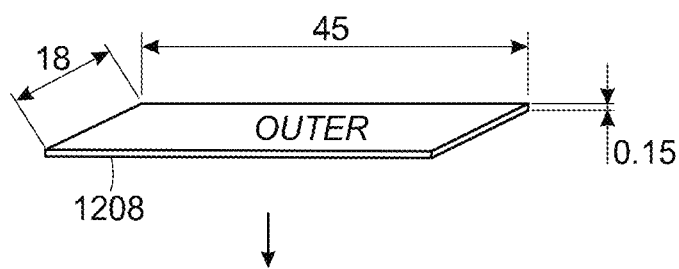
Figure 14E:
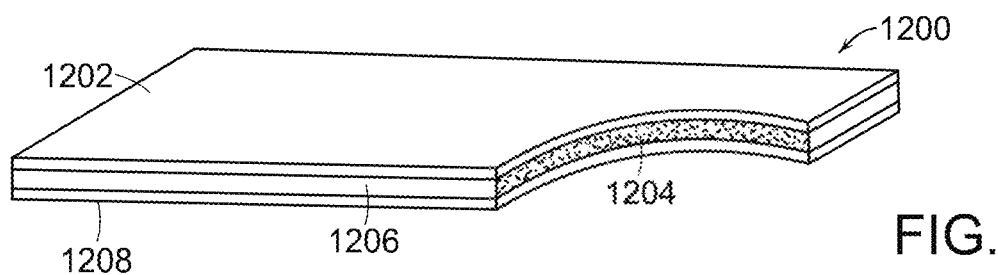
Figure 15A:
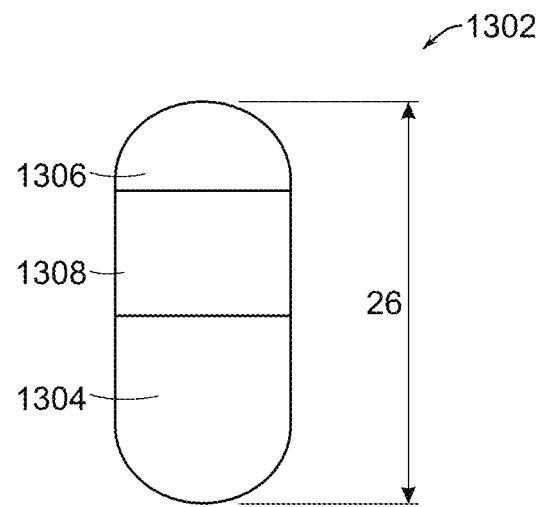
FIGS. 15A and 15B shows a side and cross-sectional view of a gastroretentive folded device of the present invention.
Figure 15B:
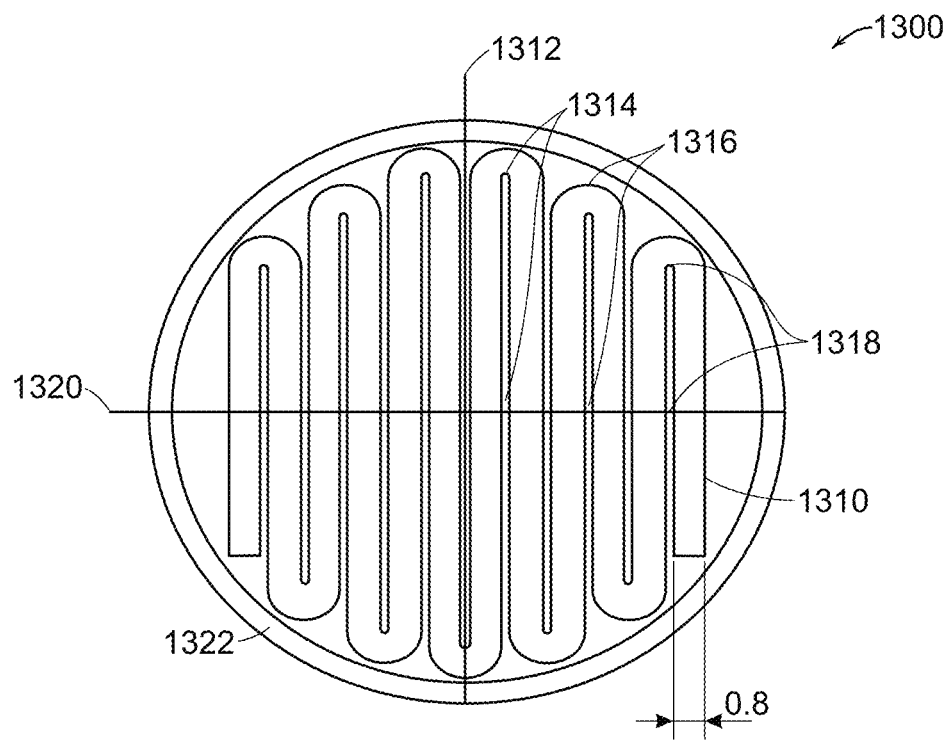
Figure 16A:
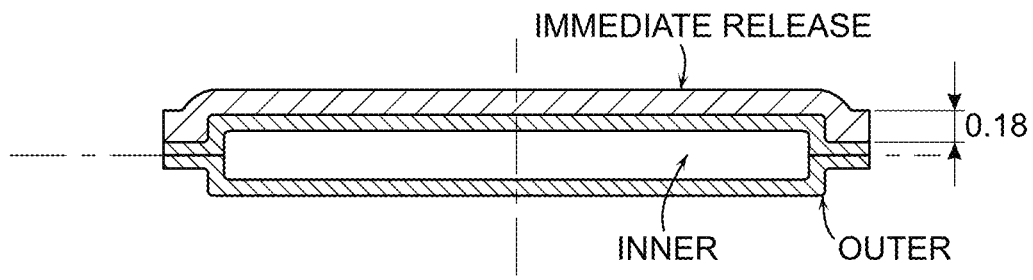
FIG. 16A shows the placement of a single immediate release layer on top of the outer layer of a gastroretentive folded device of the present invention in a cross section view.
Figure 16B:
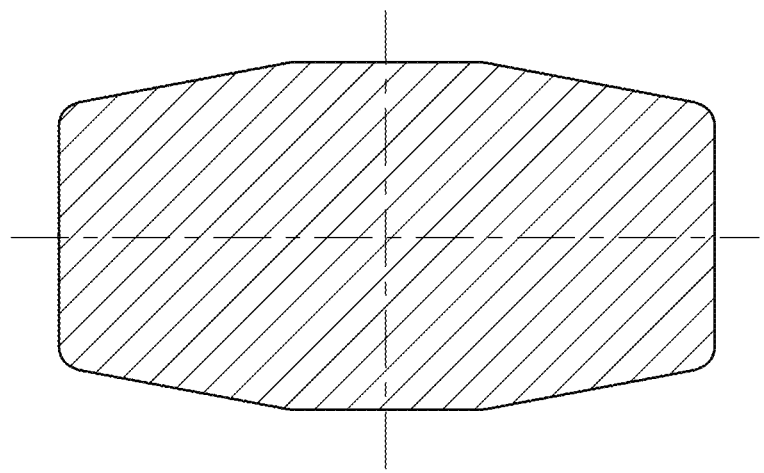
As shown in FIG. 16B, the immediate release layer covers the entire surface of the device.
Figure 17A:
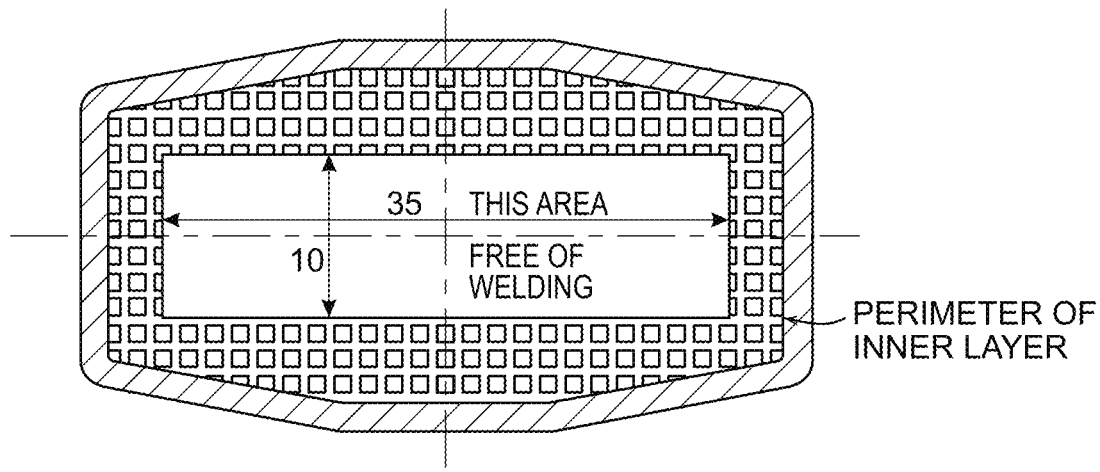
FIG. 17A shows a drawing of the ultrasound welding on a gastroretentive folded device of the present invention. The perimeter line of the internal layer is shown with an arrow and the extend of welding in a cross section is provided in FIG. 17B.
Figure 17B:
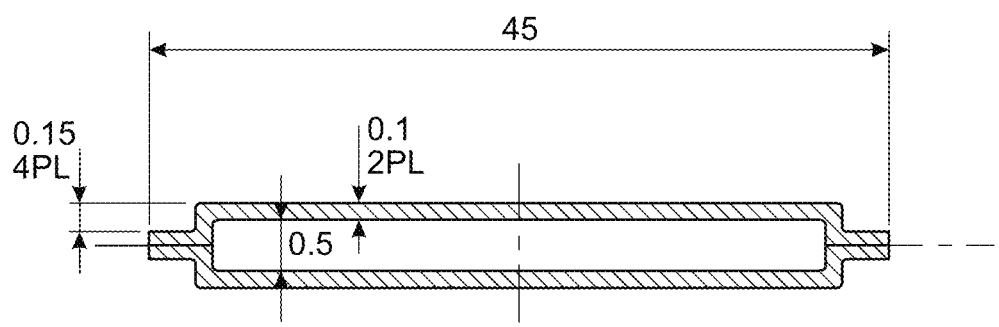
Figure 18:
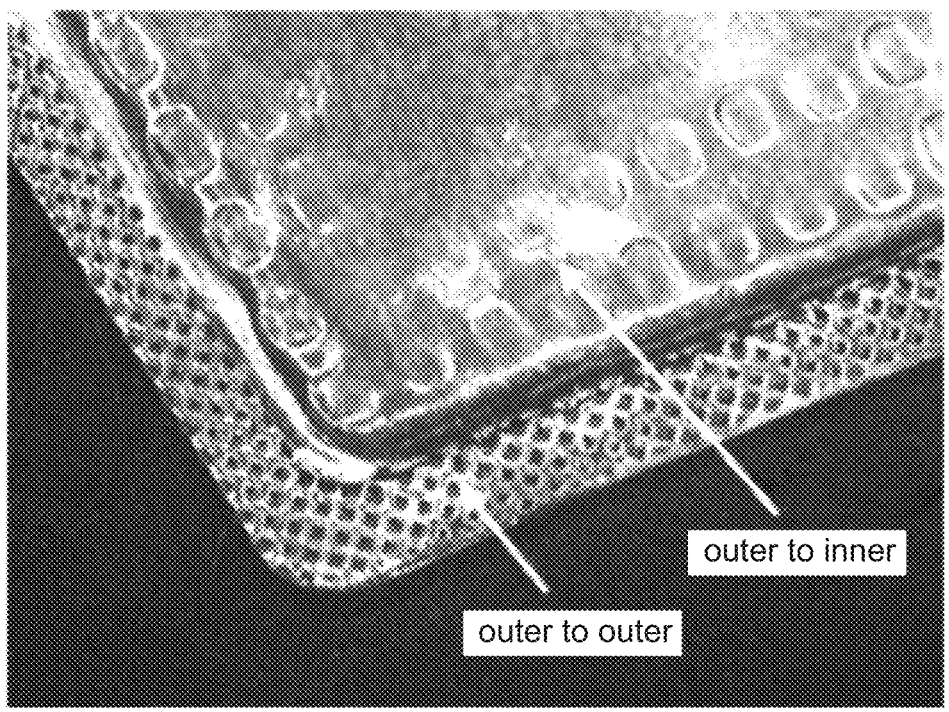
FIG. 18 shows an exemplary welded gastroretentive folded device of the present invention.
Figure 19:
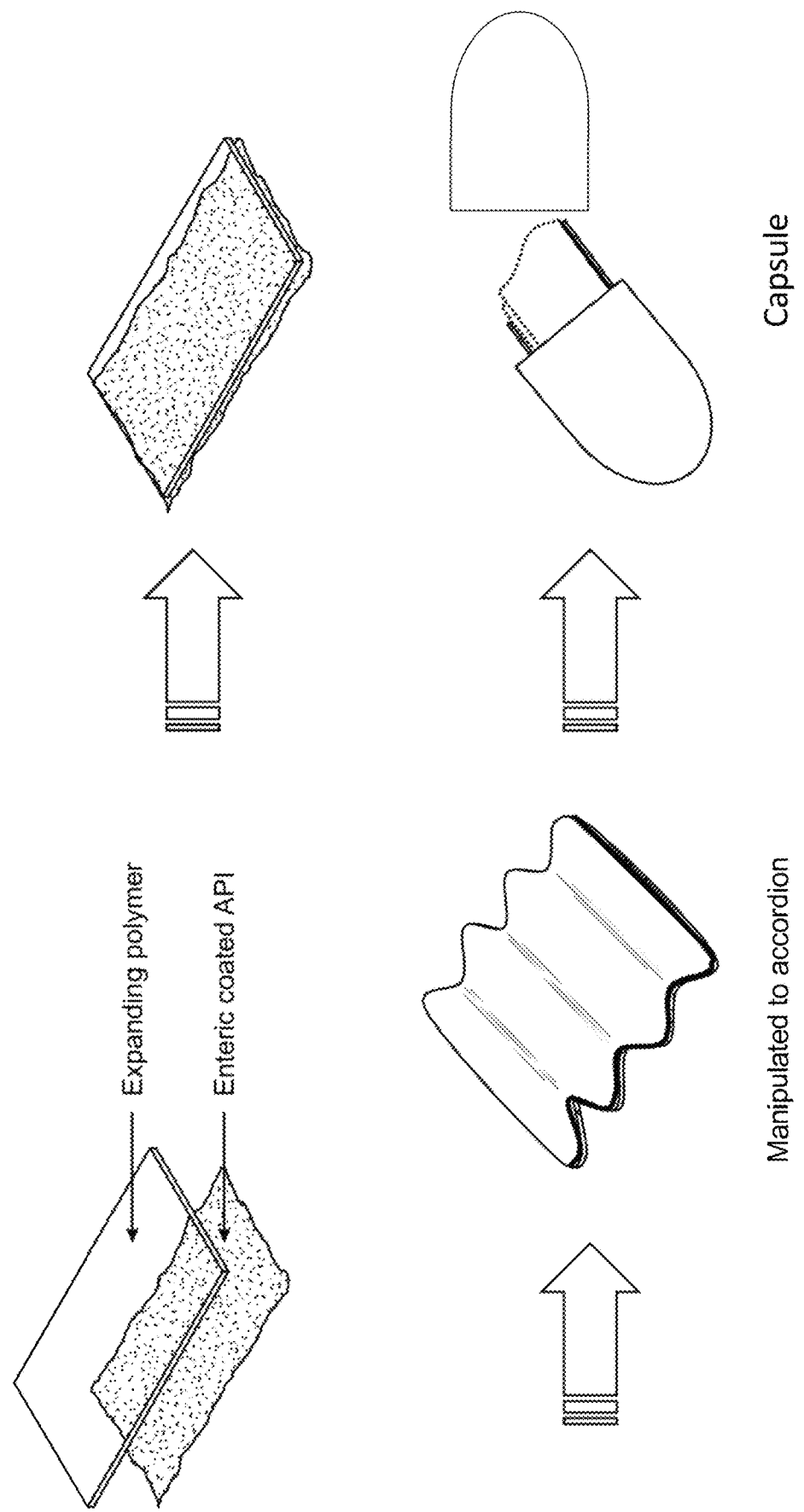
FIG. 19 shows an exemplary design for a gastroretentive folded dosage form of the present invention. The dosage form has an internal layer comprising API and an outer membrane covering the internal layer. The internal layer and the outer membrane are then folded into an accordion configuration and placed into a capsule.

| | Unmilled coarse API | Wet milled API |
|---|---|---|
| Particle size | Sieve cut of 130 μm to 350 μm | D50 = 60-100 μm |
| Particle morphology | 2D plate structure | 3D structure |
| SEM of uncoated API particles | FIG. 7A | FIG. 7B |
| Flow of API particle in fluid bed | Uneven flow due to API plate structure | Smooth and uniform flow |
| Coated crystals | Significant agglomeration due to uneven flow of particles in the coating process | Isolated and small coated particles with a small span |
| SEM of coated API particles | FIG. 7C | FIG. 7D |

As shown in Table 8 and FIGS. 7A-7D, unmilled coarse DMF particles are not suitable for making the enterically coated DMF particles of the present invention. Significant agglomeration of the coated particles was observed possibly due to the 2D plate structure of the coarse DMF particles. In contrast, wet-milled DMF particles have three dimensional morphology and desirable flowability, which results in small coated particles with uniform size distribution.

The invention claimed is:

1. A composition comprising dimethyl fumarate (DMF) particles having a volume median diameter ($D_{50}$) between 50 μm and 100 μm, wherein the span (($D_{90}$–$D_{10}$)/$D_{50}$) of the DMF particles in the composition is in the range of 1.3 to 1.9; wherein the DMF particles are characterized by one or more of a)-c):
   a) a circularity value in the range of 0.8 to 0.95;
   b) an aspect ratio in the range of 0.55 to 1.0; and
   c) a convexity value in the range of 0.95 to 1.0.

2. The composition of claim 1, wherein the span (($D_{90}$–$D_{10}$)/$D_{50}$) is in the range of 1.5 to 1.8.

3. The composition of claim 1, wherein less than 10% of the particles have a particle size below 10 μm.

4. The composition of claim 1, wherein the particles have a flow rate index in the range of 1.0 to 1.7.

5. The composition of claim 1, wherein specific energy (SE) of the particles is in the range of 4.0 to 13.0.

6. The composition of claim 1, wherein the particles have a flow function in the range of 2.0 to 20.0.

7. The composition of claim 1, wherein when the particles undergo permeability test at 1 kPa, the pressure drop is less than 0.4 mBar.

8. The composition of claim 1, wherein when the particles undergo permeability test at 15 kPa, the pressure drop is less than 0.5 mBar.

9. The composition of claim 1, wherein greater than 30% of the particles have intensity less than 80 when measured with a Malvern Morphologi G3 instrument.

10. The composition of claim 1, wherein 40% of the particles by accumulated volume have a circularity value in the range of 0.8 to 0.9.

11. A process for preparing the DMF particles of claim 1, wherein the process comprises the step of reducing DMF particle size by wet-milling.

12. DMF particles prepared by the process according to claim 11.

13. The composition of claim 1, wherein the DMF particles are prepared by a process comprising the step of reducing DMF particle size by wet-milling.

14. The composition of claim 1, wherein the DMF particles have a) a circularity value in the range of 0.8 to 0.95; b) an aspect ratio in the range of 0.55 to 1.0; and c) a convexity value in the range 0.95 to 1.0.

* * * * *